US009233111B2

(12) United States Patent
Heng et al.

(10) Patent No.: US 9,233,111 B2
(45) Date of Patent: Jan. 12, 2016

(54) PYRROLO PYRIMIDINE DERIVATIVES

(75) Inventors: Richard Heng, Hegenheim (FR); Elizabeth Kate Hoegenauer, Oberwil (CH); Guido Koch, Bettingen (CH); Robert Alexander Pulz, Basel (CH); Anna Vulpetti, Basel (CH); Rudolf Waelchli, Basel (CH)

(73) Assignee: NOVARTIS AG, Basel (CH)

( * ) Notice: Subject to any disclaimer, the term of this patent is extended or adjusted under 35 U.S.C. 154(b) by 192 days.

(21) Appl. No.: 14/130,536

(22) PCT Filed: Jul. 7, 2012

(86) PCT No.: PCT/IB2012/001699

§ 371 (c)(1),
(2), (4) Date: May 13, 2014

(87) PCT Pub. No.: WO2013/008095

PCT Pub. Date: Jan. 17, 2013

(65) Prior Publication Data

US 2014/0243306 A1   Aug. 28, 2014

Related U.S. Application Data

(60) Provisional application No. 61/505,560, filed on Jul. 8, 2011.

(51) Int. Cl.
  *C07D 487/04*   (2006.01)
  *A61K 31/519*   (2006.01)
  *A61P 35/00*    (2006.01)

(52) U.S. Cl.
  CPC ............ *A61K 31/519* (2013.01); *C07D 487/04* (2013.01)

(58) Field of Classification Search
  CPC .............................. C07D 487/04; A61K 31/519
  See application file for complete search history.

(56) References Cited

U.S. PATENT DOCUMENTS

| 6,160,010 A | 12/2000 | Uckun et al. |
| 2010/0216733 A1 | 8/2010 | Auclair et al. |
| 2010/0261776 A1 | 10/2010 | Conklin et al. |
| 2012/0071497 A1 | 3/2012 | Buggy et al. |

FOREIGN PATENT DOCUMENTS

| EP | 2322200 A2 | 5/2011 |
| WO | 99/62908 A2 | 12/1999 |
| WO | 99/65909 A1 | 12/1999 |
| WO | 00/43994 A1 | 7/2000 |
| WO | 00/75145 A1 | 12/2000 |
| WO | 01/66107 A2 | 9/2001 |
| WO | 02/38797 A2 | 5/2002 |
| WO | 02/051831 A1 | 7/2002 |
| WO | 2005/005429 A1 | 1/2005 |
| WO | 2006/017443 A2 | 2/2006 |
| WO | 2006/030031 A1 | 3/2006 |
| WO | 2006/099075 A2 | 9/2006 |
| WO | 2006/101783 A2 | 9/2006 |
| WO | 2006/124462 A2 | 11/2006 |
| WO | 2007/054831 A2 | 5/2007 |
| WO | 2007/070514 A1 | 6/2007 |
| WO | 2007/081517 A2 | 7/2007 |
| WO | 2007/084667 A2 | 7/2007 |
| WO | 2007/140222 A2 | 12/2007 |
| WO | 2008/009415 A2 | 1/2008 |
| WO | 2008/033834 A1 | 3/2008 |
| WO | 2008/033858 A2 | 3/2008 |
| WO | 2008/039218 A2 | 4/2008 |
| WO | 2008/110624 A2 | 9/2008 |
| WO | 2008/121742 A2 | 10/2008 |
| WO | 2008/144253 A1 | 11/2008 |
| WO | 2009/012283 A1 | 1/2009 |
| WO | 2009/059272 A1 | 5/2009 |
| WO | 2009/143018 A2 | 11/2009 |
| WO | 2009/143024 A2 | 11/2009 |
| WO | 2010/009342 A2 | 1/2010 |
| WO | 2010/030757 A2 | 3/2010 |
| WO | 2010/036316 A1 | 4/2010 |
| WO | 2010/036380 A1 | 4/2010 |
| WO | 2010/039939 A1 | 4/2010 |
| WO | 2010/068806 A1 | 6/2010 |
| WO | 2010/117935 A1 | 10/2010 |
| WO | 2010/117936 A1 | 10/2010 |
| WO | 2010/129053 A2 | 11/2010 |

(Continued)

OTHER PUBLICATIONS

Faith M Uckun et al., Bruton's tyrosine kinase as a molecular target in treatment of leukemias and lymphomas as well as inflammatory disorders and autoimunity, Expert Opinion on Therapeutic Patents, Informa Healthcare, 20, 11, 01.11.10, 1457-1470. (Jan. 11, 2010).

Klecka M. et al., Direct C—H borylation and C—H arylation of pyrrolo[2,3-d]pyrinnidines: synthesis of 6,8-disubstituted 7-deazapurines, Organic and Biomolecular Chemistry. Jan. 14, 2009; 7(5), 866-868.

Marcotte D.J. et al., Structures of human Bruton's tyrosine kinase in active and inactive conformations suggest a mechanism of activation for TEC family kinases. Protein Science. Mar. 2010; 19(3): 429-439.

(Continued)

*Primary Examiner* — Susanna Moore

(74) *Attorney, Agent, or Firm* — Sophie Binet Cross; Novartis Institutes for BioMedical Research, Inc.

(57) ABSTRACT

The present invention describes new pyrrolo pyrimidine derivatives and pharmaceutically acceptable salts thereof which appear to interact with Bruton's tyrosine kinase (Btk). Accordingly, the novel pyrrolo pyrimidines may be effective in the treatment of autoimmune disorders, inflammatory diseases, allergic diseases, airway diseases, such as asthma and chronic obstructive pulmonary disease (COPD), transplant rejection, cancers e.g. of hematopoietic origin or solid tumors.

15 Claims, No Drawings

(56) References Cited

FOREIGN PATENT DOCUMENTS

| WO | 2011/029043 A1 | 3/2011 |
|----|----------------|--------|
| WO | 2011/029046 A1 | 3/2011 |
| WO | 2011/143459 A1 | 11/2011 |
| WO | 2012/058645 A1 | 5/2012 |
| WO | 2013/003629 A2 | 1/2013 |
| WO | 2013/008095 A1 | 1/2013 |
| WO | 2013/023084 A2 | 2/2013 |
| WO | 2013/026516 A1 | 2/2013 |
| WO | 2013/059738 A2 | 4/2013 |
| WO | 2013/071865 A1 | 5/2013 |

OTHER PUBLICATIONS

Apsel B. et al., Targeted polypharmacology: discovery of dual inhibitors of tyrosine and phosphoinositide kinases. Nature Chemical Biology . Oct. 12, 2008. 4(11): 691-699.

Karaman M. W. et al., A quantitative analysis of kinase inhibitor selectivity. Nature Biotechnology. Jan. 8, 2008; 26(1): 127-132.

PYRROLO PYRIMIDINE DERIVATIVES

This application is a U.S. national Phase filing of International Serial No. PCT/IB2012/001699 filed Jul. 7, 2012, and claims priority to U.S. provisional application No. 61/505,560 filed Jul. 8, 2011, the contents of which are incorporated herein by reference in their entirety.

The present invention describes new pyrrolo pyrimidine derivatives that are good drug candidates.

The compounds of the present invention may generally exhibit a selective inhibition of Bruton's tyrosine kinase (Btk).

BACKGROUND OF THE INVENTION

The essential role of Btk in autoimmune disease is underlined by the observations that Btk-deficient mice are protected in standard preclinical models for rheumatoid arthritis (Jansson and Holmdahl, 1993), systemic lupus erythematosus (Steinberg, B. J. et al., J. Clin. Invest, 70, 587-597, 1982), as well as allergic disease and anaphylaxis (Hata, D. et al., J. Exp. Med. 187, 1235-1247, 1998). In addition, many cancers and lymphomas express Btk and appear to be dependent on Btk function (Davis, R. E. et al., Nature, 463, 88-92, 2010).

Therefore, inhibition of Btk activity may be useful in the treatment of immune disorders such as rheumatoid arthritis, systemic lupus erythematosus, allergic diseases, anaphylaxis and inflammatory conditions. Moreover, inhibition of Btk may be useful in the treatment of cancers of haematopoietic origin including chronic myelogenous leukemia, myeloid leukemia, non-Hodgkin lymphoma and other B cell lymphomas.

The compounds of the present invention may therefore potentially be useful in the treatment of a wide range of disorders, particularly Btk-related diseases or disorders, and may for example be useful in the treatment of autoimmune disorders, inflammatory diseases, allergic diseases, airway diseases, such as asthma and chronic obstructive pulmonary disease (COPD), transplant rejection, or cancers e.g. of hematopoietic origin or solid tumors.

More particularly, the present invention provides a compound of formula (I) or a pharmaceutically acceptable salt thereof;

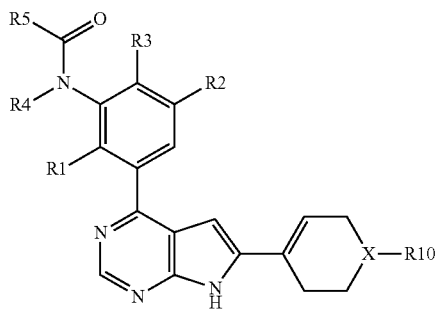

(I)

wherein,
R1 is hydrogen, $C_1$-$C_6$ alkyl optionally substituted by hydroxy;
R2 is hydrogen or halogen;
R3 is hydrogen or halogen;
R4 is hydrogen,
R5 is phenyl optionally substituted by halogen; $SF_5$; NR6R7; hydroxy; $C_1$-$C_6$ alkoxy; $C_1$-$C_6$ alkenyl; $C_1$-$C_6$ alkyl carbonyl; $C_1$-$C_6$ alkyl optionally substituted by hydroxy, halogen, or $C_1$-$C_6$ alkoxy; or $C_3$-$C_6$ cycloalkyl optionally substituted by halogen, hydroxy, or $C_1$-$C_6$ alkyl optionally substituted by halogen; or R5 is a 4-14 membered mono- or bicyclic heterocyclyl or heteroaryl ring system comprising 1, 2 or 3 heteroatoms selected from N, S and O that ring being optionally substituted by halogen; hydroxy; $C_1$-$C_6$ alkoxy optionally substituted by hydroxy or halogen; or $C_1$-$C_6$ alkyl optionally substituted by hydroxy or halogen;

or R4 and R5 together with the atoms to which they are bound form a piperidone ring, optionally comprising an annulated phenyl ring, any such ring being optionally substituted by $C_1$-$C_6$ alkyl, $C_1$-$C_6$ alkoxy, or $C_3$-$C_6$ cycloalkyl each of which substitution member may optionally be substituted by halogen or hydroxy;

R6 and R7 are independently selected from hydrogen or $C_1$-$C_6$ alkyl;

or R6 and R7 together with the nitrogen atom to which they are bound form a 4-8 membered saturated azacycloalkane ring, optionally substituted by halogen, hydroxy or $C_1$-$C_6$ alkyl;

X is O, $S(O)_n$ wherein n is 0, 1 or 2, or

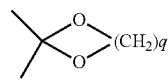

wherein q is 2 or 3, and R10 is absent;

or X is CH or N; and R10 is hydrogen, hydroxy, —NR6R7, —CO—R11, —S(O)$_p$—R12 wherein p is 1 or 2, R11 is $C_1$-$C_6$ alkyl optionally substituted by hydroxy, cyano, halogen, carboxy or $C_1$-$C_6$ alkoxy carbonyloxy; or NR6R7; and R12 is $C_1$-$C_6$ alkyl or NR6R7.

In another embodiment the present invention provides a compound of formula (I) or a pharmaceutically acceptable salt thereof wherein R1 is hydrogen, methyl or hydroxymethyl, R2 and R3 are independently hydrogen or fluoro, R4 is hydrogen, R5 is phenyl substituted by halogen; $C_1$-$C_6$ alkoxy or $C_1$-$C_6$ alkyl optionally substituted by halogen or hydroxy; or $C_3$-$C_6$ cycloalkyl optionally substituted by halogen, hydroxy, $C_1$-$C_6$ alkyl optionally substituted by halogen; X is O, S(O), wherein n is 0, 1 or 2, or

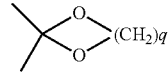

wherein q is 2 or 3, and R10 is absent;
and the remaining variables are as defined above.

In another embodiment the present invention provides a compound of formula (I) or a pharmaceutically acceptable salt thereof wherein R1 is hydrogen, methyl or hydroxymethyl, R2 and R3 are independently hydrogen or fluoro, R4 together with R5 is a 3,4-dihydro-2H-isoquinolin-1-one optionally substituted by $C_3$-$C_6$ cycloalkyl or $C_1$-$C_6$ alkyl optionally substituted by hydroxy; X is O, S(O), wherein n is 0, 1 or 2, or

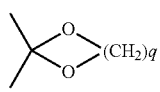

wherein q is 2 or 3, and R10 is absent; and the remaining variables are as defined above.

In another embodiment the present invention provides a compound of formula (I) or a pharmaceutically acceptable salt thereof wherein R1 is hydrogen, methyl or hydroxymethyl, R2 and R3 are independently hydrogen or fluoro, R4 is hydrogen, R5 is phenyl substituted by halogen; $C_1$-$C_6$ alkoxy; $C_1$-$C_6$ alkyl optionally substituted by halogen or hydroxy; or $C_3$-$C_6$ cycloalkyl optionally substituted by halogen, hydroxy, or $C_1$-$C_6$ alkyl optionally substituted by halogen; X stands for O and R10 is absent; or X stands for N, and R10 is hydrogen or —CO—R11, and the remaining variables are as defined above.

In another embodiment the present invention provides a compound of formula (I) or a pharmaceutically acceptable salt thereof wherein R1 is hydrogen, methyl or hydroxymethyl, R2 and R3 are independently hydrogen or fluoro, R4 is hydrogen; R5 is phenyl substituted by $C_1$-$C_6$ alkoxy; $C_1$-$C_6$ alkyl optionally substituted by halogen or hydroxy; or $C_3$-$C_6$ cycloalkyl optionally substituted by halogen, hydroxy, or $C_1$-$C_6$ alkyl optionally substituted by halogen; X stands for N, R10 is hydrogen or —CO—R11, R11 stands for NR6R7 wherein R6 and R7 are independently hydrogen or methyl; and the remaining variables are as defined above.

In another embodiment the present invention provides a compound of formula (I) or a pharmaceutically acceptable salt thereof wherein R1 is hydrogen, methyl or hydroxymethyl, R2 and R3 are independently hydrogen or fluoro, R4 is hydrogen, R5 is azetidine optionally substituted by $C_1$-$C_6$ alkoxy, X stands for N, and R10 is hydrogen or —CO—R11, and the remaining variables are as defined above.

In another embodiment the present invention provides a compound of formula (I) or a pharmaceutically acceptable salt thereof wherein R1 is hydrogen, methyl or hydroxymethyl, R2 and R3 are independently hydrogen or fluoro, R4 together with R5 is a 3,4-dihydro-2H-isoquinolin-1-one optionally substituted by $C_3$-$C_6$ cycloalkyl or $C_1$-$C_6$ alkyl optionally substituted by hydroxy, X stands for N, and R10 is hydrogen or —CO—R11, and the remaining variables are as defined above.

In another embodiment the present invention provides a compound of formula (I) or a pharmaceutically acceptable salt thereof wherein R1 is hydrogen, methyl or hydroxymethyl, R2 and R3 are independently hydrogen or fluoro, R4 together with R5 is a 3,4-dihydro-2H-isoquinolin-1-one substituted by $C_3$-$C_6$ cycloalkyl or $C_1$-$C_6$ alkyl optionally substituted by hydroxy in the 6-position of said isoquinolin-ring, X stands for N, and R10 is hydrogen or —CO—R11, and the remaining variables are as defined above.

In another embodiment the present invention provides a compound of formula (I) or a pharmaceutically acceptable salt thereof wherein R1 is hydrogen, methyl or hydroxymethyl, R2 and R3 are independently hydrogen or fluoro, R4 is hydrogen, R5 is azetidine optionally substituted by $C_1$-$C_6$ alkoxy, X stands for 0, and the remaining variables are as defined above.

In another embodiment the present invention provides a compound of formula (I) or a pharmaceutically acceptable salt thereof wherein R1 is hydrogen, methyl or hydroxymethyl, R2 and R3 are independently hydrogen or fluoro, R4 together with R5 is a 3,4-dihydro-2H-isoquinolin-1-one optionally substituted by $C_3$-$C_6$ cycloalkyl or $C_1$-$C_6$ alkyl optionally substituted by hydroxy, X stands for 0, and the remaining variables are as defined above.

In another embodiment the present invention provides a compound of formula (I) or a pharmaceutically acceptable salt thereof wherein R1 is hydrogen, methyl or hydroxymethyl, R2 and R3 are independently hydrogen or fluoro, R4 together with R5 is a 3,4-dihydro-2H-isoquinolin-1-one substituted by $C_3$-$C_6$ cycloalkyl or $C_1$-$C_6$ alkyl optionally substituted by hydroxy in the 6-position of said isoquinolin-ring, X stands for 0, and the remaining variables are as defined above.

In another embodiment the present invention provides a compound of formula (I) or a pharmaceutically acceptable salt thereof wherein R1 is hydrogen, methyl or hydroxymethyl, R2 and R3 are independently from each other selected from hydrogen and halogen, R4 is hydrogen, R5 is phenyl substituted one or more times by halogen, $C_3$-$C_6$ cycloalkyl, or $C_1$-$C_6$ alkyl optionally substituted by hydroxy, X stands for O or S, and R10 is absent.

In another embodiment the present invention provides a compound of formula (I) or a pharmaceutically acceptable salt thereof wherein R1 is methyl or hydroxymethyl, R2 and R3 are independently from each other selected from hydrogen and halogen, R4 is hydrogen, R5 is phenyl substituted one or more times by halogen, $C_3$-$C_6$ cycloalkyl, or $C_1$-$C_6$ alkyl optionally substituted by hydroxy, X stands for N, R10 is hydrogen or —CO—R11, and R11 is NR6R7 wherein R6 and R7 are independently selected from $C_1$-$C_6$-alkyl.

With regard to a compound of formula (I) the following significances represent further embodiments of the invention independently, collectively or in any combination or in any sub-combination thereof:

1. R1 is hydrogen, methyl or hydroxymethyl;
2. R1 is methyl or hydroxymethyl;
3. R2 and R3 are independently hydrogen or fluoro;
4. R1 is methyl or hydroxymethyl and R2 and R3 are independently hydrogen or fluoro;
5. R4 is hydrogen;
6. R4 together with R5 is a 3,4-dihydro-2H-isoquinolin-1-one optionally substituted by $C_3$-$C_6$ cycloalkyl or $C_1$-$C_6$ alkyl optionally substituted by hydroxy;
7. R4 together with R5 is a 3,4-dihydro-2H-isoquinolin-1-one optionally substituted by $C_3$-$C_6$ cycloalkyl or $C_1$-$C_6$ alkyl optionally substituted by hydroxy in the 6-position of the 3,4-dihydro-2H-isoquinolin-1-one ring;
8. R5 is phenyl optionally substituted by —NR6R7, halogen; $C_1$-$C_6$ alkoxy, $C_1$-$C_6$ alkenyl, $C_3$-$C_6$ cycloalkyl, or $C_1$-$C_6$ alkyl optionally substituted by halogen or hydroxy;
9. R5 is phenyl substituted by —NR6R7, halogen, $C_1$-$C_6$ alkoxy or $C_1$-$C_6$ alkyl optionally substituted by halogen or hydroxy;
10. R5 is phenyl substituted by halogen, $C_1$-$C_6$ alkoxy, $C_3$-$C_6$ cycloalkyl or $C_1$-$C_6$ alkyl optionally substituted by fluoro or hydroxy;
11. R5 is a 4-, 5-, 6-, or 7-membered monocyclic heterocycle, or a 7-, 8-, 9-, 10-, 11-, or 12-membered bicyclic heterocycle comprising 1, 2 or 3 heteroatoms selected from N, S and O that ring being optionally substituted by halogen; hydroxy; $C_1$-$C_6$ alkoxy optionally substituted by hydroxy or halogen; or $C_1$-$C_6$ alkyl optionally substituted by hydroxy or halogen;
12. R5 is a 4-, 5-, 6-, or 7-membered monocyclic heterocycle comprising 1 or 2 heteroatoms selected from N, S and O that ring being optionally substituted by halogen; hydroxy; $C_1$-$C_6$ alkoxy optionally substituted by hydroxy or halogen; or $C_1$-$C_6$ alkyl optionally substituted by hydroxy or halogen;
13. R5 is azetidine substituted by $C_1$-$C_6$ alkoxy or $C_1$-$C_6$ alkyl;
14. X is O and R10 is absent or is N and R10 is H or CO—R11;
15. X is O and R10 is absent or is N and R10 is CO—R11;
16. X is O and R10 is absent;
17. X is N and R10 is CO—R11;
18. R11 is NR6R7 and R6 and R7 are independently selected from hydrogen or $C_1$-$C_6$ alkyl;
19. R11 is NR6R7 and R6 and R7 are independently selected from $C_1$-$C_6$ alkyl;
20. R11 is NR6R7 and R6 and R7 are independently selected from $C_1$-$C_3$ alkyl;
21. R11 is NR6R7 and R6 and R7 are methyl.

In another embodiment the present invention provides a compound of formula (I) or a pharmaceutically acceptable salt thereof for use as a medicament.

In another embodiment the present invention provides a compound of formula (I) or a pharmaceutically acceptable salt thereof for use in the treatment of a disease or disorder mediated by Btk.

In another embodiment the present invention provides a compound of formula (I) or a pharmaceutically acceptable salt thereof, which is selected from:

4-(4-{5-Fluoro-3-[4-(1-fluoro-cyclopropyl)-benzoylamino]-2-methyl-phenyl}-7H-pyrrolo[2'3-d]pyrimidin-6-yl)-3,6-dihydro-2H-pyridine-1-carboxylic acid dimethylamide,
4-(4-{3-[(3,3-Dimethyl-2,3-dihydro-benzofuran-6-carbonyl)-amino]-5-fluoro-2-methyl-phenyl}-7H-pyrrolo[2'3-d]pyrimidin-6-yl)-3,6-dihydro-2H-pyridine-1-carboxylic acid dimethylamide,
4-(4-{5-Fluoro-2-methyl-3-[(5-methyl-4,5,6,7-tetrahydro-benzo[b]thiophene-2-carbonyl)-amino]-phenyl}-7H-pyrrolo[2'3-d]pyrimidin-6-yl)-3,6-dihydro-2H-pyridine-1-carboxylic acid dimethylamide,
4-(4-{5-Fluoro-3-[4-isopropyl-methyl-amino)-benzoylamino]-2-methyl-phenyl}-7H-pyrrolo[2'3-d]pyrimidin-6-yl)-3,6-dihydro-2H-pyridine-1-carboxylic acid dimethylamide,
3-Methyl-1H-indole-6-carboxylic acid {3-[6-(1-dimethylcarbamoyl-1,2,3,6-tetrahydro-pyridin-4-yl)-7H-pyrrolo[2,3-d]pyrimidin-4-yl]-5-fluoro-2-methyl-phenyl}-amide,
4-(4-{5-Fluoro-3-[4-(2-hydroxy-1,1-dimethyl-ethyl)-benzoylamino]-2-methyl-phenyl}-7H-pyrrolo[2,3-d]pyrimidin-6-yl)-3,6-dihydro-2H-pyridine-1-carboxylic acid dimethylamide,
4-{4-[5-Fluoro-2-methyl-3-(4-piperidin-1-yl-benzoylamino)-phenyl]-7H-pyrrolo[2,3-d]pyrimidin-6-yl}-3,6-dihydro-2H-pyridine-1-carboxylic acid dimethylamide,
4-{4-[5-Fluoro-3-(isopropenyl-benzoylamino)-2-methylphenyl]-7H-pyrrolo[2,3-d]pyrimidin-6-yl}-3,6-dihydro-2H-pyridine-1-carboxylic acid dimethylamide,
4-(4-{5-Fluoro-2-methyl-3-[4-(1-trifluoromethyl-cyclopropyl)-benzoylamino]-phenyl}-7H-pyrrolo[2,3-d]pyrimidin-6-yl)-3,6-dihydro-2H-pyridine-1-carboxylic acid dimethylamide,
4-{4-[5-Fluoro-3-(4-isopropoxy-benzoylamino)-2-methylphenyl]-7H-pyrrolo[2,3-d]pyrimidin-6-yl}-3,6-dihydro-2H-pyridine-1-carboxylic acid dimethylamide,
4-(4-{5-Fluoro-3-[4-pentafluorothio-benzoylamino]-2-methyl-phenyl}-7H-pyrrolo[2,3-d]pyrimidin-6-yl)-3,6-dihydro-2H-pyridine-1-carboxylic acid dimethylamide,
4-(4-{5-Fluoro-3-[4-(2-methoxy-1,1-dimethyl-ethyl)-benzoylamino]-2-methyl-phenyl}-7H-pyrrolo[2,3-d]pyrimidin-6-yl)-3,6-dihydro-2H-pyridine-1-carboxylic acid dimethylamide,
4-(4-{5-Fluoro-3-[4-(1-methoxy-1-methyl-ethyl)-benzoylamino]-2-methyl-phenyl}-7H-pyrrolo[2,3-d]pyrimidin-6-yl)-3,6-dihydro-2H-pyridine-1-carboxylic acid dimethylamide,
1-Methyl-1H-pyrrolo[2,3-b]pyridine-6-carboxylic acid {3-[6-(1-dimethyl-carbamoyl-1,2,3,6-tetrahydro-pyridin-4-yl)-7H-pyrrolo[2,3-d]pyrimidin-4-yl]-5-fluoro-2-methyl-phenyl}-amide,
4-{4-[3-(4-Dimethylamino-benzoylamino)-5-fluoro-2-methyl-phenyl]-7H-pyrrolo[2,3-d]pyrimidin-6-yl}-3,6-dihydro-2H-pyridine-1-carboxylic acid dimethylamide,
4-(4-{3-[2-Fluoro-4-(1-hydroxy-1-methyl-ethyl)-benzoylamino]-2-hydroxymethyl-phenyl}-7H-pyrrolo[2,3-d]pyrimidin-6-yl)-3,6-dihydro-2H-pyridine-1-carboxylic acid dimethylamide,
4-{4-[3-(4-Cyclopropyl-benzoylamino)-2-hydroxymethyl-phenyl]-7H-pyrrolo[2,3-d]pyrimidin-6-yl}-3,6-dihydro-2H-pyridine-1-carboxylic acid dimethylamide,
4-(4-{5-Fluoro-2-methyl-3-[4-(2,2,2-trifluoro-1-hydroxy-1-methyl-ethyl)-benzoylamino]-phenyl}-7H-pyrrolo[2,3-d]pyrimidin-6-yl)-3,6-dihydro-2H-pyridine-1-carboxylic acid dimethylamide,
4-{4-[3-(4-Acetyl-benzoylamino)-5-fluoro-2-methyl-phenyl]-7H-pyrrolo[2,3-d]pyrimidin-6-yl}-3,6-dihydro-2H-pyridine-1-carboxylic acid dimethylamide,
4-{4-[3-(4-Cyclopropyl-benzoylamino)-4-fluoro-phenyl]-7H-pyrrolo[2,3-d]pyrimidin-6-yl}-3,6-dihydro-2H-pyridine-1-carboxylic acid dimethylamide,
4-(4-{4-Fluoro-3-[4-(2-hydroxy-1,1-dimethyl-ethyl)-benzoylamino]-phenyl}-7H-pyrrolo[2,3-d]pyrimidin-6-yl)-3,6-dihydro-2H-pyridine-1-carboxylic acid dimethylamide,
N-{3-[6-(3,6-Dihydro-2H-pyran-4-yl)-7H-pyrrolo[2,3-d]pyrimidin-4-yl]-5-fluoro-2-methyl-phenyl}-2-fluoro-4-(1-hydroxy-1-methyl-ethyl)-benzamide,
N-{3-[6-(3,6-Dihydro-2H-pyran-4-yl)-7H-pyrrolo[2,3-d]pyrimidin-4-yl]-2-hydroxymethyl-phenyl}-2-fluoro-4-(1-hydroxy-1-methyl-ethyl)-benzamide,
4-tert-Butyl-N-{3-[6-(3,6-dihydro-2H-thiopyran-4-yl)-7H-pyrrolo[2,3-d]pyrimidin-4-yl]-5-fluoro-2-methyl-phenyl}-benzamide,
4-tert-Butyl-N-{5-fluoro-2-methyl-3-[6-(3,6-dihydro-1-oxido-2H-thiopyran-4-yl)-7H-pyrrolo[2,3-d]pyrimidin-4-yl]-phenyl}-benzamide,
4-tert-Butyl-N-{3-[6-(3,6-dihydro-1,1-dioxido-2H-thiopyran-4-yl)-7H-pyrrolo[2,3-d]pyrimidin-4-yl]-5-fluoro-2-methyl-phenyl}-benzamide,
4-tert-Butyl-N-{3-[6-(1,4-dioxa-spiro[4.5]dec-7-en-8-yl)-7H-pyrrolo[2,3-d]pyrimidin-4-yl]-5-fluoro-2-methyl-phenyl}-benzamide,
4-tert-Butyl-N-{5-fluoro-3-[6-(4-hydroxy-cyclohex-1-enyl)-7H-pyrrolo[2,3-d]pyrimidin-4-yl]-2-methyl-phenyl}-benzamide,
4-{4-[3-(4-Cyclopropyl-benzoylamino)-5-fluoro-2-methyl-phenyl]-7H-pyrrolo[2'3-d]pyrimidin-6-yl}-3,6-dihydro-2H-pyridine-1-carboxylic acid dimethylamide,
4-Cyclopropyl-N-(5-fluoro-2-methyl-3-{6-[1-(pyrrolidine-1-carbonyl)-1,2,3,6-tetrahydro-pyridin-4-yl]-7H-pyrrolo[2,3-d]pyrimidin-4-yl}-phenyl)-benzamide,
Acetic acid 2-(4-{4-[3-(4-cyclopropyl-benzoylamino)-5-fluoro-2-methyl-phenyl]-7H-pyrrolo[2,3-d]pyrimidin-6-yl}-3,6-dihydro-2H-pyridin-1-yl)-2-oxo-ethyl ester, 4-Cyclopropyl-N-(5-fluoro-3-{6-[1-(2-hydroxy-actyl)-1,2,3,6-tetrahydro-pyridin-4-yl]-7H-pyrrolo[2,3-d]pyrimidin-4-yl}-2-methyl-phenyl)benzamide, N-(3-{6-[1-(2-Cyano-acetyl)-1,2,3,6-tetrahydro-pyridin-4-yl]-7H-pyrrolo[2,3-d]pyrimidin-4-yl}-5-fluoro-2-methyl-phenyl)-4-cyclopropyl-benzamide, N-(5-Fluoro-2-methyl-3-{6-[1-(pyrrolidine-1-carbonyl)-1,2,3,6-tetrahydro-pyridin-4-yl]-7H-pyrrolo[2,3-d]pyrimidin-4-yl}-phenyl)-4-(pentafluoro-sulfanyl)-benzamide, Acetic acid 2-[4-(4-{5-fluoro-2-methyl-3-[4-(pentafluoro-sulfanyl)-benzoylamino]-phenyl}-7H-pyrrolo[2,3-d]pyrimidin-6-yl)-3,6-dihydro-2H-pyridin-1-yl]-2-oxo-ethyl ester, N-(5-Fluoro-3-{6-[1-(2-hydroxy-acetyl)-1,2,3,6-tetrahydro-pyridin-4-yl]-7H-pyrrolo[2,3-d]pyrimidin-4-yl}-2-methyl-phenyl)-4-(pentafluoro-sulfanyl)-benzamide, 4-{4-[3-(4-tert-Butyl-benzoylamino)-2-(tert-butyl-diphenyl-silanyloxymethyl)-phenyl]-7H-pyrrolo[2,3-d]pyrimidin-6-yl}-3,6-dihydro-2H-pyridine-1-carboxylic acid tert-butyl ester, 4-tert-Butyl-N-(3-{6-[1-(2-fluoro-acetyl)-1,2,3,6-tetrahydro-pyridin-4-yl]-7H-pyrrolo[2,3-d]pyrimidin-4-yl}-2-hydroxymethyl-phenyl)-benzamide, 4-(4-{5-Fluoro-3-[2-fluoro-4-(1-hydroxy-1-methyl-ethyl)-benzoylamino]-2-methyl-phenyl}-7H-pyrrolo[2,3-d]pyrimidin-6-yl)-3,6-dihydro-2H-pyridine-1-carboxylic acid dimethylamide, 4-tert-Butyl-N-{5-fluoro-2-methyl-3-[6-(1,2,3,6-tetrahydro-pyridin-4-yl)-7H-pyrrolo[2,3-d]pyrimidin-4-yl]-phenyl}-benzamide, 4-{4-[3-(4-tert-Butyl-benzoylamino)-5-fluoro-2-methyl-phenyl]-7H-pyrrolo[2,3-d]pyrimidin-6-yl}-3,6-dihydro-2H-pyridine-1-carboxylic acid dimethylamide, 4-tert-Butyl-N-{5-fluoro-3-[6-(1-methanesulfonyl-1,2,3,6-tetrahydro-pyridin-4-yl)-7H-pyrrolo[2,3-d]pyrimidin-4-yl]-2-methyl-phenyl}-benzamide, 4-tert-Butyl-N-{3-[6-(1-dimethylsulfamoyl-1,2,3,6-tetrahydro-pyridin-4-yl)-7H-pyrrolo[2,3-d]pyrimidin-4-yl]-5-fluoro-2-methyl-phenyl}-benzamide, 4-tert-Butyl-N-{3-[6-(1-methanesulfonyl-1,2,3,6-tetrahydro-pyridin-4-yl)-7H-pyrrolo[2,3-d]pyrimidin-4-yl]-2-methyl-phenyl}-benzamide, 4-{4-[3-(6-tert-Butyl-1-oxo-3,4-dihydro-1H-isoquinolin-2-yl)-2-hydroxymethyl-phenyl]-7H-pyrrolo[2,3-d]pyrimidin-6-yl}-3,6-dihydro-2H-pyridine-1-carboxylic acid dimethylamide, 4-{4-[3-(6-Cyclopropyl-1-oxo-3,4-dihydro-1H-isoquinolin-2-yl)-2-hydroxymethyl-phenyl]-7H-pyrrolo[2,3-d]pyrimidin-6-yl}-3,6-dihydro-2H-pyridine-1-carboxylic acid dimethylamide, 4-(4-{2-Hydroxymethyl-3-[6-(1-hydroxy-1-methyl-ethyl)-1-oxo-3,4-dihydro-1H-isoquinolin-2-yl]-phenyl}-7H-pyrrolo[2,3-d]pyrimidin-6-yl)-3,6-dihydro-2H-pyridine-1-carboxylic acid dimethylamide, 4-tert-Butyl-N-{3-[6-(3,6-dihydro-2H-pyran-4-yl)-7H-pyrrolo[2,3-d]pyrimidin-4-yl]-2-hydroxymethyl-phenyl}-benzamide, 4-tert-Butyl-N-{3-[6-(3,6-dihydro-2H-pyran-4-yl)-7H-pyrrolo[2,3-d]pyrimidin-4-yl]-5-fluoro-2-methyl-phenyl}-benzamide, N-{3-[6-(3,6-Dihydro-2H-pyran-4-yl)-7H-pyrrolo[2,3-d]pyrimidin-4-yl]-5-fluoro-2-methyl-phenyl}-4-dimethylamino-benzamide, 4-tert-Butyl-N-{3-[6-(3,6-dihydro-2H-thiopyran-4-yl)-7H-pyrrolo[2,3-d]pyrimidin-4-yl]-2-methyl-phenyl}-benzamide, 4-tert-Butyl-N-{2-methyl-3-[6-(3,6-dihydro-1-oxido-2H-thiopyran-4-yl)-7H-pyrrolo[2,3-d]pyrimidin-4-yl]-phenyl}-benzamide, 4-tert-Butyl-N-{3-[6-(3,6-dihydro-1,1-dioxido-2H-thiopyran-4-yl)-7H-pyrrolo[2,3-d]pyrimidin-4-yl]-2-methyl-phenyl}-benzamide, 4-tert-Butyl-N-{3-[6-(1,4-dioxa-spiro[4.5]dec-7-en-8-yl)-7H-pyrrolo[2,3-d]pyrimidin-4-yl]-2-hydroxymethyl-phenyl}-benzamide, 4-tert-Butyl-N-{3-[6-(4-hydroxy-cyclohex-1-enyl)-7H-pyrrolo[2,3-d]pyrimidin-4-yl]-2-hydroxymethyl-phenyl}-benzamide, 4-tert-Butyl-N-{3-[6-(4-dimethylamino-cyclohex-1-enyl)-7H-pyrrolo[2,3-d]pyrimidin-4-yl]-2-hydroxymethyl-phenyl}-benzamide, 4-(4-{3-[(3-tert-Butoxy-azetidine-1-carbonyl)-amino]-5-fluoro-2-methyl-phenyl}-7H-pyrrolo[2,3-d]pyrimidin-6-yl)-3,6-dihydro-2H-pyridine-1-carboxylic acid dimethylamide, 4-(4-{5-Fluoro-3-[(3-isopropoxy-azetidine-1-carbonyl)-amino]-2-methyl-phenyl}-7H-pyrrolo[2,3-d]pyrimidin-6-yl)-3,6-dihydro-2H-pyridine-1-carboxylic acid dimethylamide, 5-Fluoro-1,3-dihydro-isoindole-2-carboxylic acid {3-[6-(1-dimethylcarbamoyl-1,2,3,6-tetrahydro-pyridin-4-yl)-7H-pyrrolo[2,3-d]pyrimidin-4-yl]-5-fluoro-2-methyl-phenyl}-amide, 4-[4-(5-Fluoro-2-methyl-3-{[3-(2,2,2-trifluoro-1-trifluoromethyl-ethoxy)-azetidine-1-carbonyl]-amino}-phenyl)-7H-pyrrolo[2,3-d]pyrimidin-6-yl]-3,6-dihydro-2H-pyridine-1-carboxylic acid dimethylamide, 3-tert-Butoxy-azetidine-1-carboxylic acid {3-[6-(3,6-dihydro-2H-pyran-4-yl)-7H-pyrrolo[2,3-d]pyrimidin-4-yl]-5-fluoro-2-methyl-phenyl}-amide, 4-(4-{3-[(3-tert-Butoxy-azetidine-1-carbonyl)-amino]-4-fluoro-phenyl}-7H-pyrrolo[2,3-d]pyrimidin-6-yl)-3,6-dihydro-2H-pyridine-1-carboxylic acid dimethylamide, 4-(4-{3-[(3-tert-Butoxy-azetidine-1-carbonyl)-amino]-4-fluoro-2-methyl-phenyl}-7H-pyrrolo[2,3-d]pyrimidin-6-yl)-3,6-dihydro-2H-pyridine-1-carboxylic acid dimethylamide, 4-tert-Butyl-N-{3-[6-(3,6-dihydro-2H-pyran-4-yl)-7H-pyrrolo[2,3-d]pyrimidin-4-yl]-2-methyl-phenyl}-benzamide, 4-tert-Butyl-N-{3-[6-(1,4-dioxa-spiro[4.5]dec-7-en-8-yl)-7H-pyrrolo[2,3-d]pyrimidin-4-yl]-2-methyl-phenyl}-benzamide, 4-tert-Butyl-N-{3-[6-(4-hydroxy-cyclohex-1-enyl)-7H-pyrrolo[2,3-d]pyrimidin-4-yl]-2-methyl-phenyl}-benzamide, and 4-tert-Butyl-N-{3-[6-(4-dimethylamino-cyclohex-1-enyl)-7H-pyrrolo[2,3-d]pyrimidin-4-yl]-2-methyl-phenyl}-benzamide.

As used herein, the term "alkyl" refers to a fully saturated branched or unbranched hydrocarbon moiety having up to 20 carbon atoms. Unless otherwise provided, alkyl refers to hydrocarbon moieties having 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "alkenyl" refers to an unsaturated branched or unbranched hydrocarbon moiety having 2 to 20 carbon atoms. It comprises 2 to 20 carbon atoms, Unless otherwise provided, alkenyl refers to moieties having 2 to 16 carbon atoms, 2 to 10 carbon atoms, 2 to 7 carbon atoms, or 2 to 4 carbon atoms. Representative examples of alkenyl include, but are not limited to, ethenyl, n-propenyl, iso-propenyl, n-butenyl, sec-butenyl, iso-butenyl, tert-butenyl, n-pentenyl, isopentenyl, neopentenyl, n-hexenyl, 3-methylhexenyl, 2,2-dimethylpentenyl, 2,3-dimethylpentenyl, n-heptenyl, n-octenyl, n-nonenyl, n-decenyl and the like.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have about 1-7, more preferably about 1-4 carbons.

As used herein, the term "cycloalkyl" refers to saturated or unsaturated monocyclic, bicyclic or tricyclic hydrocarbon groups of 3-12 carbon atoms. Unless otherwise provided, cycloalkyl refers to cyclic hydrocarbon groups having between 3 and 9 ring carbon atoms or between 3 and 7 ring carbon atoms. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

As used herein, the term "azacycloalkane" refers to saturated or unsaturated monocyclic, bicyclic or tricyclic hydrocarbon groups of 3-12 carbon atoms as defined for "cycloalkyl", wherein one carbon atom is replaced by a nitrogen atom. Unless otherwise provided, azacycloalkyl refers to cyclic aza-hydrocarbon groups having between 2 and 9 ring carbon atoms and one nitrogen atom or between 2 and 7 ring carbon atoms and one nitrogen atom. Exemplary monocyclic aza-hydrocarbon groups include, but are not limited to, aziridinyl, azetidinly, pyrollidinyl, piperidinyl, azepanyl, dihydroazepinyl and the like.

As used herein, the term "halogen" or "halo" refers to fluoro, chloro, bromo, and iodo.

As used herein the term "heterocyclic", "heterocyclyl" or "heterocyclo" may refer to a saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl may include fused or bridged rings as well as spirocyclic rings. Examples of heterocycles include azetidine, tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

As used herein, the term "aryloxy" refers to both an —O-aryl and an —O-heteroaryl group, wherein aryl and heteroaryl are defined herein.

As used herein, the term "heteroaryl" refers to a 5-14 membered monocyclic- or bicyclic- or tricyclic-aromatic ring system, having 1 to 8 heteroatoms selected from N, O or S. Typically, the heteroaryl is a 5-10 membered ring system (e.g., 5-7 membered monocycle or an 8-10 membered bicycle) or a 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-isoquinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenanthrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$, $^{31}P$, $^{32}P$, $^{35}S$, $^{36}Cl$, $^{125}I$ respectively. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by Btk, or (ii) associated with Btk activity, or (iii) characterized by activity (normal or abnormal) of Btk; or (2) reducing or inhibiting the activity of Btk; or (3) reducing or inhibiting the expression of Btk. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of Btk; or reducing or inhibiting the expression of Btk partially or completely.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis- (Z)- or trans- (E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with
  a) diluents, e.g., lactose, dextrose, sucrose, mannitol, sorbitol, cellulose and/or glycine;
  b) lubricants, e.g., silica, talcum, stearic acid, its magnesium or calcium salt and/or polyethyleneglycol; for tablets also
  c) binders, e.g., magnesium aluminum silicate, starch paste, gelatin, tragacanth, methylcellulose, sodium carboxymethylcellulose and/or polyvinylpyrrolidone; if desired
  d) disintegrants, e.g., starches, agar, alginic acid or its sodium salt, or effervescent mixtures; and/or
  e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of formula I in free form or in salt form, exhibit valuable pharmacological properties, e.g. Btk modulating properties, e.g. as indicated by in vitro and in vivo tests as provided in the next sections and are therefore indicated for therapy.

Compounds of the invention may be useful in the treatment of an indication selected from: Autoimmune disorders, inflammatory diseases, allergic diseases, airway diseases, such as asthma and chronic obstructive pulmonary disease (COPD), transplant rejection; diseases in which antibody production, antigen presentation, cytokine production or lymphoid organogenesis are abnormal or are undesirable; including rheumatoid arthritis, systemic onset juvenile idiopathic arthritis (SOJIA), gout, pemphigus vulgaris, idiopathic thrombocytopenic purpura, systemic lupus erythematosus, multiple sclerosis, myasthenia gravis, Sjögren's syndrome, autoimmune hemolytic anemia, anti-neutrophil cytoplasmic antibodies (ANCA)-associated vasculitides, cryoglobulinemia, thrombotic thrombocytopenic purpura, chronic autoimmune urticaria, allergy (atopic dermatitis, contact dermatitis, allergic rhinitis), atherosclerosis, type 1 diabetes, type 2 diabetes, inflammatory bowel disease, ulcerative colitis, morbus Crohn, pancreatitis, glomerolunephritis, Goodpasture's syndrome, Hashimoto's thyroiditis, Grave's disease, antibody-mediated transplant rejection (AMR), graft versus host disease, B cell-mediated hyperacute, acute and chronic transplant rejection; thromboembolic disorders, myocardial infarct, angina pectoris, stroke, ischemic disorders, pulmonary embolism; cancers of haematopoietic origin including but not limited to multiple myeloma; leukemia; acute myelogenous leukemia; chronic myelogenous leukemia; lymphocytic leukemia; myeloid leukemia; non-Hodgkin lymphoma; lymphomas; polycythemia vera; essential thrombocythemia; myelofibrosis with myeloid metaplasia; and Waldenstroem disease.

Thus, as a further embodiment, the present invention provides the use of a compound of formula (I) or a salt thereof in therapy. In a further embodiment, the therapy is selected from a disease which may be treated by inhibition of Btk. In another embodiment, the disease is selected from the aforementioned list, suitably rheumatoid arthritis, systemic onset juvenile idiopathic arthritis (SOJIA), pemphigus vulgaris, idiopathic thrombocytopenic purpura, systemic lupus erythematosus, multiple sclerosis, myasthenia gravis, Sjögren's syndrome, autoimmune hemolytic anemia, anti-neutrophil cytoplasmic antibodies (ANCA)-associated vasculitides, cryoglobulinemia, thrombotic thrombocytopenic purpura, chronic autoimmune urticaria, atopic dermatitis, allergic rhinitis, type 1 diabetes, type 2 diabetes, inflammatory bowel disease, morbus Crohn, Goodpasture's syndrome, Grave's disease, antibody-mediated transplant rejection (AMR), B cell-mediated hyperacute, acute and chronic transplant rejection; multiple myeloma; acute myelogenous leukemia; chronic myelogenous leukemia; lymphocytic leukemia;

myeloid leukemia; non-Hodgkin lymphoma; myelofibrosis with myeloid metaplasia; and Waldenstroem disease, more suitably rheumatoid arthritis, systemic onset juvenile idiopathic arthritis (SOJIA), systemic lupus erythematosus, multiple sclerosis, Sjögren's syndrome, chronic autoimmune urticaria, atopic dermatitis, allergic rhinitis, type 1 diabetes, type 2 diabetes, inflammatory bowel disease, multiple myeloma; non-Hodgkin lymphoma.

In another embodiment, the invention provides a method of treating a disease which is treated by inhibition of Btk kinase comprising administration of a therapeutically acceptable amount of a compound of formula (I) or a salt thereof. In a further embodiment, the disease is selected from the aforementioned list, suitably rheumatoid arthritis, systemic onset juvenile idiopathic arthritis (SOJIA), pemphigus vulgaris, idiopathic thrombocytopenic purpura, systemic lupus erythematosus, multiple sclerosis, myasthenia gravis, Sjögren's syndrome, autoimmune hemolytic anemia, anti-neutrophil cytoplasmic antibodies (ANCA)-associated vasculitides, cryoglobulinemia, thrombotic thrombocytopenic purpura, chronic autoimmune urticaria, atopic dermatitis, allergic rhinitis, type 1 diabetes, type 2 diabetes, inflammatory bowel disease, morbus Crohn, Goodpasture's syndrome, Grave's disease, antibody-mediated transplant rejection (AMR), B cell-mediated hyperacute, acute and chronic transplant rejection; multiple myeloma; acute myelogenous leukemia; chronic myelogenous leukemia; lymphocytic leukemia; myeloid leukemia; non-Hodgkin lymphoma; myelofibrosis with myeloid metaplasia; and Waldenstroem disease, more suitably rheumatoid arthritis, systemic onset juvenile idiopathic arthritis (SOJIA), systemic lupus erythematosus, multiple sclerosis, Sjögren's syndrome, chronic autoimmune urticaria, atopic dermatitis, allergic rhinitis, type 1 diabetes, type 2 diabetes, inflammatory bowel disease, multiple myeloma; non-Hodgkin lymphoma.

Methods of Synthesizing Pyrrolo-Pyrimidines

Agents of the invention, i.e. compounds in accordance to the definition of formula (I), may be prepared by a reaction sequence (shown below) involving Suzuki coupling of a protected boronic esters II with the corresponding aryl halides I', conveniently furnishing intermediate III. Deprotection of III, e.g. with diluted hydrochloric acid in methanol or the like and acylation, e.g. with an appropriate acetylating agent, e.g. unsubstituted or substituted acetanhydride in the absence or presence of a solvent, of IV is followed by an additional Suzuki coupling with boronic ester VI and acylation of VII (optionally followed by a deprotection step), as shown in Reaction Scheme 1 below, wherein X denotes N, and the group PG refers to a protecting group such as for example, tert-butyloxycarbonyl, that may be easily removed e.g. by diluted hydrochloric acid in methanol or the like.

Reaction Scheme 1:

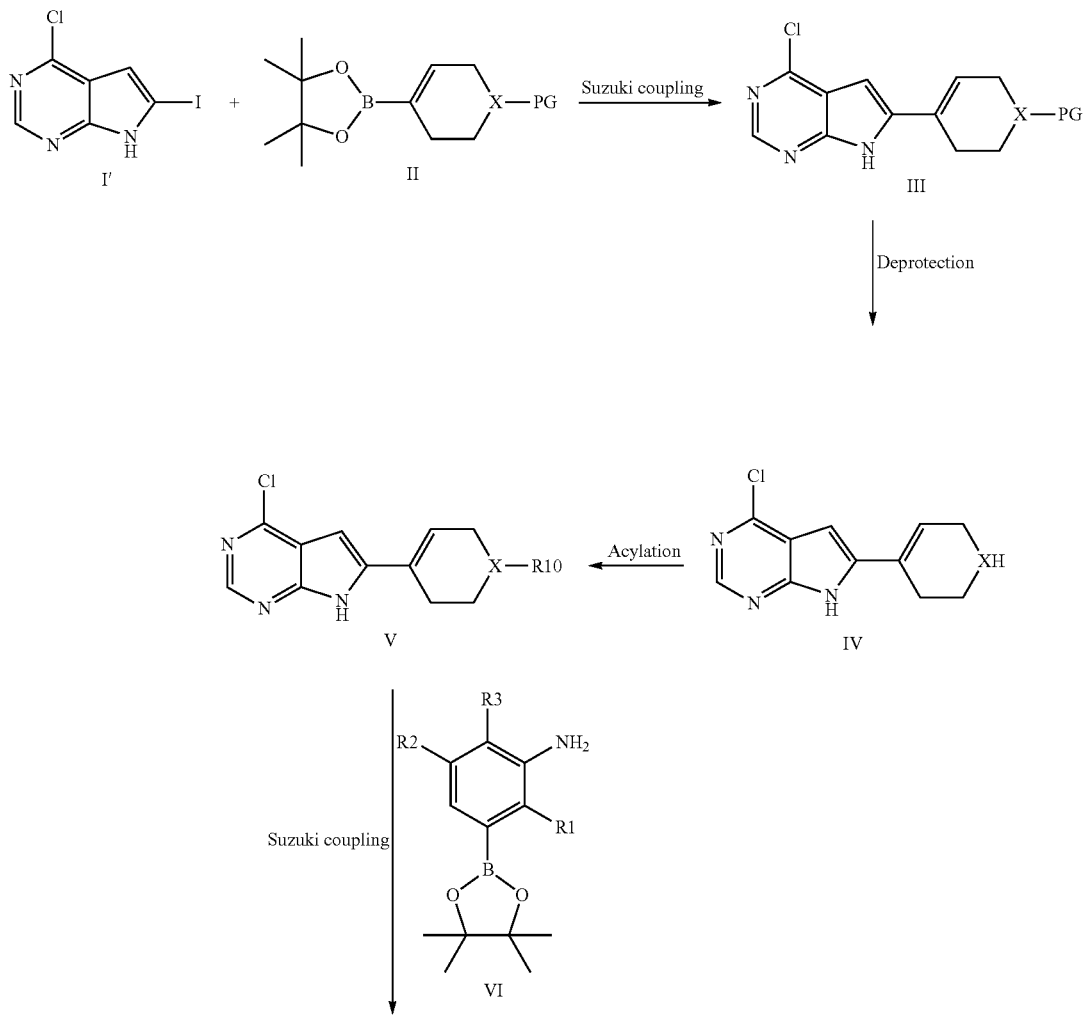

-continued

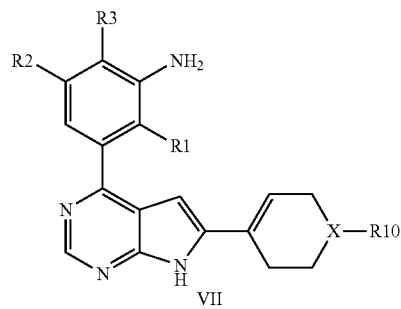

VII

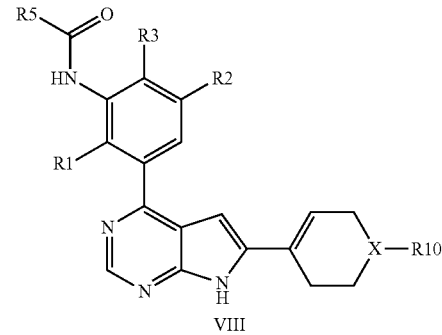

VIII

Alternatively, the compounds of formula (I) may also be prepared by a reaction sequence involving Suzuki coupling of boronic esters IX with the corresponding aryl halides I', followed by an additional Suzuki coupling of V with boronic esters VI and an acylation of VII (optionally followed by a deprotection step), as shown in Reaction Scheme 2 below:

Alternatively, the compounds of formula (I) may also be prepared by a reaction sequence involving Suzuki coupling of boronic esters VI with the corresponding aryl halides III, acylation of intermediate X, followed by deprotection of XI and acylation of XII (optionally followed by a deprotection step), as shown in Reaction Scheme 3 below, wherein X Reaction Scheme 2:

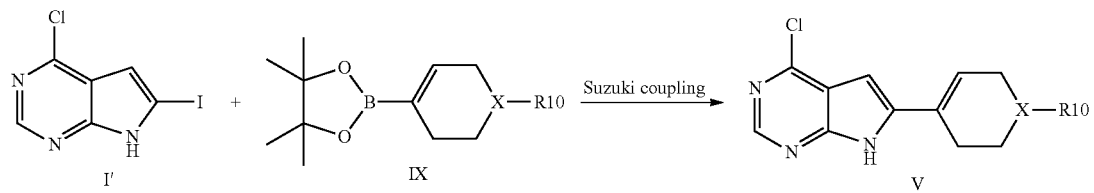

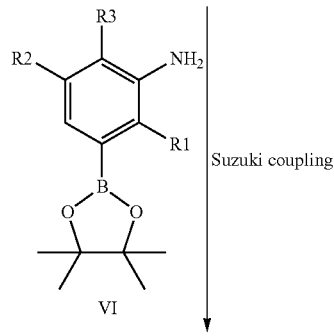

VI

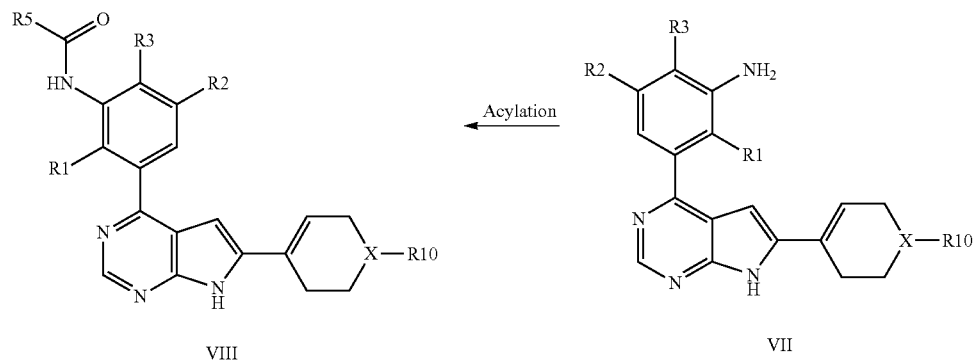

VIII                                                                                      VII denotes N, and the group PG refers to a protecting group that may be easily removed, such as for example, tert-butyloxy-carbonyl.
Reaction Scheme 3:
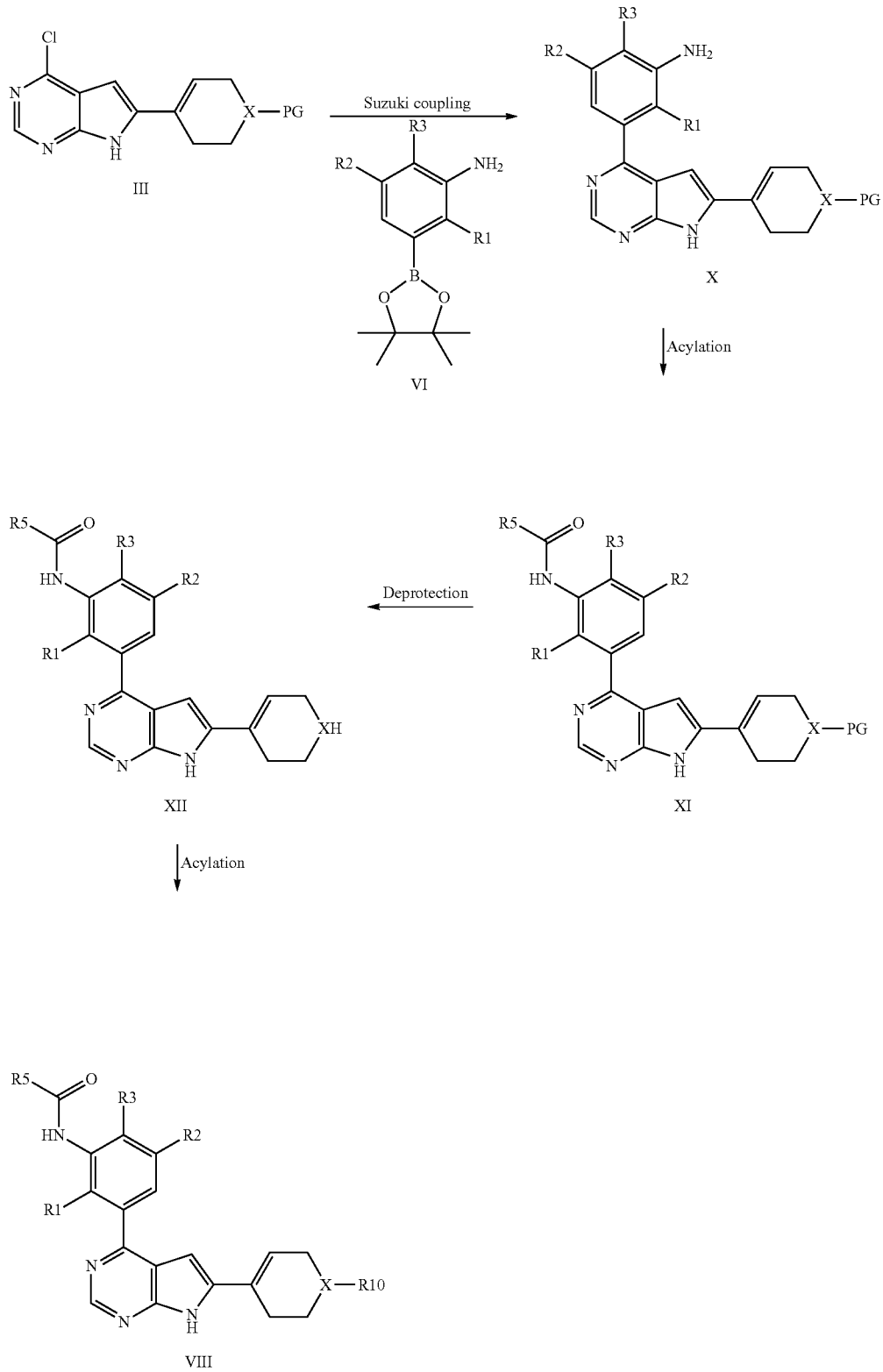

Alternatively, the compounds of formula (I) may also be prepared by a reaction sequence involving Suzuki coupling of boronic esters XIII with the corresponding aryl halides III, followed by deprotection of XI and acylation of XII (optionally followed by a deprotection step), as shown in Reaction Scheme 4 below, wherein X denotes N, and the group PG refers to a protecting group that may be easily removed, such as for example, tert-butyloxycarbonyl.

Reaction Scheme 4:

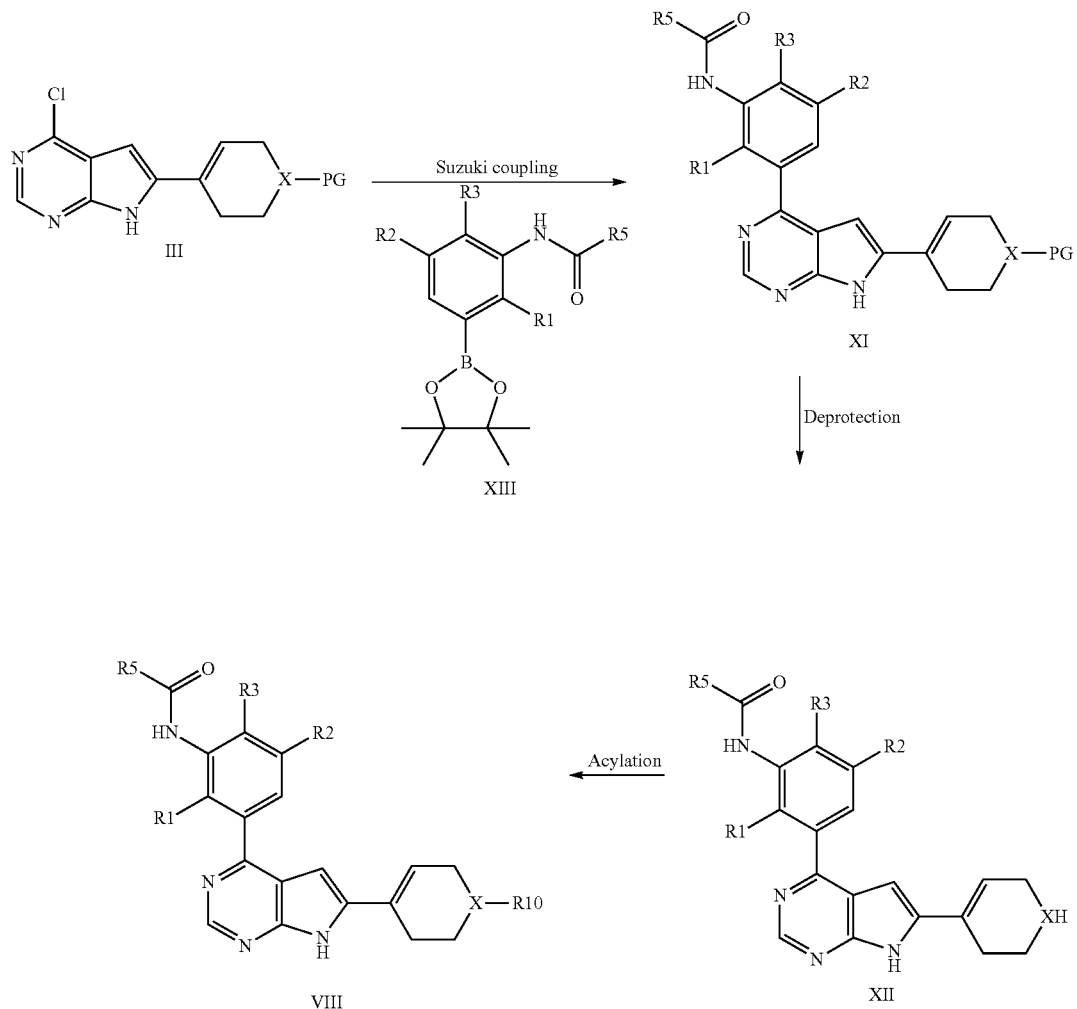

Alternatively, the compounds of formula (I) may also be prepared by a Suzuki coupling of boronic esters XIV with the corresponding aryl halides III (optionally followed by a deprotection step), as shown in Reaction Scheme 5 below:

Reaction Scheme 5:

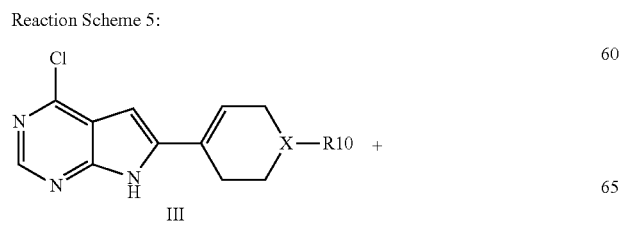

-continued

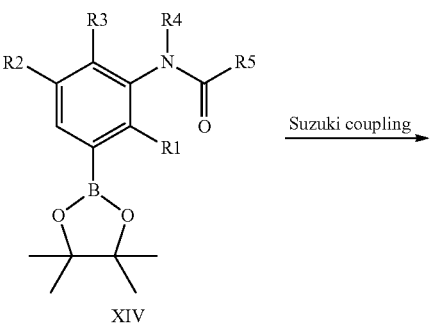

-continued

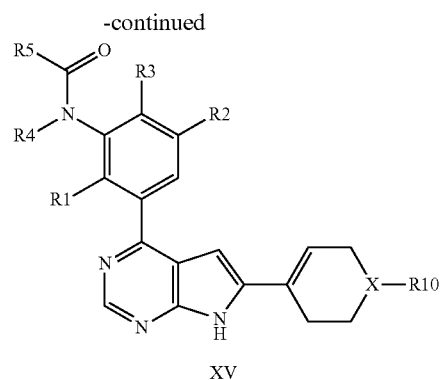
XV

Alternatively, the compounds of formula (I) may also be prepared by urea formation reaction of anilines VII (optionally followed by a deprotection step), as shown in Reaction Scheme 6 below:

Reaction Scheme 6:

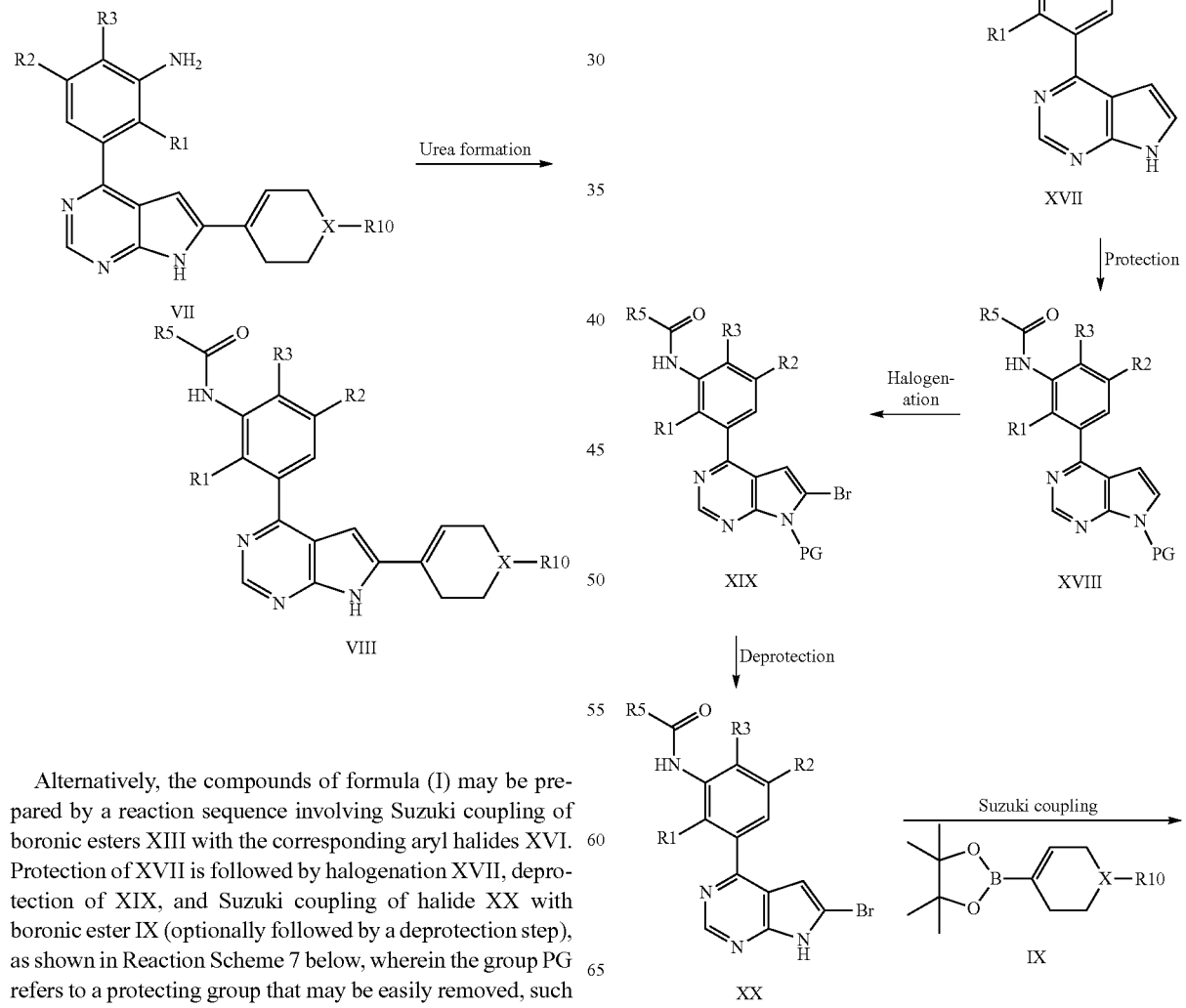

Alternatively, the compounds of formula (I) may be prepared by a reaction sequence involving Suzuki coupling of boronic esters XIII with the corresponding aryl halides XVI. Protection of XVII is followed by halogenation XVII, deprotection of XIX, and Suzuki coupling of halide XX with boronic ester IX (optionally followed by a deprotection step), as shown in Reaction Scheme 7 below, wherein the group PG refers to a protecting group that may be easily removed, such as for example, benzenesulfonyl.

Reaction Scheme 7:

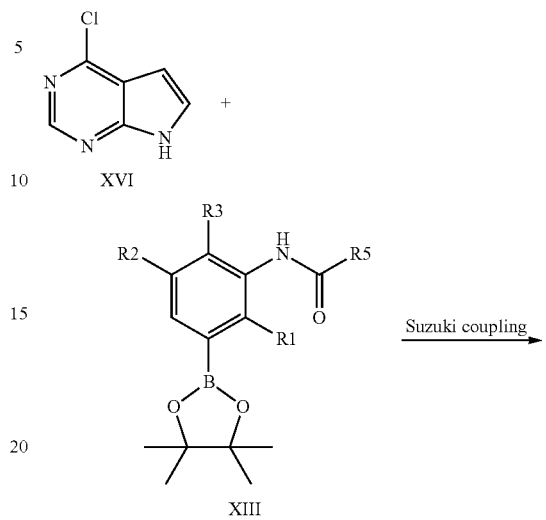

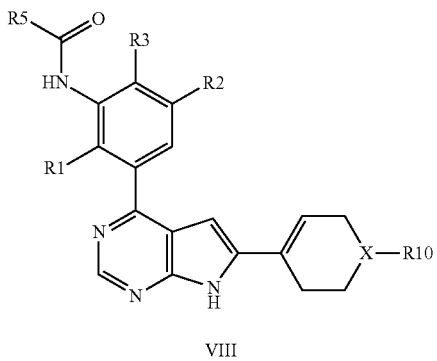

VIII

Synthesis of the Compound(s) of the Invention

EXPERIMENTAL SECTION

Abbreviations

AcOH Acetic acid
BOC tert-Butyloxycarbonyl
COMU: (1-Cyano-2-ethoxy-2-oxoethylidenaminooxy)dimethylamino-morpholino-carbenium hexafluorophosphate
$Cs_2CO_3$ Cesium carbonate
DCM: Dichloromethane
DIPEA: Ethyl-diisopropyl-amine, Hünig's base, DIEA
DMA: N,N-Dimethylacetamide
DMAP: Dimethyl-pyridin-4-yl-amine
DMF: N,N-Dimethyl formamide
DMSO: Dimethylsulfoxide
EtOAc: Acetic acid ethyl ester
EtOH: Ethanol
HATU: O-(7-Azabenzotriazol-1-yl)-N,N,N',N'-tetramethyluroniumhexafluorophosphat
hrs: Hours
LDA: Lithium diisopropyamide
MeCN: Acetonitrile
MeOH: Methanol
$NaBH_4$: Sodium borohydride
NaH sodium hydride
$Na_2SO_4$ Sodium sulfate
$NH_4OH$: Ammonia hydrogen solution 25%
Pd/C: Palladium on carbon
$Pd_2(dba)_3$: Tris(dibenzylideneacetone)dipalladium(O)
TEA: Triethylamine
TFA: Trifluoro-acetic acid
THF: Tetrahydrofuran
rt: Retention time
r.t. Room temperature
Xantphos: 4,5-Bis-diphenylphosphanyl-9,9-dimethyl-9H-xanthene

$^1$H-NMR spectra were recorded on a Bruker 600 MHz, a Bruker 500 MHz, or a Bruker 400 MHz NMR spectrometer. Significant peaks are tabulated in the order: multiplicity (s, singlet; d, doublet; t, triplet; q, quartet; m, multiplet; br, broad) and number of protons. Electron Spray Ionization (ESI) mass spectra were recorded on an Agilent 1100 Series mass spectrometer. Mass spectrometry results are reported as the ratio of mass over charge.

Detailed analytical HPLC chromatography methods referred to in the preparations and examples below are outlined as follows:

Preparative LC/MS Method 1:

Preparative Waters chromatography instrument equipped with a mircomass ZQ MS detector and Waters X bridge C18-ODB (5 μm) 30×150 mm column. Peak detection is reported at 210 nm wavelength.

Solvent A: Water containing 1 mM ammonium hydrogen carbonate

Solvent B: Acetonitrile containing 0.04% formic acid.

Flow rate at 50 ml/minute

| Gradient: | | |
| --- | --- | --- |
| Time [minutes] | Solvent A [%] | Solvent B [%] |
| 0 | 85 | 15 |
| 1 | 85 | 15 |
| 10 | 10 | 80 |
| 11 | 0 | 100 |
| 13.5 | 0 | 100 |

LC/MS Method 1:

Waters Acquity UPLC instrument equipped with diode array detector, Waters SQD Single Stage Quadrupole mass spectrometer and Waters Acquity HSS T3 (1.8 μm) 2.1×50 mm column. Peak detection is reported full scan 210-315 nm wavelength.

Column temperature 50 C.

Solvent A: Water containing 0.05% ammonium acetate and 0.05% formic acid.

Solvent B: Acetonitrile containing 0.04% formic acid.

Flow rate at 1.2 ml/minute

| Gradient: | | |
| --- | --- | --- |
| Time [minutes] | Solvent A [%] | Solvent B [%] |
| 0 | 98 | 2 |
| 1.40 | 2 | 98 |
| 2.15 | 2 | 98 |
| 2.19 | 98 | 2 |
| 2.20 | 98 | 2 |

Mass range: ESI +/−: 120-1200 m/z

All reagents, starting materials and intermediates utilized in these examples are available from commercial sources or are readily prepared by methods known to those skilled in the art.

Example 1

4-(4-{5-Fluoro-3-[4-(1-fluoro-cyclopropyl)-benzoylamino]-2-methyl-phenyl}-7H-pyrrolo[2'3-d]pyrimidin-6-yl)-3,6-dihydro-2H-pyridine-1-carboxylic acid dimethylamide

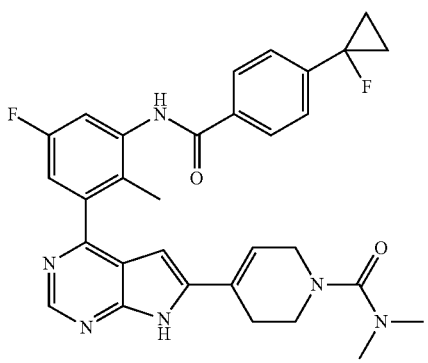 [SMILES: Cc1c(NC(=O)c2ccc(C3(F)CC3)cc2)cc(F)cc1-c1ncnc2[nH]c(C3=CCN(C(=O)N(C)C)CC3)cc12]

(1) 4-(4-Chloro-7H-pyrrolo[2,3-d]pyrimidin-6-yl)-3,6-dihydro-2H-pyridine-1-carboxylic acid tert-butyl ester, Intermediate 1

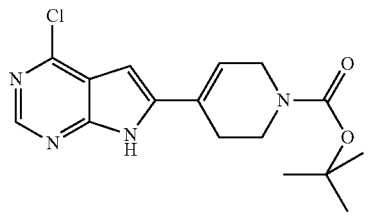 [SMILES: CC(C)(C)OC(=O)N1CC=C(c2cc3c(Cl)ncnc3[nH]2)CC1]

To a mixture of 4-chloro-6-iodo-7H-pyrrolo[2,3-d]pyrimidine (2.6 g, 9.30 mmol) and dichlorobis(triphenylphosphine)palladium (II) (0.52 g, 0.74 mmol) in 1-propanol (120 ml) and aqueous sodium carbonate solution (2M, 10.23 ml, 20.46 mmol), 4-(4,4,5,5-tetramethyl-[1,2,3]dioxaborolan-2-yl)-3,6-dihydro-2H-pyridine-1-carboxylic acid tert-butyl ester (3.02 g, 9.77 mmol) was added. The mixture was heated to 100° C. for 18 hours. After cooling the brownish mixture was diluted with 200 ml water and extracted with DCM. The organic layer was washed with brine (2×) and dried over sodium sulfate, than filtered and evaporated. The residue was purified by flash chromatography on silica (cyclohexane/EtOAc 1:1) to afford the compound Intermediate 1 as a beige solid.

MS (ESI): 335 [M+H]$^+$, $^1$H-NMR (DMSO-d$_6$): δ (ppm) 12.64 (br s, 1H), 8.56 (s, 1H), 6.59 (s, 2H), 4.08 (br s, 2H), 3.57 (m, 2H), 2.55 (m, 2H), 1.45 (s, 9H).

(2) 4-Chloro-6-(1,2,3,6-tetrahydro-pyridin-4-yl)-7H-pyrrolo[2,3-d]pyrimidine, Intermediate 2

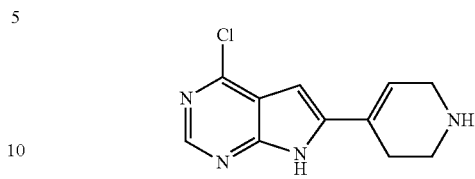

To a solution of compound Intermediate 1 (2.60 g, 7.77 mmol) in 10 ml DCM, 30 ml TFA/water 95:5 were added. The resulting mixture was stirred at room temperature for 2 hours. The mixture was diluted with water and basified by addition of 2N sodium hydroxide and extracted with DCM. The organic layer was washed with brine (2×), dried over sodium sulfate and evaporated. The residue was purified by flash chromatography on silica (cyclohexane/EtOAc 1:1 to EtOAc) to afford the compound Intermediate 2 as a beige solid.

MS (ESI): 235 [M+H]$^+$, $^1$H-NMR (DMSO-d$_6$): δ (ppm) 9.70 (br s, 2H), 8.56 (s, 1H), 6.58 (s, 1H), 6.55 (br s, 1H), 3.80 (m, 2H), 3.30 (m, 2H), 2.80 (m, 2H).

(3) 4-(4-Chloro-6-(1,2,3,6-tetrahydro-pyridin-4-yl)-7H-pyrrolo[2,3-d]pyrimidine, Intermediate 3

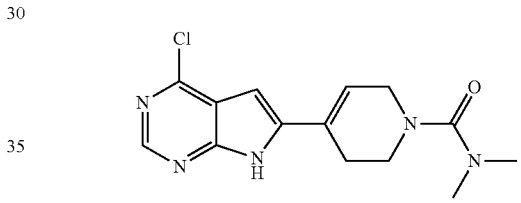

To a suspension of the amine Intermediate 2 (0.75 g, 3.20 mmol) in DCM (30 ml) and DIPEA (1.09 ml, 6.39 mmol), dimethylcarbamoylchloride (0.52 g, 4.79 mmol) was added. The mixture was stirred at room temperature for 20 hours. The solvents were evaporated under reduced pressure. The residue was purified by flash chromatography on silica (EtOAc to EtOAc/methanol/ammonia 95:5:0.5) to afford the compound Intermediate 3 as a beige solid.

MS (ESI): 306 [M+H]$^+$, $^1$H-NMR (DMSO-d$_6$): δ (ppm) 12.65 (s, 1H), 8.55 (s, 1H), 6.60 (s, 1H), 6.57 (s, 1H), 3.90 (m, 2H), 3.36 (m, 2H), 2.77 (s, 6H), 2.57 (m, 2H).

(4) 2-(Fluoro-2-methyl-3-nitro-phenyl)-4,4,5,5-tetramethyl-[1,3,2]dioxaborolone, Intermediate 4

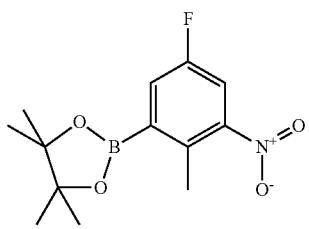 [SMILES: Cc1c(B2OC(C)(C)C(C)(C)O2)cc(F)cc1[N+](=O)[O-]]

To a mixture of 1-Bromo-5-fluoro-2-methyl-3-nitro-benzene (5.0 g, 21.37 mmol) and bis(diphenylphosphino)ferrocenedichloropalladium (II) (0.78 g, 1.06 mmol) in 200 ml dioxane, bis-(pinacolato)-diboron (8.14 g, 32.0 mmol) and potassium acetate (7.34 g, 74.8 mmol) were added. The mixture was heated to 100° C. for 6 hours. After cooling the brownish mixture was diluted with 200 ml water and extracted with EtOAc. The organic layer was washed with sodium hydrogen carbonate (1×) and brine (2×) and dried over sodium sulfate, then filtered and evaporated. The residue was purified by flash chromatography on silica (cyclohexane/EtOAc 9:1) to afford the compound Intermediate 4 as a yellow oil.

MS (ESI): 281 [M]$^+$, $^1$H-NMR (DMSO-d$_6$): δ (ppm) 7.79 (d, 1H), 7.55 (d, 1H), 2.48 (s, 3H), 1.31 (s, 12H).

(5) 5-Fluoro-2-methyl-3-(4,4,5,5-tetramethyl-[1,3,2]dioxaborolan-2-yl)-phenylamine, Intermediate 5

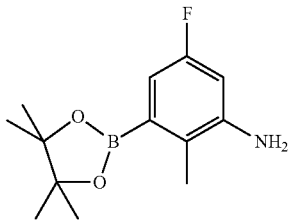 [SMILES: Cc1c(N)cc(F)cc1B1OC(C)(C)C(C)(C)O1]

The nitro compound Intermediate 4 (12.4 g, 44.1 mmol) was dissolved in 300 ml EtOAc and Pd/C 10% (Pd) (4.0 g) was added. The mixture was hydrogenated at room temperature and normal pressure for 18 hours. The mixture was filtered over Kieselgur (Supelco) and evaporated. The residue was purified by flash chromatography on silica (EtOAc) to afford the compound Intermediate 5 as a beige solid.

MS (ESI): 252 [M+H]$^+$, $^1$H-NMR (DMSO-d$_6$): δ (ppm) 6.52 (m, 2H), 5.11 (br s, 2NH), 2.19 (s, 3H), 1.29 (s, 12H).

(6) 4-[4-(3-Amino-5-fluoro-2-methyl-phenyl)-7H-pyrrolo[2,3-d]pyrimidin-6-yl]-3,6-dihydro-2H-pyridine-1-carboxylic acid dimethylamide, Intermediate 6

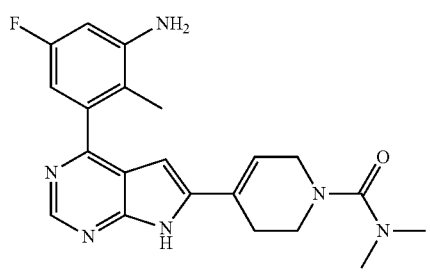 [SMILES: Cc1c(N)cc(F)cc1-c1ncnc2[nH]c(C3=CCN(C(=O)N(C)C)CC3)cc12]

To a mixture of chloro compound Intermediate 3 (3.94 g, 15.70 mmol) and dichlorobis(triphenylphosphine)palladium (II) (0.73 g, 1.04 mmol) in 1-propanol (150 ml) and aqueous sodium carbonate solution (2M, 6.54 ml, 13.08 mmol), boronic ester compound Intermediate 5 (4.0 g, 13.08 mmol) was added. The mixture was heated at 100° C. for 16 hours. After cooling the brownish mixture was diluted with 200 ml water and extracted with EtOAc. The organic layer was washed with brine (2×) and dried over sodium sulfate, than filtered and evaporated. The residue was purified by flash chromatography on silica (EtOAc/methanol/ammonia 98:2:0.2 to EtOAc/MeOH/NH4OH 9:1:0.1) to afford the compound Intermediate 6 as a beige solid.

MS (ESI): 395 [M+H]$^+$, $^1$H-NMR (DMSO-d$_6$): δ (ppm) 11.80 (br s, 1H), 8.87 (s, 1H), 6.70 (m, 1H), 6.55 (m, 1H), 6.48 (br s, 1H), 6.38 (br s, 1H), 4.05 (br s, 2H), 3.90 (br s, 2NH), 3.55 (m, 2H), 2.90 (s, 6H), 2.65 (m, 2H), 2.10 (s, 3H).

(7) 4-(4-{5-Fluoro-3-[4-(1-fluoro-cyclopropyl)-benzoylamino]-2-methyl-phenyl}-7H-pyrrolo[2'3-d]pyrimidin-6-yl)-3,6-dihydro-2H-pyridine-1-carboxylic acid dimethylamide

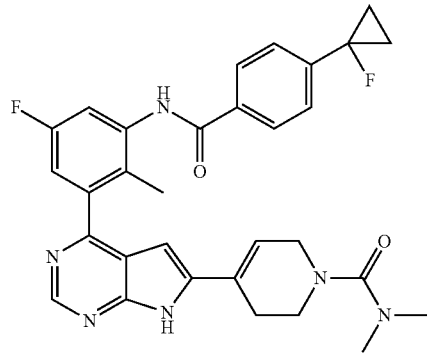 [SMILES: Cc1c(NC(=O)c2ccc(C3(F)CC3)cc2)cc(F)cc1-c1ncnc2[nH]c(C3=CCN(C(=O)N(C)C)CC3)cc12]

Anilino compound Intermediate 6 (80 mg, 0.203 mmol), 4-(1-fluoro-cyclopropyl)-benzoic acid (for preparation see WO 07/090752) (40 mg, 0.223 mmol) and COMU (130 mg, 0.304 mmol) were dissolved in DIPEA (0.071 ml, 0.406 mmol) and DMA (1.0 ml). The solution was stirred at room temperature for 18 hrs. The reaction was diluted with 10 ml EtOAc and extracted with water by a Hamilton extractor. The water layer was extracted with EtOAc (5×). The combined organic layers were dried with sodium sulfate and evaporated. The residue was purified by a preparative LC/MS method 1 to afford the compound Example 1 as a beige solid.

MS (ESI): 557 [M+H]$^+$, $^1$H-NMR (DMSO-d$_6$): δ (ppm) 12.43 (br s, 1H), 10.07 (s, 1H), 8.83 (s, 1H), 8.03 (d, 2H), 7.49 (m, 1H), 7.43 (d, 2H), 7.23 (m, 1H), 6.59 (br s, 1H), 6.33 (s, 1H), 3.90 (m, 2H), 3.33 (m, 2H), 2.77 (s, 6H), 2.54 (m, 2H), 2.12 (s, 3H), 1.55 (m, 2H), 1.26 (m, 2H).

The following Examples 2-14 were prepared as outlined in Reaction Scheme 1 and described for Example 1 using the intermediate Intermediate 6 and the appropriate benzoic acid as starting materials.

Example 2

4-(4-{3-[(3,3-Dimethyl-2,3-dihydro-benzofuran-6-carbonyl)-amino]-5-fluoro-2-methyl-phenyl}-7H-pyrrolo[2'3-d]pyrimidin-6-yl)-3,6-dihydro-2H-pyridine-1-carboxylic acid dimethylamide

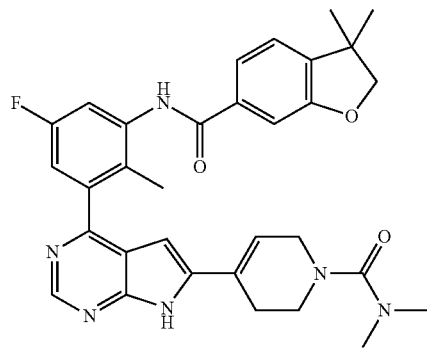 [SMILES: Cc1c(NC(=O)c2ccc3c(c2)OCC3(C)C)cc(F)cc1-c1ncnc2[nH]c(C3=CCN(C(=O)N(C)C)CC3)cc12]

LC/MS (Method 1): rt: 1.01 minutes, MS (ESI): 569 [M+H]+

Example 3

4-(4-{5-Fluoro-2-methyl-3-[(5-methyl-4,5,6,7-tetrahydro-benzo[b]thiophene-2-carbonyl)-amino]-phenyl}-7H-pyrrolo[2'3-d]pyrimidin-6-yl)-3,6-dihydro-2H-pyridine-1-carboxylic acid dimethylamide

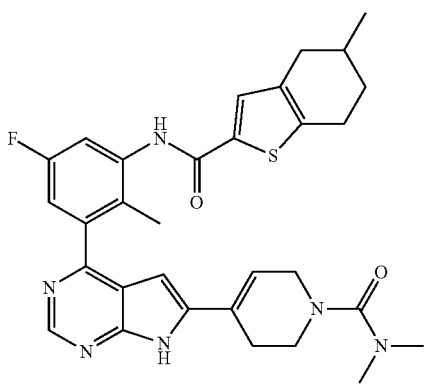 [SMILES: Cc1c(NC(=O)c2cc3c(s2)CCC(C)C3)cc(F)cc1-c1ncnc2[nH]c(C3=CCN(C(=O)N(C)C)CC3)cc12]

LC/MS (Method 1): rt: 1.14 minutes, MS (ESI): 573 [M+H]+

Example 4

4-(4-{5-Fluoro-3-[4-isopropyl-methyl-amino)-benzoylamino]-2-methyl-phenyl}-7H-pyrrolo[2'3-d]pyrimidin-6-yl)-3,6-dihydro-2H-pyridine-1-carboxylic acid dimethylamide

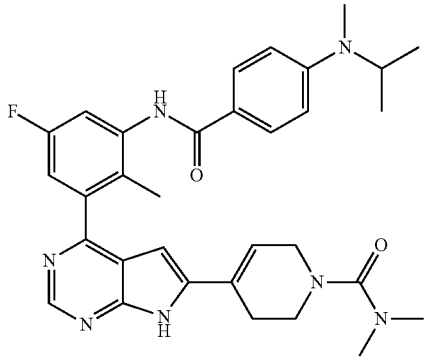 [SMILES: Cc1c(NC(=O)c2ccc(N(C)C(C)C)cc2)cc(F)cc1-c1ncnc2[nH]c(C3=CCN(C(=O)N(C)C)CC3)cc12]

LC/MS (Method 1): rt: 1.05 minutes, MS (ESI): 570 [M+H]+

Example 5

3-Methyl-1H-indole-6-carboxylic acid {3-[6-(1-dimethylcarbamoyl-1,2,3,6-tetrahydro-pyridin-4-yl)-7H-pyrrolo[2,3-d]pyrimidin-4-yl]-5-fluoro-2-methyl-phenyl}-amide

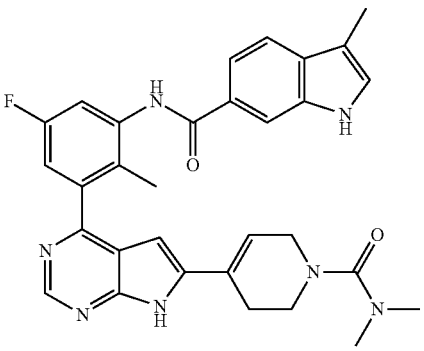 [SMILES: Cc1c(NC(=O)c2ccc3c(C)c[nH]c3c2)cc(F)cc1-c1ncnc2[nH]c(C3=CCN(C(=O)N(C)C)CC3)cc12]

LC/MS (Method 1): rt: 0.95 minutes, MS (ESI): 552 [M+H]+

Example 6

4-(4-{5-Fluoro-3-[4-(2-hydroxy-1,1-dimethyl-ethyl)-benzoylamino]-2-methyl-phenyl}-7H-pyrrolo[2,3-d]pyrimidin-6-yl)-3,6-dihydro-2H-pyridine-1-carboxylic acid dimethylamide

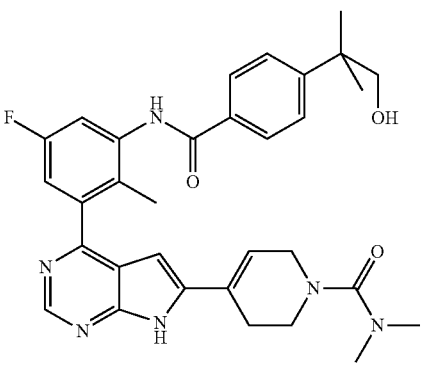 [SMILES: Cc1c(NC(=O)c2ccc(C(C)(C)CO)cc2)cc(F)cc1-c1ncnc2[nH]c(C3=CCN(C(=O)N(C)C)CC3)cc12]

LC/MS (Method 1): rt: 0.88 minutes, MS (ESI): 571 [M+H]+

Example 7

4-{4-[5-Fluoro-2-methyl-3-(4-piperidin-1-yl-benzoylamino)-phenyl]-7H-pyrrolo[2,3-d]pyrimidin-6-yl}-3,6-dihydro-2H-pyridine-1-carboxylic acid dimethylamide

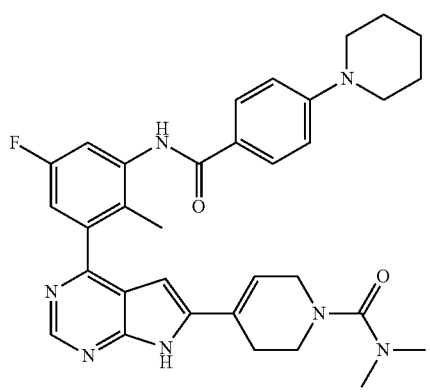 [SMILES: Cc1c(NC(=O)c2ccc(N3CCCCC3)cc2)cc(F)cc1-c1ncnc2[nH]c(C3=CCN(C(=O)N(C)C)CC3)cc12]

LC/MS (Method 1): rt: 1.07 minutes, MS (ESI): 582 [M+1-1]$^+$

Example 8

4-{4-[5-Fluoro-3-(isopropenyl-benzoylamino)-2-methyl-phenyl]-7H-pyrrolo[2,3-d]pyrimidin-6-yl}-3,6-dihydro-2H-pyridine-1-carboxylic acid dimethylamide

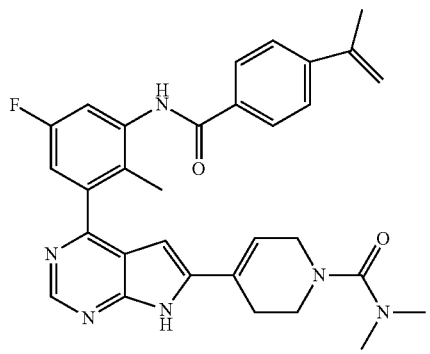 [SMILES: C=C(C)c1ccc(C(=O)Nc2cc(F)cc(-c3ncnc4[nH]c(C5=CCN(C(=O)N(C)C)CC5)cc34)c2C)cc1]

LC/MS (Method 1): rt: 1.04 minutes, MS (ESI): 539 [M+1-1]+

Example 9

4-(4-{5-Fluoro-2-methyl-3-[4-(1-trifluoromethyl-cyclopropyl)-benzoylamino]-phenyl}-7H-pyrrolo[2,3-d]pyrimidin-6-yl)-3,6-dihydro-2H-pyridine-1-carboxylic acid dimethylamide

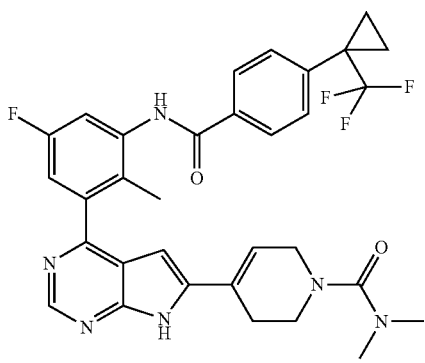 [SMILES: Cc1c(NC(=O)c2ccc(C3(C(F)(F)F)CC3)cc2)cc(F)cc1-c1ncnc2[nH]c(C3=CCN(C(=O)N(C)C)CC3)cc12]

LC/MS (Method 1): rt: 1.08 minutes, MS (ESI): 607 [M+1-1]$^+$

Example 10

4-{4-[5-Fluoro-3-(4-isopropoxy-benzoylamino)-2-methyl-phenyl]-7H-pyrrolo[2,3-d]pyrimidin-6-yl}-3,6-dihydro-2H-pyridine-1-carboxylic acid dimethylamide

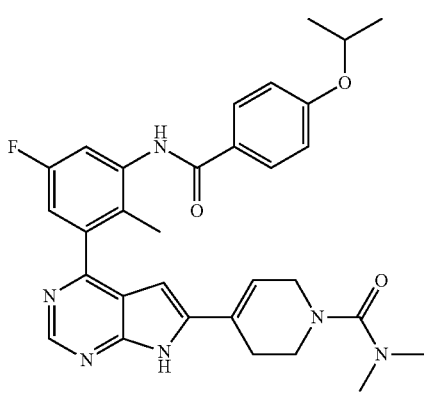 [SMILES: Cc1c(NC(=O)c2ccc(OC(C)C)cc2)cc(F)cc1-c1ncnc2[nH]c(C3=CCN(C(=O)N(C)C)CC3)cc12]

LC/MS (Method 1): rt: 1.04 minutes, MS (ESI): 557 [M+H]$^+$

Example 11

4-(4-{5-Fluoro-3-[4-pentafluorothio-benzoylamino]-2-methyl-phenyl}-7H-pyrrolo[2,3-d]pyrimidin-6-yl)-3,6-dihydro-2H-pyridine-1-carboxylic acid dimethylamide

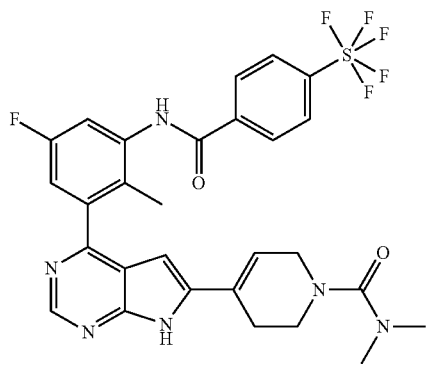 [SMILES: Cc1c(NC(=O)c2ccc(S(F)(F)(F)(F)F)cc2)cc(F)cc1-c1ncnc2[nH]c(C3=CCN(C(=O)N(C)C)CC3)cc12]

LC/MS (Method 1): rt: 1.07 minutes, MS (ESI): 625 [M+H]$^+$

Example 12

4-(4-{5-Fluoro-3-[4-(2-methoxy-1,1-dimethyl-ethyl)-benzoylamino]-2-methyl-phenyl}-7H-pyrrolo[2,3-d]pyrimidin-6-yl)-3,6-dihydro-2H-pyridine-1-carboxylic acid dimethylamide

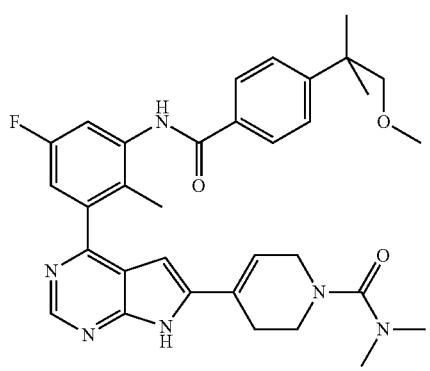 [SMILES: COCC(C)(C)c1ccc(C(=O)Nc2cc(F)cc(-c3ncnc4[nH]c(C5=CCN(C(=O)N(C)C)CC5)cc34)c2C)cc1]

LC/MS (Method 1): rt: 1.04 minutes, MS (ESI): 585 [M+H]$^+$

Example 13

4-(4-{5-Fluoro-3-[4-(1-methoxy-1-methyl-ethyl)-benzoylamino]-2-methyl-phenyl}-7H-pyrrolo[2,3-d]pyrimidin-6-yl)-3,6-dihydro-2H-pyridine-1-carboxylic acid dimethylamide

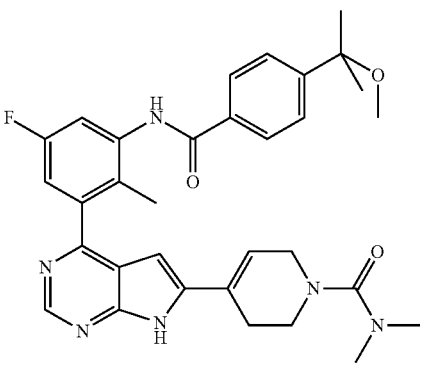 [SMILES: COC(C)(C)c1ccc(C(=O)Nc2cc(F)cc(-c3ncnc4[nH]c(C5=CCN(C(=O)N(C)C)CC5)cc34)c2C)cc1]

LC/MS (Method 1): rt: 0.98 minutes, MS (ESI): 571 [M+H]$^+$

Example 14

1-Methyl-1H-pyrrolo[2,3-b]pyridine-6-carboxylic acid {3-[6-(1-dimethyl-carbamoyl-1,2,3,6-tetrahydro-pyridin-4-yl)-7H-pyrrolo[2,3-d]pyrimidin-4-yl]-5-fluoro-2-methyl-phenyl}-amide

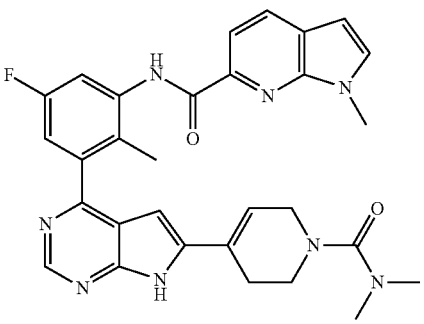 [SMILES: Cc1c(NC(=O)c2ccc3ccn(C)c3n2)cc(F)cc1-c1ncnc2[nH]c(C3=CCN(C(=O)N(C)C)CC3)cc12]

LC/MS (Method 1): rt: 0.85 minutes, MS (ESI): 553 [M+H]$^+$

Example 15

4-{4-[3-(4-Dimethylamino-benzoylamino)-5-fluoro-2-methyl-phenyl]-7H-pyrrolo[2,3-d]pyrimidin-6-yl}-3,6-dihydro-2H-pyridine-1-carboxylic acid dimethylamide

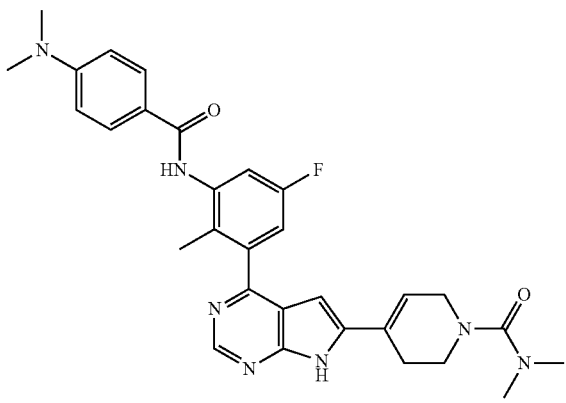

To a solution of aniline Intermediate 6 (84 mg, 0.213 mmol) in DCM/pyridine (2:1, 30 ml) were added DIPEA (0.372 ml, 2.13 mmol), 4-dimethylaminobenzoyl chloride (43 mg, 0.234 mmol), and DMAP (2.6 mg, 0.021 mmol). The resulting mixture was stirred at room temperature for 75 hrs. The solvents were removed in vacuo and the resulting mixture was purified by reversed phase HPLC (MeCN/H$_2$O) to afford Example 15.

MS (ESI): 542 [M+H]$^+$, $^1$H-NMR (DMSO-d$_6$): δ (ppm) 12.41 (br s, 1H), 9.63 (s, 1H), 8.81 (s, 1H), 7.88 (d, 2H), 7.48 (m, 1H), 7.16 (m, 1H), 6.77 (d, 2H), 6.58 (br s, 1H), 6.32 (s, 1H), 3.89 (br s, 2H), 3.32 (m, 2H), 3.00 (s, 6H), 2.76 (s, 6H), 2.54 (m, 2H), 2.10 (s, 3H).

Example 16

4-(4-{3-[2-Fluoro-4-(1-hydroxy-1-methyl-ethyl)-benzoylamino]-2-hydroxymethyl-phenyl}-7H-pyrrolo[2,3-d]pyrimidin-6-yl)-3,6-dihydro-2H-pyridine-1-carboxylic acid dimethylamide

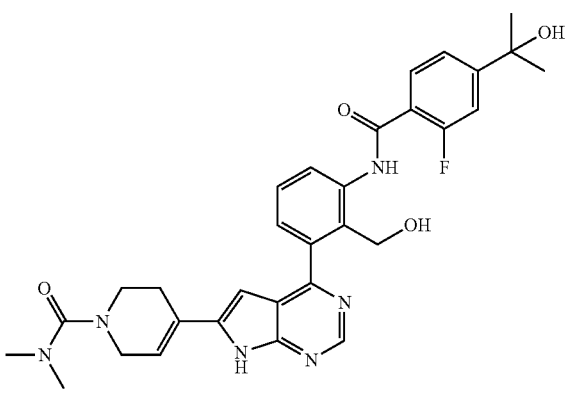 [SMILES: CN(C)C(=O)N1CC=C(c2cc3c(-c4cccc(NC(=O)c5ccc(C(C)(C)O)cc5F)c4CO)ncnc3[nH]2)CC1]

(1) 4-{4-[3-Amino-2-(tert-butyl-diphenyl-silanyloxymethyl)-phenyl]-7H-pyrrolo[2,3-d]pyrimidin-6-yl}-3,6-dihydro-2H-pyridine-1-carboxylic acid dimethylamide, Intermediate

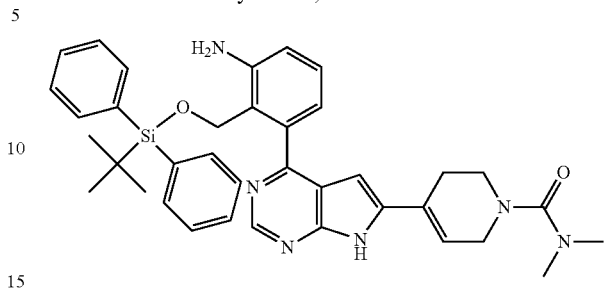

Intermediate 7 was prepared analogue to Intermediate 6 by replacing the boronic ester Intermediate 5 with the boronic ester Intermediate 27.

MS (ESI): 631 [M+H]$^+$, $^1$H-NMR (DMSO-d$_6$): δ (ppm) 12.24 (br s, 1H), 8.52 (s, 1H), 7.32 (m, 2H), 7.28-7.27 (m, 4H), 716-7.15 (m, 5H), 6.90 (d, 1H), 6.71 (d, 1H), 6.53 (m, 1H), 6.16 (s, 1H), 5.28 (br s, 2H), 4.82 (s, 2H), 3.88 (m, 6H), 3.31 (m, 2H), 2.75 (s, 6H), 2.44 (m, 2H), 0.81 (s, 9H).

(2) 2-Fluoro-4-(1-hydroxy-1-methyl-ethyl)-benzoic acid, Intermediate 8

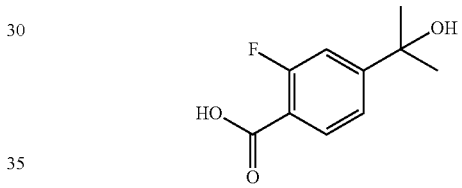

Intermediate 8 was prepared analogue to Intermediate 35 by replacing Intermediate 34 with 2-fluoro-terephthalic acid 4-methyl ester (J. Med. Chem., 52(19), 5950-5966; 2009).

MS (ESI): 197 [M−H]$^−$, $^1$H-NMR (DMSO-d$_6$): δ (ppm) 7.80 (t, 1H), 7.35 (m, 1H), 7.32 (m, 1H), 5.27 (br s, 1H), 1.42 (s, 6H).

(3) 4-(4-{2-(tert-Butyl-diphenyl-silanyloxymethyl)-3-[2-fluoro-4-(1-hydroxy-1-methyl-ethyl)-benzoylamino]-phenyl}-7H-pyrrolo[2,3-d]pyrimidin-6-yl)-3,6-dihydro-2H-pyridine-1-carboxylic acid dimethylamide, Intermediate 9

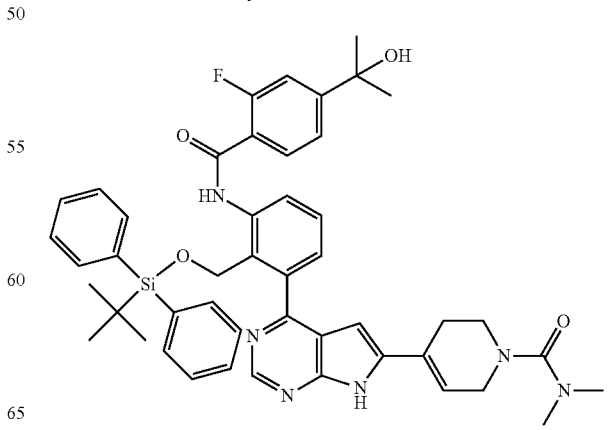

To a mixture of Intermediate 7 (58 mg, 0.091 mmol), Intermediate 8 (27 mg, 0.137 mmol), and DIPEA (0.059 ml, 0.337 mmol) in DMF (10 ml) was added HATU (38 mg, 0.100 mmol). The resulting mixture was stirred at r.t. for 22 hrs. The mixture was diluted with EtOAc and sat. NaHCO3 solution. The organic layer was washed with brine and dried over Na2SO$_4$. The solvents were removed in vacuo, and the crude product was purified by reversed phase HPLC (H$_2$O/MeCN) to afford Intermediate 9.

(4) 4-(4-{3-[2-Fluoro-4-(1-hydroxy-1-methyl-ethyl)-benzoylamino]-2-hydroxymethyl-phenyl}-7H-pyrrolo[2,3-d]pyrimidin-6-yl)-3,6-dihydro-2H-pyridine-1-carboxylic acid dimethylamide

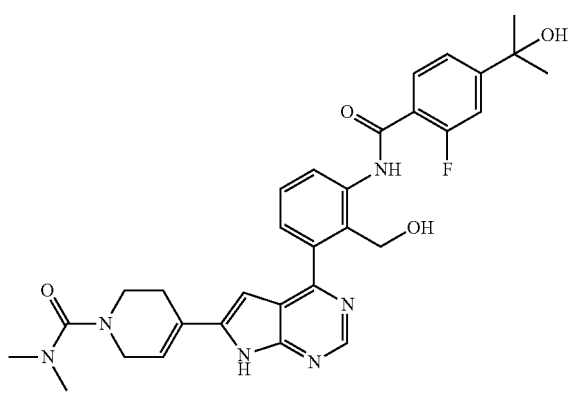 [SMILES: CN(C)C(=O)N1CC=C(c2cc3c(-c4cccc(NC(=O)c5ccc(C(C)(C)O)cc5F)c4CO)ncnc3[nH]2)CC1]

Example 16 was prepared analogue to Example 37 step 8 by replacing Intermediate 31 with Intermediate 9.
LC/MS (Method 1): rt: 1.94 minutes, MS (ESI): 573 [M+H]$^+$

Example 17

4-{4-[3-(4-Cyclopropyl-benzoylamino)-2-hydroxymethyl-phenyl]-7H-pyrrolo[2,3-d]pyrimidin-6-yl}-3,6-dihydro-2H-pyridine-1-carboxylic acid dimethylamide

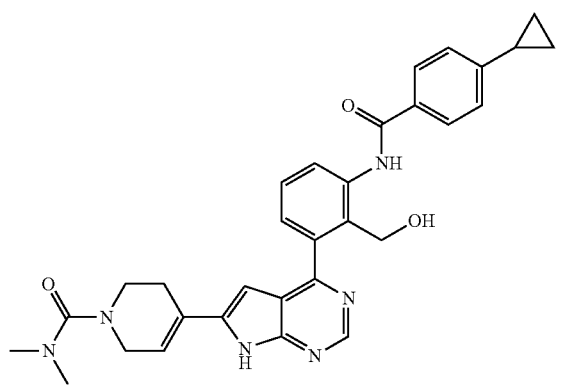 [SMILES: CN(C)C(=O)N1CC=C(c2cc3c(-c4cccc(NC(=O)c5ccc(C6CC6)cc5)c4CO)ncnc3[nH]2)CC1]

Example 17 was prepared analogue to Example 16 by replacing Intermediate 8 in step 3 with 4-cyclopropylbenzoic acid. LC/MS (Method 1): rt: 2.32 minutes, MS (ESI): 537 [M+H]$^+$

Example 18

4-(4-{5-Fluoro-2-methyl-3-[4-(2,2,2-trifluoro-1-hydroxy-1-methyl-ethyl)-benzoylamino]-phenyl}-7H-pyrrolo[2,3-d]pyrimidin-6-yl)-3,6-dihydro-2H-pyridine-1-carboxylic acid dimethylamide

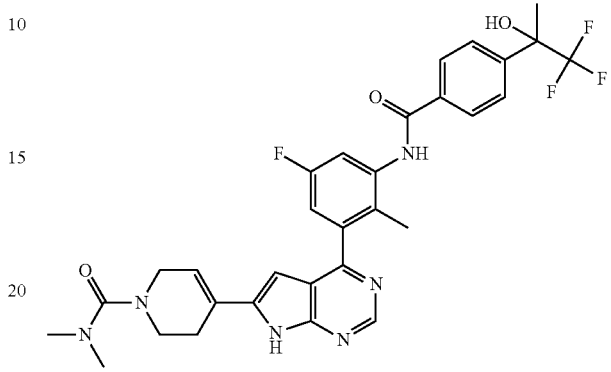

Example 18 was prepared analogue to Intermediate 9 by replacing Intermediate 7 with Intermediate 6 and Intermediate 8 with 4-(2,2,2-trifluoro-1-hydroxy-1-methyl-ethyl)-benzoic acid (WO2007/145834).
MS (ESI): 611 [M+H]$^+$, $^1$H-NMR (DMSO-d$_6$): δ (ppm) 12.43 (br s, 1H), 10.10 (s, 1H), 8.83 (s, 1H), 8.03 (d, 2H), 7.77 (d, 2H), 7.49 (m, 1H), 7.22 (m, 1H), 6.77 (s, 1H), 6.60 (br s, 1H), 6.34 (s, 1H), 3.90 (m, 2H), 3.35 (m, 2H), 2.77 (s, 6H), 2.55 (m, 2H), 2.10 (s, 3H), 1.75 (s, 3H).

Example 19

4-{4-[3-(4-Acetyl-benzoylamino)-5-fluoro-2-methyl-phenyl]-7H-pyrrolo[2,3-d]pyrimidin-6-yl}-3,6-dihydro-2H-pyridine-1-carboxylic acid dimethylamide

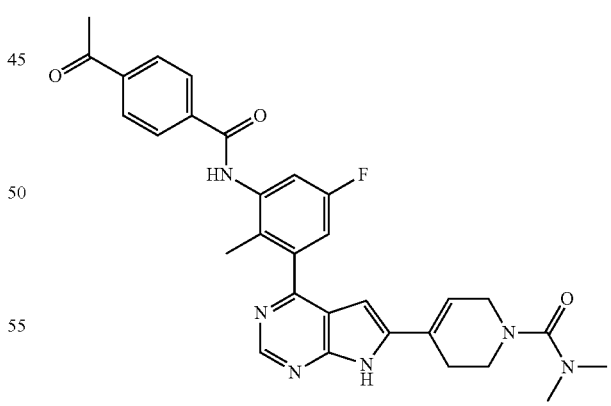

Example 19 was prepared analogue to Example 18 by replacing 4-(2,2,2-trifluoro-1-hydroxy-1-methyl-ethyl)-benzoic acid with 4-acetyl-benzoic acid.
MS (ESI): 541 [M+H]$^+$, $^1$H-NMR (DMSO-d$_6$): δ (ppm) 12.42 (br s, 1H), 10.24 (s, 1H), 8.82 (s, 1H), 8.11 (m, 4H), 7.48 (m, 1H), 7.24 (m, 1H), 6.59 (s, 1H), 6.33 (s, 1H), 3.89 (m, 2H), 3.34 (m, 2H), 2.76 (s, 6H), 2.65 (s, 3H), 2.53 (m, 2H), 2.13 (s, 3H).

Example 20

4-{4-[3-(4-Cyclopropyl-benzoylamino)-4-fluoro-phenyl]-7H-pyrrolo[2,3-d]pyrimidin-6-yl}-3,6-dihydro-2H-pyridine-1-carboxylic acid dimethylamide

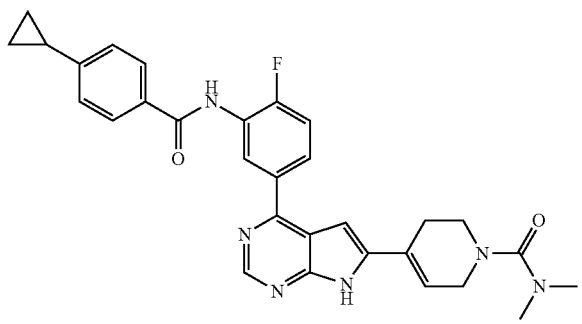 [SMILES: CN(C)C(=O)N1CC=C(c2cc3c(-c4ccc(F)c(NC(=O)c5ccc(C6CC6)cc5)c4)ncnc3[nH]2)CC1]

(1) 4-[4-(3-Amino-4-fluoro-phenyl)-7H-pyrrolo[2,3-d]pyrimidin-6-yl]-3,6-dihydro-2H-pyridine-1-carboxylic acid dimethylamide, Intermediate 10

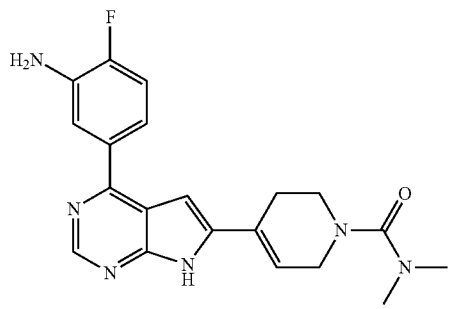 [SMILES: CN(C)C(=O)N1CC=C(c2cc3c(-c4ccc(F)c(N)c4)ncnc3[nH]2)CC1]

Intermediate 10 was prepared analogue to Intermediate 6 by replacing Intermediate 5 with 3-amino-4-fluoroboronic acid.

MS (ESI): 381 [M+H]$^+$, $^1$H-NMR (DMSO-d$_6$): δ (ppm) 12.32 (br s, 1H), 8.74 (s, 1H), 7.68 (m, 1H), 7.39 (m, 1H), 7.13 (m, 1H), 6.84 (s, 1H), 6.58 (s, 1H), 5.36 (br s, 2H), 3.91 (s, 2H), 3.37 (m, 2H), 2.77 (s, 6H), 2.62 (m, 2H).

(2) 4-{4-[3-(4-Cyclopropyl-benzoylamino)-4-fluoro-phenyl]-7H-pyrrolo[2,3-d]pyrimidin-6-yl}-3,6-dihydro-2H-pyridine-1-carboxylic acid dimethylamide

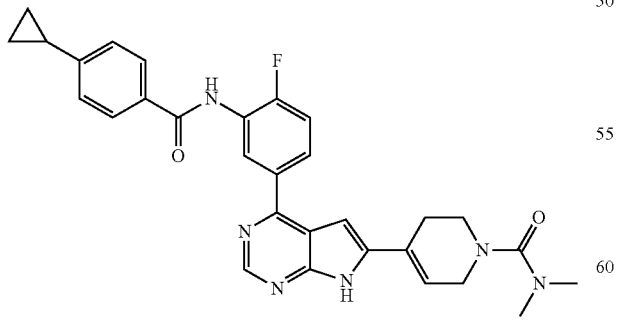

A mixture of Intermediate 10 (80 mg, 0.210 mmol), 4-cyclopropyl-benzoyl chloride (J. Med. Chem., 52(14), 4329-4337; 2009) (76 mg, 0.421 mmol), and DMAP (2.6 mg, 0.021 mmol) in pyridine (2 ml) was stirred at r.t. overnight. The mixture was evaporated to dryness, then sat. aqueous NaHCO$_3$ was added, and the mixture was extracted with DCM. The organic layer was dried, filtered, and evaporated to dryness. The residue was purified by flash chromatography (silica gel, EtOAc/MeOH/NH$_3$ gradient) to obtain Example 20.

MS (ESI): 525 [M+H]$^+$, $^1$H-NMR (DMSO-d$_6$): δ (ppm) 12.44 (br s, 1H), 10.20 (s, 1H), 8.80 (s, 1H), 8.47 (d, 1H), 8.09 (m, 1H), 7.92 (d, 2H), 7.49 (t, 1H), 7.25 (d, 1H), 6.93 (s, 1H), 6.60 (s, 1H), 3.91 (m, 2H), 3.35 (m, 2H), 2.77 (s, 6H), 2.62 (m, 2H), 2.02 (m, 1H), 1.04 (m, 2H), 0.78 (m, 2H).

Example 21

4-(4-{4-Fluoro-3-[4-(2-hydroxy-1,1-dimethyl-ethyl)-benzoylamino]-phenyl}-7H-pyrrolo[2,3-d]pyrimidin-6-yl)-3,6-dihydro-2H-pyridine-1-carboxylic acid dimethylamide

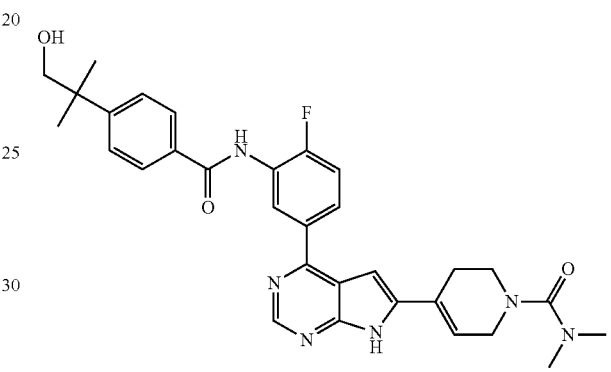

Example 21 was prepared analogue to Intermediate 9 by replacing Intermediate 7 with Intermediate 10 and Intermediate 8 with 4-(2-hydroxy-1,1-dimethyl-ethyl)-benzoic acid.

MS (ESI): 557 [M+H]$^+$, $^1$H-NMR (DMSO-d$_6$): δ (ppm) 12.41 (br s, 1H), 10.21 (s, 1H), 8.80 (s, 1H), 8.50 (m, 1H), 8.10 (m, 1H), 7.94 (d, 2H), 7.54 (d, 2H), 7.48 (m, 1H), 6.93 (s, 1H), 6.60 (s, 1H), 4.74 (br s, 1H), 3.91 (m, 2H), 3.48 (m, 2H), 3.34 (m, 2H), 2.77 (s, 6H), 2.62 (m, 2H). 1.27 (s, 6H).

Example 22

N-{3-[6-(3,6-Dihydro-2H-pyran-4-yl)-7H-pyrrolo[2,3-d]pyrimidin-4-yl]-5-fluoro-2-methyl-phenyl}-2-fluoro-4-(1-hydroxy-1-methyl-ethyl)-benzamide

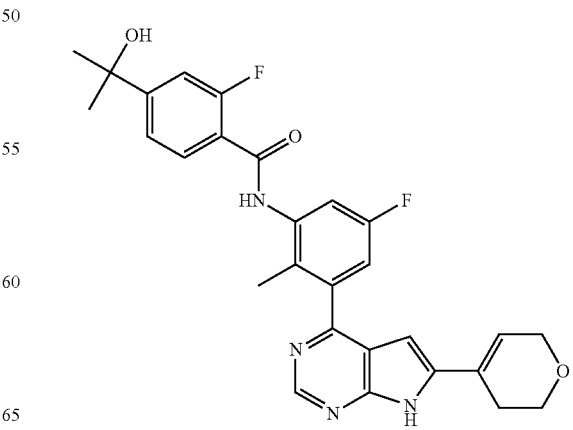

(1) 4-Chloro-6-(3,6-dihydro-2H-pyran-4-yl)-7H-pyrrolo[2,3-d]pyrimidine, Intermediate 11

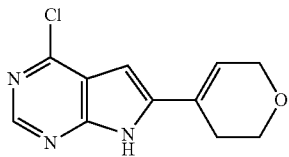 [SMILES: Clc1ncnc2[nH]c(C3=CCOCC3)cc12]

Intermediate 11 was prepared analogue to Intermediate 1 by replacing 4-(4,4,5,5-tetramethyl-[1,2,3]dioxaborolan-2-yl)-3,6-dihydro-2H-pyridine-1-carboxylic acid tert-butyl ester with 3,6-dihydro-2H-pyran-4-boronic acid pinacolester.

MS (ESI): 236 [M+H]$^+$, $^1$H-NMR (DMSO-d$_6$): δ (ppm) 12.69 (br s, 1H), 8.56 (s, 1H), 6.67 (m, 1H), 6.58 (s, 1H), 4.29 (m, 2H), 3.84 (m, 2H), 2.50 (m, 2H).

(2) 3-[6-(3,6-Dihydro-2H-pyran-4-yl)-7H-pyrrolo[2,3-d]pyrimidin-4-yl]-5-fluoro-2-methyl-phenylamine, Intermediate 12

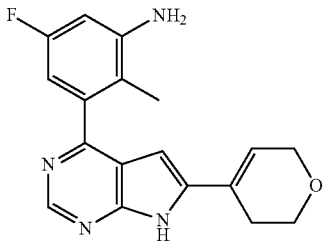 [SMILES: Cc1c(N)cc(F)cc1-c1ncnc2[nH]c(C3=CCOCC3)cc12]

Intermediate 12 was prepared analogue to Intermediate 6 by replacing Intermediate 3 with Intermediate 11.

MS (ESI): 325 [M+H]$^+$, $^1$H-NMR (DMSO-d$_6$): δ (ppm) 12.34 (br s, 1H), 8.77 (s, 1H), 6.62 (m, 1H), 6.56 (m, 1H), 6.37 (m, 1H), 6.25 (s, 1H), 5.37 (br s, 2H), 4.27 (m, 2H), 3.80 (m, 2H), 2.45 (m, 2H), 1.89 (s, 3H).

(3) N-{3-[6-(3,6-Dihydro-2H-pyran-4-yl)-7H-pyrrolo[2,3-d]pyrimidin-4-yl]-5-fluoro-2-methyl-phenyl}-2-fluoro-4-(1-hydroxy-1-methyl-ethyl)-benzamide

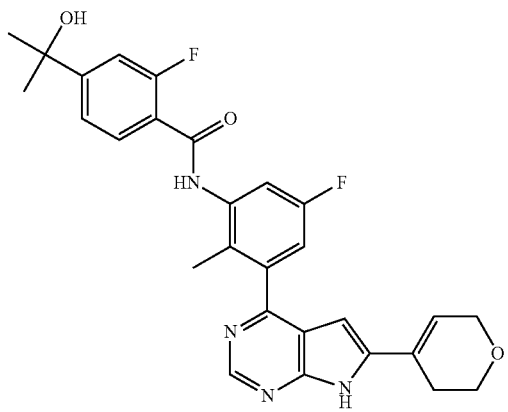 [SMILES: Cc1c(NC(=O)c2ccc(C(C)(C)O)cc2F)cc(F)cc1-c1ncnc2[nH]c(C3=CCOCC3)cc12]

Example 22 was prepared analogue to Intermediate 9 by replacing Intermediate 7 with Intermediate 12.

MS (ESI): 505 [M+H]$^+$, $^1$H-NMR (DMSO-d$_6$): δ (ppm) 12.45 (br s, 1H), 9.95 (s, 1H), 8.83 (s, 1H), 7.73 (m, 1H), 7.63 (m, 1H), 4.43 (m, 2H), 7.19 (m, 1H), 6.65 (s, 1H), 6.34 (s, 1H), 5.32 (s, 1H), 4.29 (s, 2H), 3.81 (m, 2H), 2.47 (m, 2H), 2.15 (s, 3H), 1.46 (s, 6H).

Example 23

N-{3-[6-(3,6-Dihydro-2H-pyran-4-yl)-7H-pyrrolo[2,3-d]pyrimidin-4-yl]-2-hydroxymethyl-phenyl}-2-fluoro-4-(1-hydroxy-1-methyl-ethyl)-benzamide

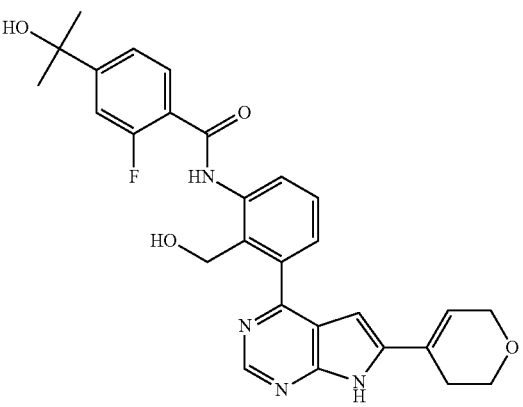 [SMILES: CC(C)(O)c1ccc(C(=O)Nc2cccc(-c3ncnc4[nH]c(C5=CCOCC5)cc34)c2CO)c(F)c1]

(1) 2-(tert-Butyl-diphenyl-silanyloxymethyl)-3-[6-(3,6-dihydro-2H-pyran-4-yl)-7H-pyrrolo[2,3-d]pyrimidin-4-yl]-phenylamine, Intermediate 13

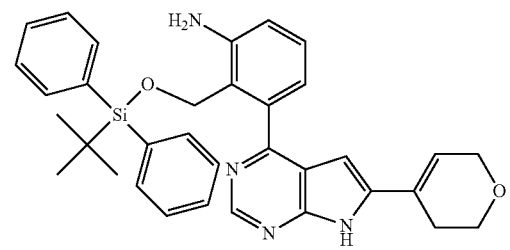 [SMILES: CC(C)(C)[Si](OCc1c(N)cccc1-c1ncnc2[nH]c(C3=CCOCC3)cc12)(c1ccccc1)c1ccccc1]

Intermediate 13 was prepared analogue to Intermediate 7 by replacing Intermediate 6 with Intermediate 11.

MS (ESI): 561 [M+H]$^+$, $^1$H-NMR (DMSO-d$_6$): δ (ppm) 12.25 (br s, 1H), 8.52 (s, 1H), 7.40-7.10 (m, 11H), 6.90 (d, 1H), 6.71 (d, 1H), 6.59 (s, 1H), 6.16 (s, 1H), 5.28 (s, 2H), 4.81 (s, 2H), 4.27 (m, 2H), 3.78 (m, 2H), 2.37 (m, 2H), 0.82 (s, 9H).

(2) N-{2-(tert-Butyl-diphenyl-silanyloxymethyl)-3-[6-(3,6-dihydro-2H-pyran-4-yl)-7H-pyrrolo[2,3-d]pyrimidin-4-yl]-phenyl}-2-fluoro-4-(1-hydroxy-1-methyl-ethyl)-benzamide, Intermediate 14

Example 24

4-tert-Butyl-N-{3-[6-(3,6-dihydro-2H-thiopyran-4-yl)-7H-pyrrolo[2,3-d]pyrimidin-4-yl]-5-fluoro-2-methyl-phenyl}-benzamide

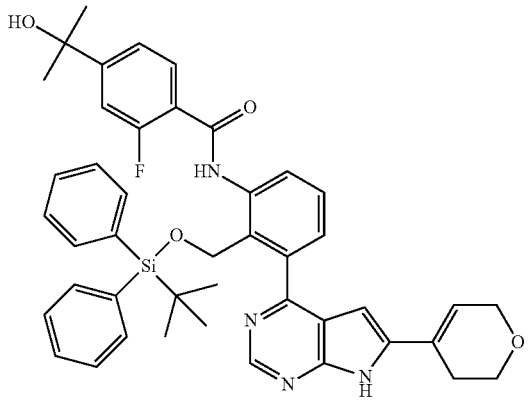 [SMILES: CC(C)(O)c1ccc(C(=O)Nc2cccc(-c3ncnc4[nH]c(C5=CCOCC5)cc34)c2CO[Si](c2ccccc2)(c2ccccc2)C(C)(C)C)c(F)c1]

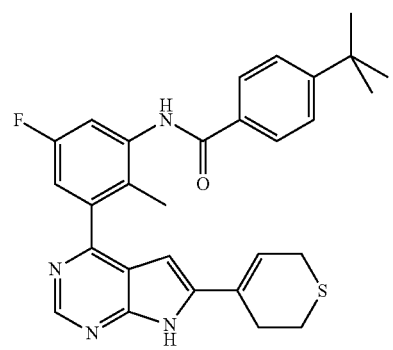 [SMILES: Cc1c(NC(=O)c2ccc(C(C)(C)C)cc2)cc(F)cc1-c1ncnc2[nH]c(C3=CCSCC3)cc12]

Intermediate 14 was prepared analogue to Intermediate 9 by replacing Intermediate 7 with Intermediate 13.

(1) 4-Chloro-6-(3,6-dihydro-2H-thiopyran-4-yl)-7H-pyrrolo[2,3-d]pyrimidine, Intermediate 15

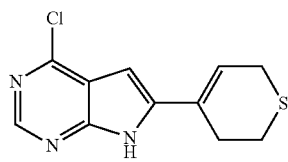 [SMILES: Clc1ncnc2[nH]c(C3=CCSCC3)cc12]

(3) N-{3-[6-(3,6-Dihydro-2H-pyran-4-yl)-7H-pyrrolo[2,3-d]pyrimidin-4-yl]-2-hydroxymethyl-phenyl}-2-fluoro-4-(1-hydroxy-1-methyl-ethyl)-benzamide Intermediate 15 was prepared analogue to Intermediate 1 by replacing 4-(4,4,5,5-tetramethyl-[1,2,3]dioxaborolan-2-yl)-3,6-dihydro-2H-pyridine-1-carboxylic acid tert-butyl ester with 2-(3,6-dihydro-2H-thiopyran-4-yl)-4,4,5,5-tetramethyl-[1,3,2]dioxaborolane.

MS (ESI): 252 [M+H]$^+$ (2) 3-[6-(3,6-Dihydro-2H-thiopyran-4-yl)-7H-pyrrolo[2,3-d]pyrimidin-4-yl]-5-fluoro-2-methyl-phenylamine, Intermediate 16

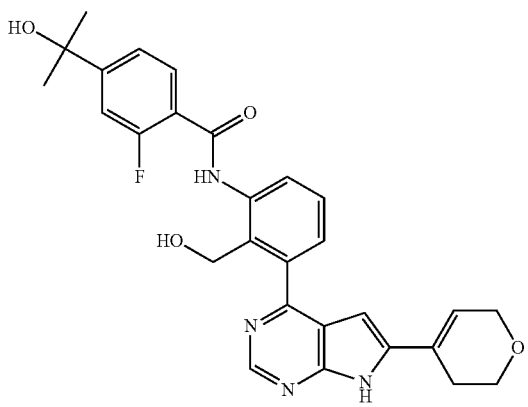

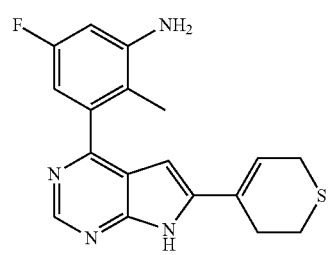 [SMILES: Cc1c(N)cc(F)cc1-c1ncnc2[nH]c(C3=CCSCC3)cc12]

Example 23 was prepared analogue to Example 16 step 4 by replacing Intermediate 9 with Intermediate 14.

MS (ESI): 503 [M+H]$^+$, $^1$H-NMR (DMSO-d$_6$): δ (ppm) 12.42 (s, 1H), 10.39 (d, 1H), 8.82 (s, 1H), 8.19 (d, 1H), 7.86 (t, 1H), 7.52-7.30 (m, 4H), 6.62 (br s, 1H), 6.42 (s, 1H), 5.65 (m, 1H), 5.26 (s, 1H), 4.63 (m, 2H), 4.27 (m, 2H), 3.80 (m, 2H), 2.41 (m, 2H), 1.45 (s, 6H).

Intermediate 16 was prepared analogue to Intermediate 6 by replacing Intermediate 3 with Intermediate 15.

MS (ESI): 341 [M+H]$^+$ (3) 4-tert-Butyl-N-{3-[6-(3,6-dihydro-2H-thiopyran-4yl)-7H-pyrrolo[2,3-d]pyrimidin-4-yl]-5-fluor-2-methyl-phenyl}-benzamide

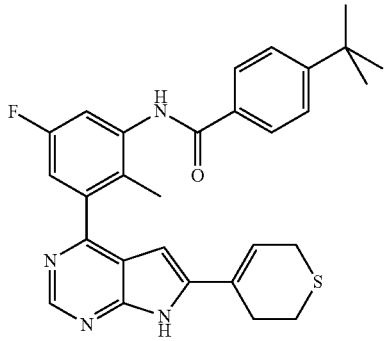 [SMILES: Cc1c(NC(=O)c2ccc(C(C)(C)C)cc2)cc(F)cc1-c1ncnc2[nH]c(C3=CCSCC3)cc12]

Example 24 was prepared analogue to Example 15 by replacing Intermediate 6 with Intermediate 16 and 4-dimethyaminobenzoyl chloride with tert-butylbenzoyl chloride.

MS (ESI): 501 [M+H]+, 1H-NMR (DMSO-d6): δ (ppm) 12.39 (s, 1H), 9.97 (s, 1H), 8.82 (s, 1H), 7.95 (d, 2H), 7.56 (d, 2H), 7.47 (m, 1H), 71.19 (m, 1H), 6.78 (m, 1H), 6.34 (s, 1H), 3.37 (m, 2H), 2.82 (m, 2H), 2.66 (m, 2H), 2.11 (s, 3H), 1.32 (s, 9H).

Example 25

4-tert-Butyl-N-{5-fluoro-2-methyl-3-[6-(3,6-dihydro-1-oxido-2H-thiopyran-4-yl)-7H-pyrrolo[2,3-d]pyrimidin-4-yl]-phenyl}-benzamide

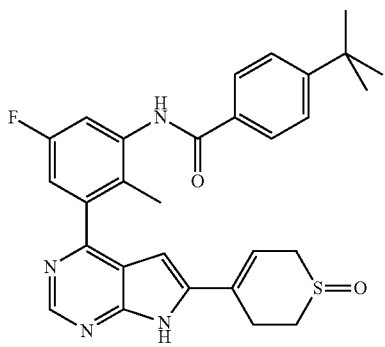 [SMILES: Cc1c(NC(=O)c2ccc(C(C)(C)C)cc2)cc(F)cc1-c1ncnc2[nH]c(C3=CCS(=O)CC3)cc12]

Example 24 (160 mg, 0.32 mmol) was dissolved in acetic acid (5 ml) and hydrogen peroxide (0.033 ml, 0.32 mmol) was added. The mixture was stirred at room temperature for 2 hours. The mixture was treated with sodium hydrogen sulfite solution (10%, 10 ml) for 10 minutes, diluted with water, basified with 2N sodium hydroxide solution and extracted with EtOAc. The organic layer was washed with brine (2×), dried over sodium sulfate, filtered and evaporated. The residue was purified by flash chromatography on silica (EtOAc/MeOH/NH4OH 9:1:0.1 to EtOAc/MeOH/NH4OH 85:15:1.5) to afford the compound Example 25 as a beige solid.

MS (ESI): 517 [M+H]+, 1H-NMR (DMSO-d6): δ (ppm) 12.49 (br s, 1H), 9.99 (s, 1H), 8.85 (s, 1H), 7.96 (d, 2H), 7.55 (d, 2H), 7.49 (m, 1H), 7.21 (m, 1H), 6.49 (br s, 1H), 6.46 (s, 1H), 3.69 (m, 1H), 3.50 (m, 1H), 3.13 (m, 1H), 295 (m, 1H), 2.89 (m, 1H), 2.80 (m, 1H), 2.13 (s, 3H), 1.31 (s, 9H).

Example 26

4-tert-Butyl-N-{3-[6-(3,6-dihydro-1,1-dioxido-2H-thiopyran-4-yl)-7H-pyrrolo[2,3-d]pyrimidin-4-yl]-5-fluoro-2-methyl-phenyl}-benzamide

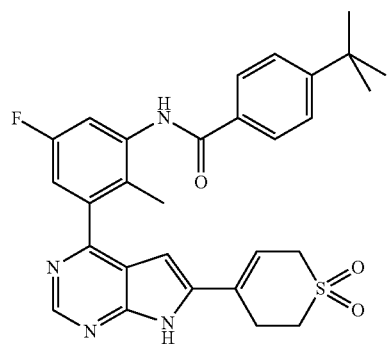 [SMILES: Cc1c(NC(=O)c2ccc(C(C)(C)C)cc2)cc(F)cc1-c1ncnc2[nH]c(C3=CCS(=O)(=O)CC3)cc12]

Example 24 (160 mg, 0.32 mmol) was dissolved in DCM (15 ml), then trifluoro acetic acid (5 ml) and hydrogen peroxide (0.065 ml, 0.64 mmol) were added. The mixture was stirred at room temperature for 2 hours. The mixture was treated with sodium hydrogen sulfite solution (10%, 10 ml) for 10 minutes, diluted with water, basified with 2N sodium hydroxide solution and extracted with EtOAc. The organic layer was washed with brine (2×), dried over sodium sulfate, filtered and evaporated. The residue was purified by flash chromatography on silica (EtOAc/MeOH/NH4OH 98:2:0.2 to EtOAc/MeOH/NH4OH 95:5:0.5) to afford the compound Example 26 as a beige solid.

MS (ESI): 533 [M+H]+, 1H-NMR (DMSO-d6): δ (ppm) 12.45 (br s, 1H), 9.93 (s, 1H), 8.84 (s, 1H), 7.91 (d, 2H), 7.56 (d, 2H), 7.49 (m, 1H), 7.21 (m, 1H), 6.41 (m, 2H), 4.00 (m, 2H), 3.36 (m, 2H), 3.07 (m, 2H), 2.16 (s, 3H), 1.33 (s, 9H).

Example 27

4-tert-Butyl-N-{3-[6-(1,4-dioxa-spiro[4.5]dec-7-en-8-yl)-7H-pyrrolo[2,3-d]pyrimidin-4-yl]-5-fluoro-2-methyl-phenyl}-benzamide

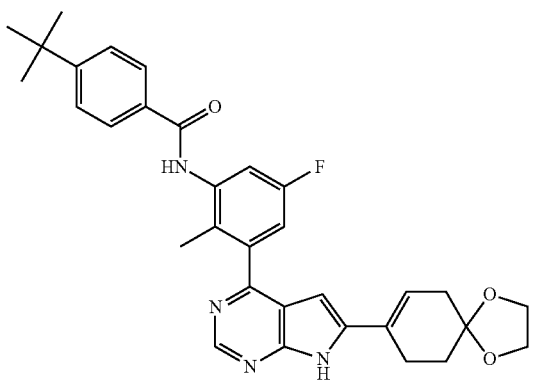 [SMILES: Cc1c(NC(=O)c2ccc(C(C)(C)C)cc2)cc(F)cc1-c1ncnc2[nH]c(C3=CCC4(CC3)OCCO4)cc12]

(1) 4-Chloro-6-(1,4-dioxa-spiro[4.5]dec-7-en-8-yl)-7H-pyrrolo[2,3-d]pyrimidine, Intermediate 17

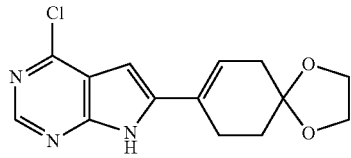 [SMILES: Clc1ncnc2[nH]c(C3=CCC4(CC3)OCCO4)cc12]

Intermediate 17 was prepared analogue to Intermediate 1 by replacing 4-(4,4,5,5-tetramethyl-[1,2,3]dioxaborolan-2-yl)-3,6-dihydro-2H-pyridine-1-carboxylic acid tert-butyl ester with 1,4-dioxaspiro[5,5]dec-7-en-8-boronic acid pinacol ester.

MS (ESI): 292 [M+H]$^+$, $^1$H-NMR (DMSO-d$_6$): δ (ppm) 12.59 (br s, 1H), 8.54 (s, 1H), 6.54 (s, 1H), 6.50 (br s, 1H), 3.93 (m, 4H), 2.61 (m, 2H), 2.43 (m, 2H), 1.83 (m, 2H).

(2) 3-[6-(1,4-Dioxa-spiro[4.5]dec-7-en-8-yl)-7H-pyrrolo[2,3-d]pyrimidin-4-yl]-5-fluoro-2-methyl-phenylamine, Intermediate 18

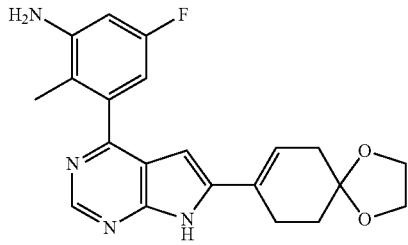 [SMILES: Cc1c(N)cc(F)cc1-c1ncnc2[nH]c(C3=CCC4(CC3)OCCO4)cc12]

Intermediate 18 was prepared analogue to Intermediate 6 by replacing Intermediate 3 with Intermediate 17.

MS (ESI): 381 [M+H]$^+$, $^1$H-NMR (DMSO-d$_6$): δ (ppm) 12.24 (br s, 1H), 8.75 (s, 1H), 6.55 (m, 1H), 6.46 (br s, 1H), 6.38 (m, 1H), 6.21 (s, 1H), 5.36 (s, 2 NH), 3.91 (m, 4H), 2.55 (m, 2H), 2.41 (m, 2H), 1.88 (s, 3H), 1.78 (m, 2H).

(3) 4-tert-Butyl-N-{3-[6-(1,4-dioxa-spiro[4.5]dec-7-en-8-yl)-7H-pyrrolo[2,3-d]pyrimidin-4-yl]-5-fluoro-2-methyl-phenyl}-benzamide

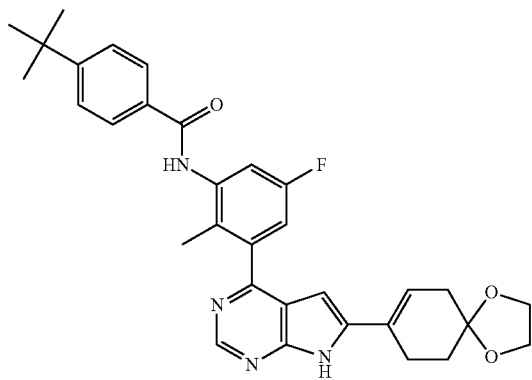 [SMILES: Cc1c(NC(=O)c2ccc(C(C)(C)C)cc2)cc(F)cc1-c1ncnc2[nH]c(C3=CCC4(CC3)OCCO4)cc12]

Example 27 was prepared analogue to Example 15 by replacing Intermediate 6 with Intermediate 18 and 4-dimethylaminobenzoyl chloride with 4-tert-butylbenzoyl chloride.

MS (ESI): 541 [M+H]$^+$, $^1$H-NMR (DMSO-d$_6$): δ (ppm) 12.36 (br s, 1H), 9.98 (s, 1H), 8.82 (s, 1H), 7.96 (d, 2H), 7.58 (d, 2H), 7.48 (m, 1H), 7.21 (m, 1H), 6.50 (br s, 1H), 6.29 (s, 1H), 3.93 (m, 4H), 2.58 (m, 2H), 2.43 (m, 2H), 2.12 (s, 3H), 1.81 (m, 2H), 1.33 (s, 9H).

Example 28

4-tert-Butyl-N-{5-fluoro-3-[6-(4-hydroxy-cyclohex-1-enyl)-7H-pyrrolo[2,3-d]pyrimidin-4-yl]-2-methyl-phenyl}-benzamide

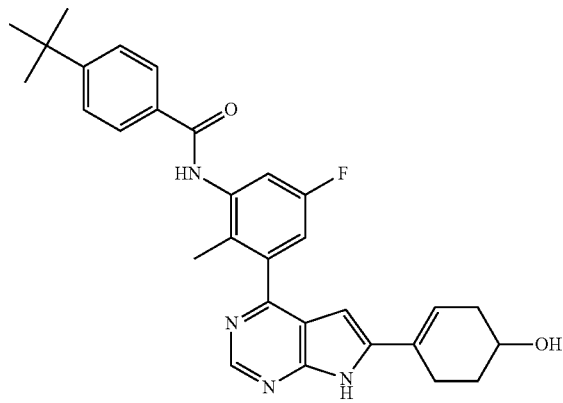 [SMILES: Cc1c(NC(=O)c2ccc(C(C)(C)C)cc2)cc(F)cc1-c1ncnc2[nH]c(C3=CCC(O)CC3)cc12]

(1) 4-tert-Butyl-N-{5-fluoro-3-[6-(4-hydroxy-cyclohex-1-enyl)-7H-pyrrolo[2,3-d]pyrimidin-4-yl]-2-methyl-phenyl}-benzamide, Intermediate 19

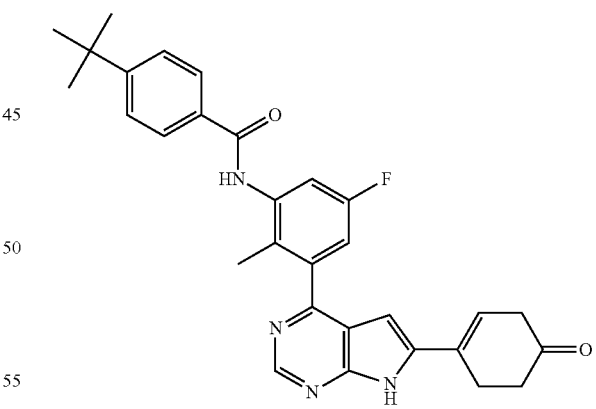

A mixture of Example 27 (450 mg, 0.832 mmol) and TFA (6 ml) in DCM (30 ml) was stirred at r.t. for 6 hrs. The solvents were removed in vacuo and the crude product was purified by flash chromatography (silica gel, EtOAc/MeOH/NH$_4$OH gradient) to yield Intermediate 19.

MS (ESI): 497 [M+H]$^+$, $^1$H-NMR (DMSO-d$_6$): δ (ppm) 12.47 (br s, 1H), 9.97 (s, 1H), 8.83 (s, 1H), 7.94 (d, 2H), 7.57 (d, 2H), 7.48 (m, 1H), 7.20 (m, 1H), 6.65 (br s, 1H), 6.40 (s, 1H), 3.11 (m, 2H), 2.86 (m, 2H), 2.53 (m, 2H), 2.11 (s, 3H), 1.33 (s, 9H).

(2) 4-tert-Butyl-N-{5-fluoro-3-[6-(4-hydroxy-cyclo-hex-1-enyl)-7H-pyrrolo[2,3-d]pyrimidin-4-yl]-2-methyl-phenyl}-benzamide

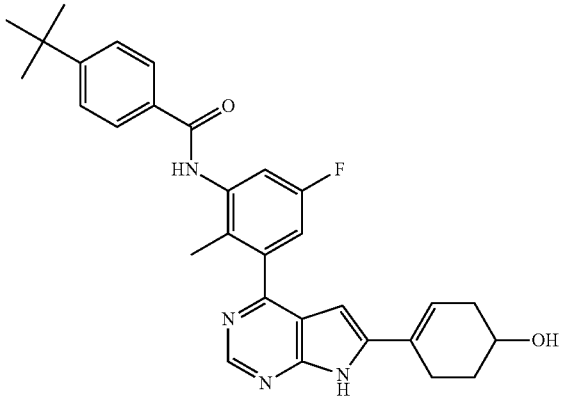 [SMILES: Cc1c(NC(=O)c2ccc(C(C)(C)C)cc2)cc(F)cc1-c1ncnc2[nH]c(C3=CCC(O)CC3)cc12]

To a solution of Intermediate 19 (100 mg, 0.201 mmol) in MeOH (25 ml) was added NaBH$_4$ (9.1 mg, 0.242 mg). The mixture was stirred at r.t. for 2 hrs, then the solvent was removed in vacuo, and the crude mixture was purified by flash chromatography (silica gel, EtOAc/MeOH/NH$_4$OH gradient) to yield Example 28.

MS (ESI): 499 [M+H]$^+$, $^1$H-NMR (DMSO-d$_6$): δ (ppm) 12.31 (br s, 1H), 9.96 (s, 1H), 8.79 (s, 1H), 7.94 (d, 2H), 7.57 (d, 2H), 7.47 (m, 1H), 7.18 (m, 1H), 6.50 (br s, 1H), 6.24 (s, 1H), 4.73 (br s, 1H), 3.80 (m, 1H), 2.51 (m, 2H), 2.44 (m, 1H), 2.39 (m, 1H), 2.10 (s, 3H), 1.84 (m, 1H), 1.59 (m, 1H), 1.33 (s, 9H).

Example 29

4-{4-[3-(4-Cyclopropyl-benzoylamino)-5-fluoro-2-methyl-phenyl]-7H-pyrrolo[2'3-d]pyrimidin-6-yl}-3,6-dihydro-2H-pyridine-1-carboxylic acid dimethylamide

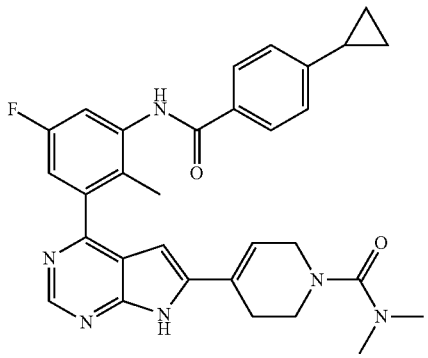 [SMILES: Cc1c(NC(=O)c2ccc(C3CC3)cc2)cc(F)cc1-c1ncnc2[nH]c(C3=CCN(C(=O)N(C)C)CC3)cc12]

(1) 4-[4-(3-Amino-5-fluoro-2-methyl-phenyl)-7H-pyrrolo[2,3-d]pyrimidin-6-yl]-3,6-dihydro-2H-pyridine-1-carboxylic acid tert-butyl ester, Intermediate 20

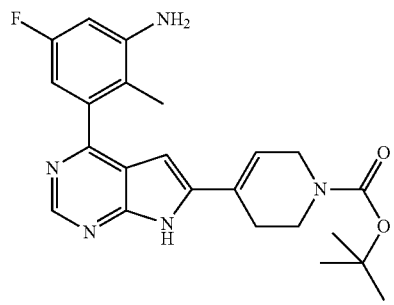 [SMILES: Cc1c(N)cc(F)cc1-c1ncnc2[nH]c(C3=CCN(C(=O)OC(C)(C)C)CC3)cc12]

For the Suzuki coupling of chloro compound Intermediate 1 (0.63 g, 1.88 mmol) and boronic ester derivative Intermediate 5 (0.52 g, 2.07 mmol) the same procedure was used as described in Example 1 step 6, to afford the compound Intermediate 20 as a beige solid.

MS (ESI): 424 [M+H]$^+$, $^1$H-NMR (DMSO-d$_6$): δ (ppm) 12.33 (br s, 1H), 8.76 (s, 1H), 6.54 (m, 2H), 6.40 (d, 1H), 6.26 (s, 1H), 5.36 (s, 2NH), 4.05 (br s, 2H), 3.51 (m, 2H), 1.99 (m, 2H), 1.88 (s, 3H), 1.42 (s, 9H).

(2) 4-{4-[3-(Cyclopropyl-benzoylamino)-5-fluoro-2-methyl-phenyl]-7H-pyrrolo[2,3-d]pyrimidin-6-yl}-3,6-dihydro-2H-pyridine-1-carboxylic acid tert-butyl ester, Intermediate 21

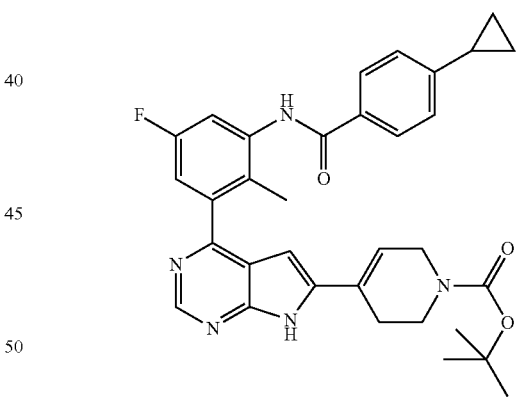

To a solution of 4-cyclopropyl benzoic acid (0.58 g, 3.57 mmol) in toluene (2 ml), thionyl chloride (1.29 ml, 17.87 mmol) was added. The mixture was stirred at 80° C. for 2 hours and afterwards evaporated under reduced pressure. The residue was dissolved together with Intermediate 20 (1.0 g, 2.36 mmol) in pyridine (5 ml) and the mixture was stirred at room temperature for 2 hours. Pyridine was evaporated under reduced pressure and the residue was dissolved in DCM and washed with saturated sodium hydrogen carbonate solution and brine (2×). The residue was purified by flash chromatography on silica (cyclohexane to EtOAc) to afford the compound Intermediate 21 as a beige solid.

MS (ESI): 568 [M+H]$^+$, $^1$H-NMR (DMSO-d$_6$): δ (ppm) 12.43 (br s, 1H), 9.93 (s, 1NH) 8.82 (s, 1H), 7.89 (d, 2H), 7.46

(m, 1H), 7.24 (d, 2H), 7.18 (m, 1H), 6.57 (br s, 1H), 6.33 (s, 1H), 4.06 (br s, 2H), 3.52 (m, 2H), 2.48 (m, 2H), 2.10 (s, 3H), 2.01 (m, 1H), 1.42 (s, 9H), 1.02 (m, 2H), 0.76 (m, 2H).

(3) 4-Cyclopropyl-N-{5-fluoro-2-methyl-3-[6-(1,2,3,6-tetrahydro-pyridin-4-yl)-7H-pyrrolo[2,3-d]pyrimidin-4-yl]-phenyl}-benzamide, Intermediate 22

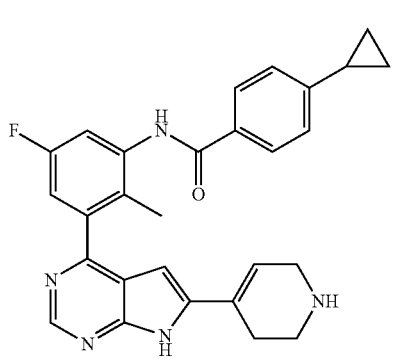 [SMILES: Cc1c(NC(=O)c2ccc(C3CC3)cc2)cc(F)cc1-c1ncnc2[nH]c(C3=CCNCC3)cc12]

The BOC protecting group of compound Intermediate 21 (1.0 g, 1.76 mmol) was removed as described in Example 1 step 2 to afford the compound Intermediate 22 as a beige solid.

MS (ESI): 468 [M+H]$^+$, $^1$H-NMR (DMSO-d$_6$): δ (ppm) 12.33 (br s, 1H), 9.94 (s, 1NH) 8.80 (s, 1H), 7.89 (d, 2H), 7.47 (m, 1H), 7.24 (d, 2H), 7.19 (m, 1H), 6.62 (br s, 1H), 6.24 (s, 1H), 3.41 (br s, 2H), 2.88 (m, 2H), 2.33 (m, 2H), 2.10 (s, 3H), 2.01 (m, 1H), 1.04 (m, 2H), 0.77 (m, 2H).

(4) 4-{4-[3-(4-Cyclopropyl-benzoylamino)-5-fluoro-2-methyl-phenyl]-7H-pyrrolo[2'3-d]pyrimidin-6-yl}-3,6-dihydro-2H-pyridine-1-carboxylic acid dimethylamide

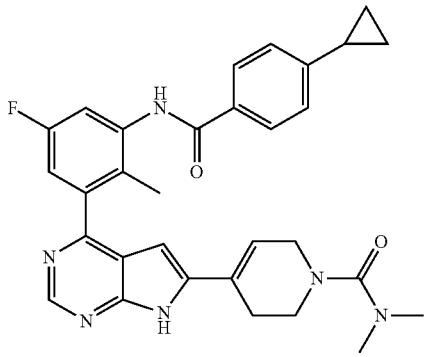 [SMILES: Cc1c(NC(=O)c2ccc(C3CC3)cc2)cc(F)cc1-c1ncnc2[nH]c(C3=CCN(C(=O)N(C)C)CC3)cc12]

The amino compound Intermediate 22 (0.2 g, 0.51 mmol) was acylated as described in Example 1 step 3 to afford the compound Example 29 as a beige solid.

MS (ESI): 539 [M+H]$^+$, $^1$H-NMR (DMSO-d$_6$): δ (ppm) 12.42 (br s, 1H), 9.93 (s, 1NH) 8.82 (s, 1H), 7.89 (d, 2H), 7.46 (m, 1H), 7.24 (d, 2H), 7.18 (m, 1H), 6.59 (br s, 1H), 6.32 (s, 1H), 3.90 (br s, 2H), 3.33 (m, 2H), 2.76 (s, 6H), 2.53 (m, 2H), 2.10 (s, 3H), 2.02 (m, 1H), 1.03 (m, 2H), 0.77 (m, 2H).

Example 30

4-Cyclopropyl-N-(5-fluoro-2-methyl-3-{6-[1-(pyrrolidine-1-carbonyl)-1,2,3,6-tetrahydro-pyridin-4-yl]-7H-pyrrolo[2,3-d]pyrimidin-4-yl}-phenyl)-benzamide

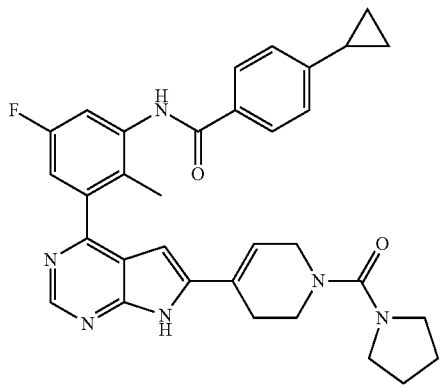 [SMILES: Cc1c(NC(=O)c2ccc(C3CC3)cc2)cc(F)cc1-c1ncnc2[nH]c(C3=CCN(C(=O)N4CCCC4)CC3)cc12]

The amino compound Intermediate 22 (0.2 g, 0.51 mmol) was acylated using pyrrolidine-1-carbonyl chloride as described in Example 1 step 3 to afford the compound Example 30 as a beige solid.

MS (ESI): 565 [M+H]$^+$, $^1$H-NMR (DMSO-d$_6$): δ (ppm) 12.41 (br s, 1H), 9.93 (s, 1NH) 8.82 (s, 1H), 7.89 (d, 2H), 7.45 (m, 1H), 7.24 (d, 2H), 7.18 (m, 1H), 6.58 (br s, 1H), 6.32 (s, 1H), 3.93 (br s, 2H), 3.38 (m, 2H), 3.29 (m, 4H), 2.52 (m, 2H), 2.10 (s, 3H), 2.0 (m, 1H), 1.75 (m, 4H), 1.04 (m, 2H), 0.76 (m, 2H).

Example 31

Acetic acid 2-(4-{4-[3-(4 cyclopropyl-benzoylamino)-5-fluoro-2-methyl-phenyl]-7H-pyrrolo[2,3-d]pyrimidin-6-yl}-3,6-dihydro-2H-pyridin-1-yl)-2-oxo-ethyl ester

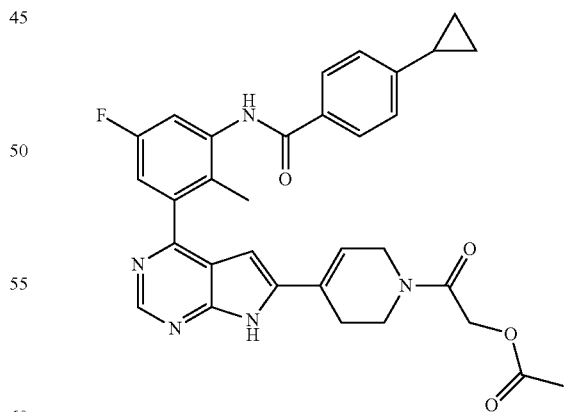

The amino compound Intermediate 22 (0.15 g, 0.32 mmol) was acylated using acetic acid chlorocarbonylmethyl ester as described in Example 1 step 3 to afford the compound Example 31 as a beige solid.

MS (ESI): 568 [M+H]$^+$, $^1$H-NMR (DMSO-d$_6$): δ (ppm) 12.45 (br s, 1H), 9.94 (s, 1NH) 8.83 (s, 1H), 7.89 (d, 2H), 7.47

(m, 1H), 7.22 (d, 2H), 7.19 (m, 1H), 6.58 (br s, 1H), 6.34 (s, 1H), 4.86 (m, 2H), 4.15 (m, 2H), 3.57 (m, 2H), 2.59 (m, 2H), 2.10 (s, 3H), 2.08 (s, 3H), 2.01 (m, 1H), 1.03 (m, 2H), 0.77 (m, 2H).

Example 32

4-Cyclopropyl-N-(5-fluoro-3-{6-[1-(2-hydroxy-acetyl)-1,2,3,6-tetrahydro-pyridin-4-yl]-7H-pyrrolo[2,3-d]pyrimidin-4-yl}-2-methyl-phenyl)benzamide

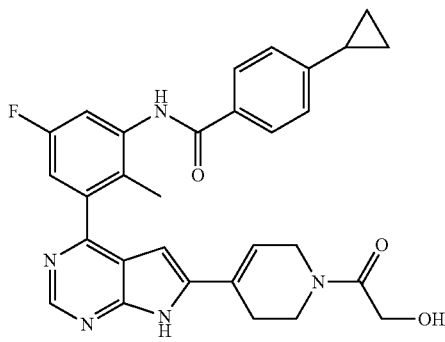 [SMILES: Cc1c(NC(=O)c2ccc(C3CC3)cc2)cc(F)cc1-c1ncnc2[nH]c(C3=CCN(C(=O)CO)CC3)cc12]

The acetyl compound of Example 31 (100 mg, 0.17 mmol) was dissolved in THF (1 ml) and EtOH (1 ml) and 2N sodium hydroxide solution (0.31 ml, 0.62 mmol) was added. The mixture was stirred at room temperature for 5 minutes. The mixture was diluted with water and extracted with DCM (3×). The organic layer was washed with brine (2×), dried over sodium sulfate, filtered and evaporated. The residue was purified by flash chromatography on silica (EtOAc to EtOAc/MeOH/NH$_4$OH 98:2:0.2) to afford the compound Example 32 as a beige solid.

MS (ESI): 526 [M+H]$^+$, $^1$H-NMR (DMSO-d$_6$): δ (ppm) 12.47 (br s, 1H), 9.95 (s, 1NH) 8.82 (s, 1H), 7.89 (d, 2H), 7.47 (m, 1H), 7.24 (d, 2H), 7.18 (m, 1H), 6.61 (m, 1H), 6.33 (m, 1H), 4.63 (m, 2H), 4.04 (m, 4H), 3.68 (m, 1H), 3.54 (m, 1H), 2.57 (m, 2H), 2.10 (s, 3H), 2.01 (m, 1H), 1.04 (m, 2H), 0.77 (m, 2H).

Example 33

N-(3-{6-[1-(2 Cyano-acetyl)-1,2,3,6-tetrahydro-pyridin-4-yl]-7H-pyrrolo[2,3-d]pyrimidin-4-yl}-5-fluoro-2-methyl-phenyl)-4-cyclopropyl-benzamide

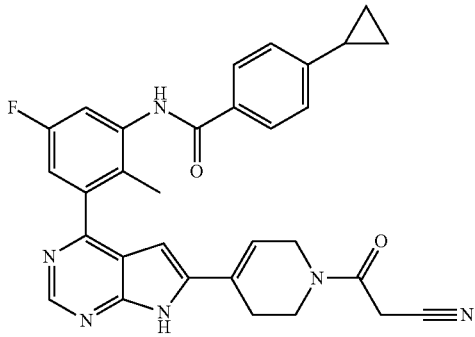 [SMILES: Cc1c(NC(=O)c2ccc(C3CC3)cc2)cc(F)cc1-c1ncnc2[nH]c(C3=CCN(C(=O)CC#N)CC3)cc12]

Amino compound Intermediate 22 (30 mg, 0.064 mmol), cyanoacetic acid (11 mg, 0.128 mmol) and HATU (61 mg, 0.16 mmol) were dissolved in DIPEA (0.056 ml, 0.321 mmol) and DMF (1.0 ml). The solution was stirred at room temperature for 24 hrs. The reaction was diluted with DCM and washed with saturated sodium hydrogen carbonate solution and brine (2×). The organic layer was dried with sodium sulfate and evaporated. The residue was purified by flash chromatography on silica (cyclohexane to EtOAc) to afford the compound Example 33 as a beige solid.

MS (ESI): 536 [M+H]$^+$, $^1$H-NMR (DMSO-d$_6$): δ (ppm) 9.56 (br s, 1NH) 8.76 (s, 1H), 7.85 (d, 2H), 7.43 (m, 1H), 7.19 (d, 2H), 7.09 (m, 1H), 6.53 (m, 1H), 6.29 (m, 1H), 4.16 (m, 2H), 3.94 (m, 2H), 3.63 (m, 2H), 2.56 (m, 2H), 2.10 (s, 3H), 2.01 (m, 1H), 1.01 (m, 2H), 0.74 (m, 2H).

Example 34

N-(5-Fluoro-2-methyl-3-{6-[1-(pyrrolidine-1-carbonyl)-1,2,3,6-tetrahydro-pyridin-4-yl]-7H-pyrrolo[2,3-d]pyrimidin-4-yl}-phenyl)-4-(pentafluoro-sulfanyl)-benzamide

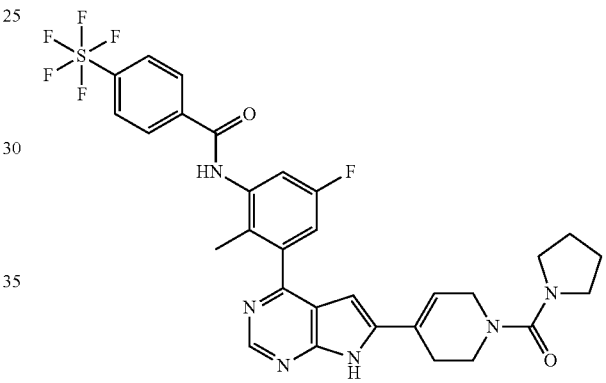

(1) 4-(4-{5-Fluoro-2-methyl-3-[4-(pentafluoro-sulfanyl)-benzoylamino]-phenyl}-7H-pyrrolo[2,3-d]pyrimidin-6-yl)-3,6-dihydro-2H-pyridine-1-carboxylic acid tert-butyl ester, Intermediate 23

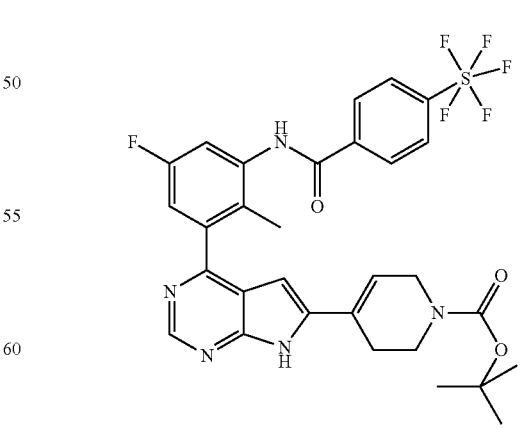

Intermediate 23 was prepared analogue to Intermediate 9 by replacing Intermediate 7 with Intermediate 20 and Intermediate 8 with 4-(pentafluoro-sulfanyl)-benzoic acid.

MS (ESI): 654 [M+H]+, 1H-NMR (DMSO-d6): δ (ppm) 12.44 (br s, 1H), 10.33 (s, 1H), 8.83 (s, 1H), 8.18 (d, 2H), 8.12 (d, 2H), 7.50 (m, 1H), 7.24 (m, 1H), 6.57 (m, 1H), 6.34 (s, 1H), 4.06 (m, 2H), 3.51 (m, 2H), 2.49 (m, 2H), 2.12 (s, 3H), 1.42 (s, 9H).

(2) N-{5-Fluoro-2-methyl-3-[6-(1,2,3,6-tetrahydro-pyridin-4-yl)-7H-pyrrolo[2,3-d]pyrimidin-4-yl]-phenyl}-4-(pentafluoro-sulfanyl)-benzamide, Intermediate 24

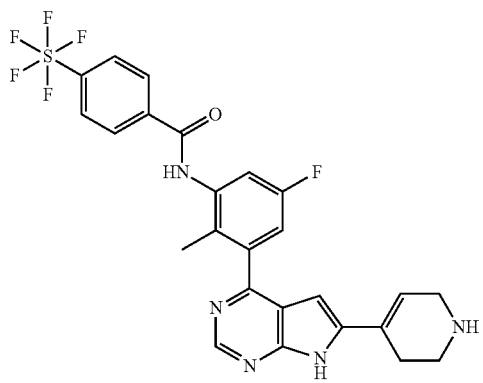 [SMILES: Cc1c(NC(=O)c2ccc(S(F)(F)(F)(F)F)cc2)cc(F)cc1-c1ncnc2[nH]c(C3=CCNCC3)cc12]

Intermediate 24 was prepared analogue to Intermediate 22 by replacing Intermediate 21 with Intermediate 23.

MS (ESI): 554 [M+H]+, 1H-NMR (DMSO-d6): δ (ppm) 12.42 (br s, 1H), 10.43 (s, 1H), 8.83 (s, 1H), 8.23 (d, 2H), 8.13 (d, 2H), 7.51 (m, 1H), 7.24 (m, 1H), 6.54 (m, 1H), 6.31 (s, 1H), 3.52 (m, 2H), 2.99 (m, 2H), 2.45 (m, 2H), 2.13 (s, 3H).

(3) N-(5-Fluoro-2-methyl-3-{6-[1-(pyrrolidine-1-carbonyl)-1,2,3,6-tetrahydro-pyridin-4-yl]-7H-pyrrolo[2,3-d]pyrimidin-4-yl}-phenyl)-4-(pentafluoro-sulfanyl)-benzamide

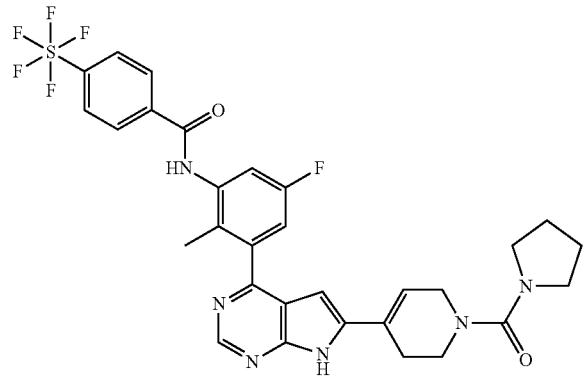 [SMILES: Cc1c(NC(=O)c2ccc(S(F)(F)(F)(F)F)cc2)cc(F)cc1-c1ncnc2[nH]c(C3=CCN(C(=O)N4CCCC4)CC3)cc12]

Example 34 was prepared analogue to Example 30 by replacing Intermediate 22 with Intermediate 24.

MS (ESI): 651 [M+H]+, 1H-NMR (DMSO-d6): δ (ppm) 12.42 (br s, 1H), 10.32 (s, 1H), 8.82 (s, 1H), 8.18 (d, 2H), 8.12 (d, 2H), 7.48 (m, 1H), 7.23 (m, 1H), 6.59 (m, 1H), 6.33 (s, 1H), 3.93 (m, 2H), 3.38 (m, 2H), 3.29 (m, 4H), 2.50 (m, 2H), 2.12 (s, 3H), 1.75 (m, 4H).

Example 35

Acetic acid 2-[4-(4-{5-fluoro-2-methyl-3-[4-(pentafluoro-sulfanyl)-benzoylamino]-phenyl}-7H-pyrrolo[2,3-d]pyrimidin-6-yl)-3,6-dihydro-2H-pyridin-1-yl]-2-oxo-ethyl ester

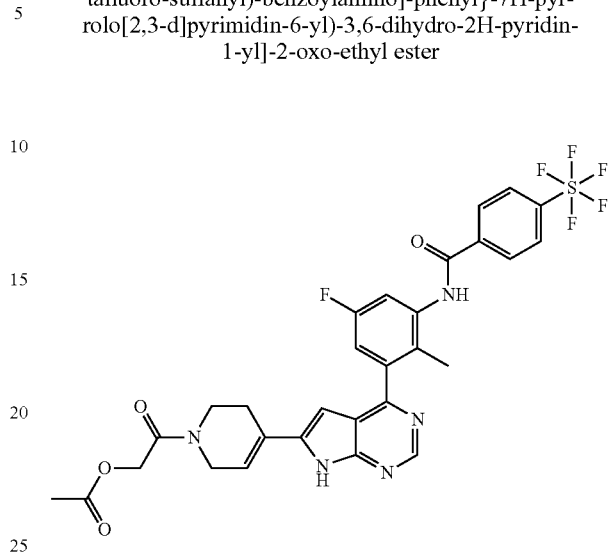

Example 35 was prepared analogue to Example 31 by replacing Intermediate 22 with Intermediate 24.

MS (ESI): 654 [M+H]+, 1H-NMR (DMSO-d6): δ (ppm) 12.47 (br s, 1H), 10.34 (s, 1H), 8.83 (s, 1H), 8.19 (d, 2H), 8.12 (d, 2H), 7.49 (m, 1H), 7.25 (m, 1H), 6.60 (m, 1H), 6.37 (s, 1H), 4.86 (s, 2H), 4.16 (m, 2H), 3.58 (m, 2H), 2.60 (m, 2H), 2.12 (s, 3H), 2.08 (s, 3H).

Example 36

N-(5-Fluoro-3-{6-[1-(2-hydroxy-acetyl)-1,2,3,6-tetrahydro-pyridin-4-yl]-7H-pyrrolo[2,3-d]pyrimidin-4-yl}-2-methyl-phenyl)-4-(pentafluoro-sulfanyl)-benzamide

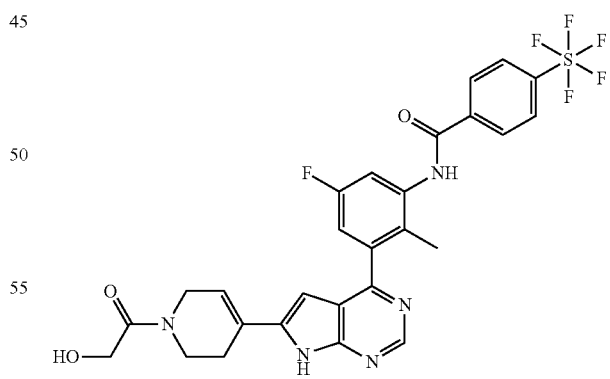

Example 36 was prepared analogue to Example 32 by replacing Example 31 with Example 35.

MS (ESI): 612 [M+H]+, 1H-NMR (DMSO-d6): δ (ppm) 12.43 (br s, 1H), 10.47 (s, 1H), 8.84 (s, 1H), 8.22 (d, 2H), 8.12 (d, 2H), 7.50 (m, 1H), 7.24 (m, 1H), 6.60 (m, 1H), 6.35 (s, 1H), 4.86 (s, 2H), 4.20 (m, 2H), 4.16 (m, 2H), 3.51 (m, 2H), 2.58 (m, 2H), 2.13 (s, 3H), 2.08 (s, 3H).

Example 37

4-{4-[3-(4-tert-Butyl-benzoylamino)-2-(tert-butyl-diphenyl-silanyloxymethyl)-phenyl]-7H-pyrrolo[2,3-d]pyrimidin-6-yl}-3,6-dihydro-2H-pyridine-1-carboxylic acid tert-butyl ester

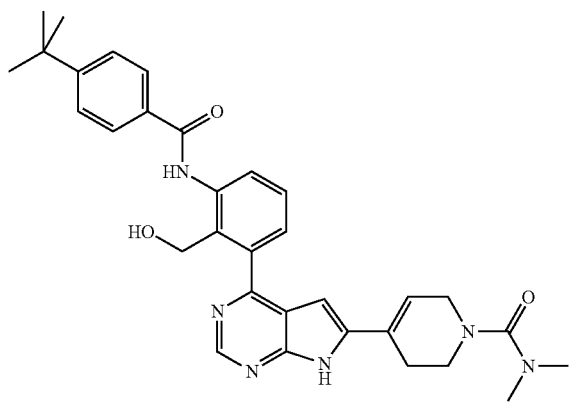 [SMILES: CN(C)C(=O)N1CC=C(c2cc3c(-c4cccc(NC(=O)c5ccc(C(C)(C)C)cc5)c4CO)ncnc3[nH]2)CC1]

(1) (2-Bromo-nitro-benzyloxy)-tert-butyl-diphenyl-silane, Intermediate 25

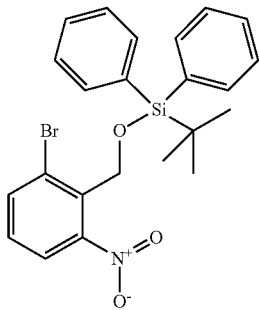 [SMILES: CC(C)(C)[Si](OCc1c(Br)cccc1[N+](=O)[O-])(c1ccccc1)c1ccccc1]

To a solution of (2-bromo-6-nitro-phenyl)-methanol (10.0 g, 43.1 mmol) and imidazole (5.87 g, 86.0 mmol) in DMF (20 ml), tert-butyl-chloro-diphenyl-silane was added dropwise at room temperature. The mixture was stirred at 50° C. for 1 hour. The mixture was diluted with EtOAc and washed with brine (2×). The organic layer was dried with sodium sulfate and evaporated. The residue was taken up in heptane and stirred at room temperature for 3 hours. The solid was filtered off to afford compound Intermediate 25 as a beige solid.

MS (ESI): 471 [M+H]$^+$, $^1$H-NMR (CDCl3): δ (ppm) 7.80 (m, 6H), 7.40 (m, 6H), 7.24 (m, 1H), 5.10 (s, 2H), 0.99 (s, 9H).

(2) 2-[2-(tert-Butyl-diphenyl-silanyloxymethyl)-3-nitro-phenyl]-4,4,5,5-tetramethyl-[1,3,2]dioxaborolane, Intermediate 26

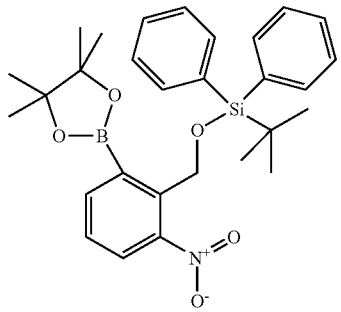 [SMILES: CC1(C)OB(c2cccc([N+](=O)[O-])c2CO[Si](c2ccccc2)(c2ccccc2)C(C)(C)C)OC1(C)C]

To a mixture of Intermediate 25 (5.0 g, 10.63 mmol) and bis(diphenylphosphino)ferrocenedichloropalladium (II) (0.43 g, 0.52 mmol) in 60 ml dioxane, bis-(pinacolato)-diboron (5.4 g, 21.26 mmol) and potassium acetate (6.25 g, 63.7 mmol) were added. The mixture was heated to 90° C. for 4 hours. After cooling the brownish mixture was filtered over Kieselgur (Supelco) and evaporated. The residue was purified by flash chromatography on silica (heptane to heptane/EtOAc 4:1) to afford the compound Intermediate 26 as a yellow oil.

MS (ESI): no peaks, $^1$H-NMR (CDCl3): δ (ppm) 7.65 (m, 5H), 7.30 (m, 8H), 5.30 (s, 2H), 1.10 (s, 12H), 0.97 (s, 9H).

(3) 2-(tert-Butyl-diphenyl-silanyloxymethyl)-3-(4,4,5,5-tetramethyl-[1,3,2]dioxborolan-2-yl)-phenylamine, Intermediate 27

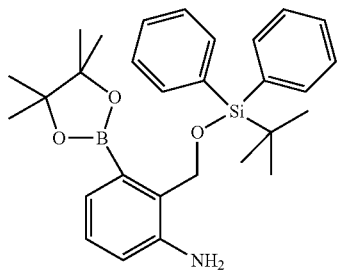 [SMILES: CC1(C)OB(c2cccc(N)c2CO[Si](c2ccccc2)(c2ccccc2)C(C)(C)C)OC1(C)C]

The nitro compound Intermediate 26 (10.0 g, 19.32 mmol) was dissolved in 300 ml EtOAc and Pd/C 10% (Pd) (2.0 g) were added. The mixture was hydrogenated at room temperature and normal pressure for 20 hours. The mixture was filtered over Kieselgur (Supelco) and evaporated. The residue was purified by flash chromatography on silica (cyclohexane to cyclohexane/EtOAc 4:1) to afford the compound Intermediate 27 as a yellow oil.

MS (ESI): 488 [M+H]$^+$, $^1$H-NMR (DMSO-d$_6$): δ (ppm) 7.63 (m, 4H), 7.44 (m, 2H), 7.39 (m, 4H), 7.03 (t, 1H), 6.91 (d, 1H), 6.84 (d, 1H), 5.10 (s, 2H), 5.08 (s, 2H), 0.99 (s, 12H), 0.98 (s, 9H).

(4) 4-tert-Butyl-N-[2-tert-butyl-diphenyl-silanyloxymethyl)-3-(4,4,5,5-tetramethyl-[1,3,2]dioxaborolan-2-yl)-phenyl]-benzamide, Intermediate 28

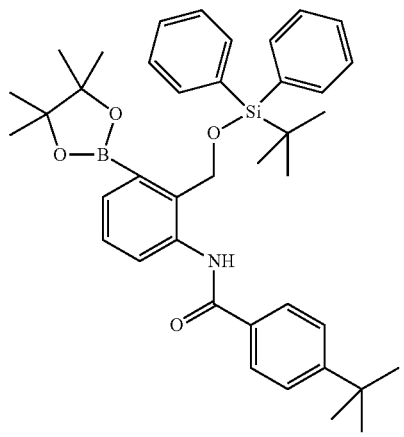 [SMILES: CC(C)(C)c1ccc(C(=O)Nc2cccc(B3OC(C)(C)C(C)(C)O3)c2CO[Si](c2ccccc2)(c2ccccc2)C(C)(C)C)cc1]

The anilino compound Intermediate 27 (92.0 g, 189 mmol) was dissolved in DCM (1.2 l) and triethylamine (80 ml). To the mixture 4-tert-butylbenzoylchloride was added over 5 minutes at 0° C. The mixture was stirred at room temperature for 1 hour. The mixture was washed with saturated ammonium chloride solution and brine (2×) and evaporated. The residue was taken up in hexane and stirred at room temperature for 3 hours. The solid was filtered off to afford compound Intermediate 28 as a beige solid.

MS (ESI): 648 [M+H]$^+$, $^1$H-NMR (CDCl3): δ (ppm) 9.85 (br s, 1H), 7.80 (m, 2H), 7.60 (m, 6H), 7.35-7.25 (m, 9H), 5.30 (s, 2H), 1.35 (s, 9H), 1.05 (s, 18H).

(5) 4-{4-[3-(4-tert-Butyl-benzoylamino)-2-(tert-butyl-diphenyl-silanyloxymethyl)-phenyl]-7H-pyrrolo[2,3-d]pyrimid-6-yl}-3,6-dihydro-2H-pyridin3-1-carboxylic acid tert-butyl ester, Intermediate 29

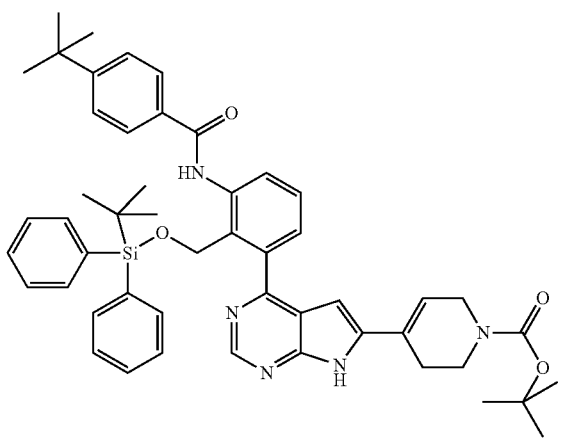 [SMILES: CC(C)(C)OC(=O)N1CC=C(c2cc3c(-c4cccc(NC(=O)c5ccc(C(C)(C)C)cc5)c4CO[Si](c4ccccc4)(c4ccccc4)C(C)(C)C)ncnc3[nH]2)CC1]

For the Suzuki coupling between chloro compound Intermediate 1 (0.50 g, 1.49 mmol) and boronic ester derivative Intermediate 28 (1.45 g, 2.24 mmol) the same procedure was used as described in Example 1 step 6, to afford the compound Intermediate 29 as a beige solid.

MS (ESI): 820 [M+H]$^+$, $^1$H-NMR (DMSO-d$_6$): δ (ppm) 12.33 (s, 1H), 10.02 (s, 1H), 8.68 (s, 1H), 7.78 (m, 2H), 7.75 (m, 1H), 7.46 (m, 2H), 7.40 (m, 1H), 7.25 (m, 2H), 7.12 (m, 1H), 7.11 (m, 8H), 6.54 (br s, 1H), 6.30 (s, 1H), 4.97 (s, 2H), 4.07 (m, 2H), 3.52 (m, 2H), 2.43 (m, 2H), 1.41 (s, 9H), 1.30 (s, 9H), 0.53 (s, 9H).

(6) 4-tert-Butyl-N-{2-(tert-butyl-diphenyl-silanyloxymethyl)-3-[6-(1,2,3,6-tetrahydro-pyridin-4-yl)-7H-pyrrolo[2,3-d]pyrimidin-4-yl]-benzamide, Intermediate 30

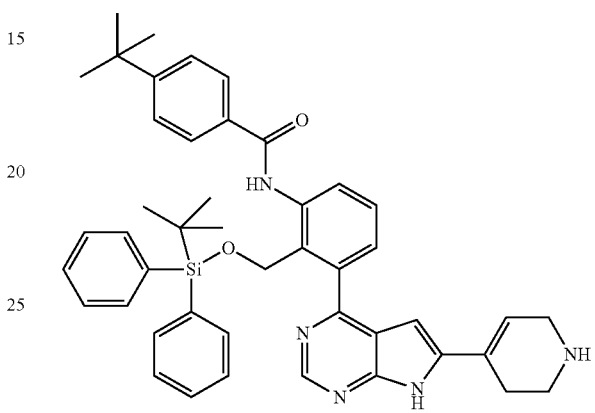

The BOC protecting group of compound Intermediate 29 (0.92 g, 1.12 mmol) was removed as described in Example 1 step 2 to afford the compound Intermediate 30 as a beige solid.

MS (ESI): 720 [M+H]$^+$, $^1$H-NMR (DMSO-d$_6$): δ (ppm) 12.50 (s, 1H), 10.08 (s, 1H), 8.72 (s, 1H), 7.80 (m, 2H), 7.75 (m, 1H), 7.53 (m, 1H), 7.42 (m, 1H), 7.26 (m, 2H), 7.15 (m, 2H), 7.11 (m, 8H), 6.56 (br s, 1H), 6.42 (s, 1H), 4.99 (s, 2H), 3.85 (m, 2H), 3.32 (m, 2H), 2.67 (m, 2H), 1.29 (s, 9H), 0.52 (s, 9H).

(7) 4-{4-[3-(4-tert-Butyl-benzoylamino)-2-(tert-butyl-diphenyl-silanyloxymethyl)-phenyl]-7H-pyrrolo[2,3-d]pyrimidin-6-yl}-3,6-dihydro-2H-pyridine-1-carboxylic acid dimethylamide, Intermediate 31

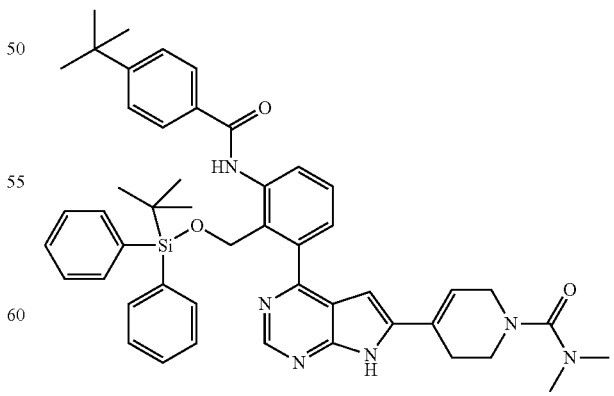

The amino compound Intermediate 30 (0.1 g, 0.14 mmol) was acylated as described in Example 1 step 3 to afford the compound Intermediate 31 as a beige solid.

MS (ESI): 791 [M+H]⁺, ¹H-NMR (DMSO-d₆): δ (ppm) 12.35 (s, 1H), 10.04 (s, 1H), 8.70 (s, 1H), 7.79 (m, 2H), 7.74 (m, 1H), 7.53 (m, 1H), 7.47 (m, 2H), 7.43 (m, 1H), 7.27 (m, 2H), 7.14-7.11 (m, 8H), 6.57 (br s, 1H), 6.30 (s, 1H), 4.98 (s, 2H), 3.91 (m, 2H), 3.32 (m, 2H), 2.76 (s, 6H), 2.52 (m, 2H), 1.31 (s, 9H), 0.53 (s, 9H).

(8) 4-{4-[3-(4-tert-Butyl-benzoylamino)-2-hydroxymethyl-phenyl]-7H-pyrrolo[2,3-d]pyrimidin-6-yl}-3,6-dihydro-2H-pyridine-1-carboxylic acid dimethylamide

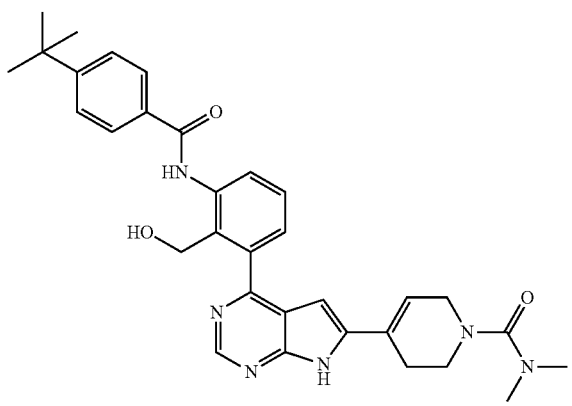 [SMILES: CN(C)C(=O)N1CC=C(c2cc3c(-c4cccc(NC(=O)c5ccc(C(C)(C)C)cc5)c4CO)ncnc3[nH]2)CC1]

The compound Intermediate 31 (65 mg, 0.082 mmol) was dissolved in a 1M solution of tetrabutyl ammonium fluoride in THF (2 ml, 2.0 mmol). The mixture was stirred at room temperature for 20 hours. The solvent was removed under reduced pressure. The residue was purified by flash chromatography on silica (EtOAc/MeOH/NH₄OH 95:5:0.5) to afford the compound Example 37 as a beige solid.

MS (ESI): 553 [M+H]⁺, ¹H-NMR (DMSO-d₆): δ (ppm) 12.44 (s, 1H), 10.53 (s, 1NH) 8.83 (s, 1H), 8.23 (m, 1H), 7.91 (d, 2H), 7.60 (d, 2H), 7.51 (m, 1H), 7.35 (m, 1H), 6.60 (br s, 1H), 6.45 (s, 1H), 4.69 (s, 2H), 3.90 (br s, 2H), 3.33 (m, 2H), 2.77 (s, 6H), 2.54 (m, 2H), 1.33 (s, 9H).

Example 38

4-tert-Butyl-N-(3-{6-[1-(2 fluoro-acetyl)-1,2,3,6-tetrahydro-pyridin-4-yl]-7H-pyrrolo[2,3-d]pyrimidin-4-yl}-2-hydroxymethyl-phenyl)-benzamide

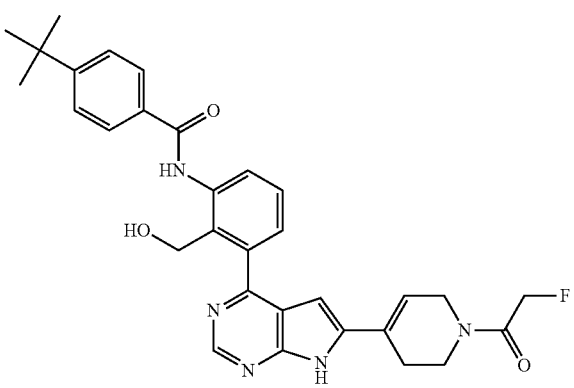 [SMILES: CC(C)(C)c1ccc(C(=O)Nc2cccc(-c3ncnc4[nH]c(C5=CCN(C(=O)CF)CC5)cc34)c2CO)cc1]

(1) 4-tert-Butyl-N-(2-(tert-butyl-diphenyl-silanyloxymethyl)-3-{6-[1-(2-fluoro-acetyl)-1,2,3,6-tetrahydro-pyridin-4-yl]-7H-pyrrolo[2,3-d]pyrimidin-4-yl}-phenyl)-benzamide, Intermediate 32

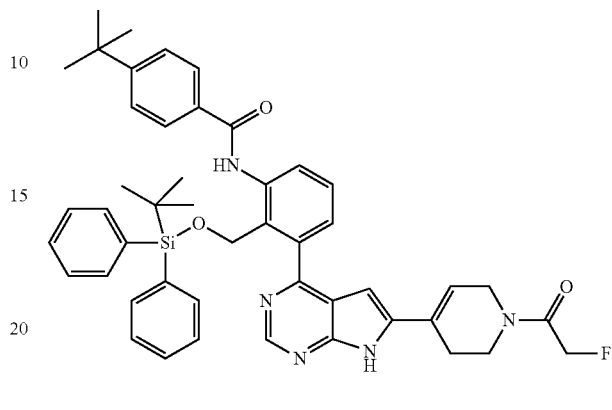

To a solution of Intermediate 30 (100 mg, 0.139 mmol) in pyridine (5 ml) was added fluoro-acetyl chloride (20 mg, 0.208 mmol). The mixture was stirred at r.t. for 20 hrs, then the solvent was removed in vacuo. The crude product was purified using flash chromatography (silica gel, EtOAc/MeOH/NH₃ gradient) to obtain Intermediate 32.

(2) 4-tert-Butyl-N-(3-{6-[1-(2 fluoro-acetyl)-1,2,3,6-tetrahydro-pyridin-4-yl]-7H-pyrrolo[2,3-d]pyrimidin-4-yl}-2-hydroxymethyl-phenyl)-benzamide

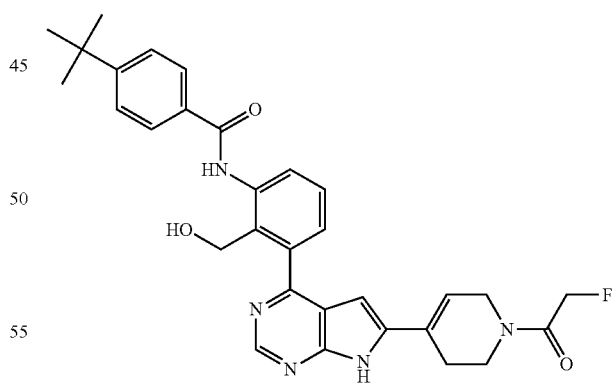

Example 38 was prepared analogue to Example 37 step 8 by replacing Intermediate 31 with Intermediate 32.

MS (ESI): 542 [M+H]⁺, ¹H-NMR (DMSO-d₆): δ (ppm) 12.46 (br s, 1H), 10.52 (s, 1H), 8.83 (s, 1H), 8.21 (d, 1H), 7.90 (d, 2H), 7.59 (d, 2H), 7.50 (t, 1H), 7.34 (d, 1H), 6.61 (br, s), 6.44 (s, 1H), 5.91 (br s, 1H), 5.25 (m, 2H), 4.67 (s, 2H), 4.18 (m, 1H), 4.08 (m, 1H), 3.67 (m, 1H), (3.47 m, 1H), 2.57 (m, 1H), 2.51 (m, 1H), 1.32 (s, 9H).

Example 39

4-(4-{5-Fluoro-3-[2-fluoro-4-(1-hydroxy-1-methyl-ethyl)-benzoylamino]-2-methyl-phenyl}-7H-pyrrolo[2,3-d]pyrimidin-6-yl)-3,6-dihydro-2H-pyridine-1-carboxylic acid dimethylamide

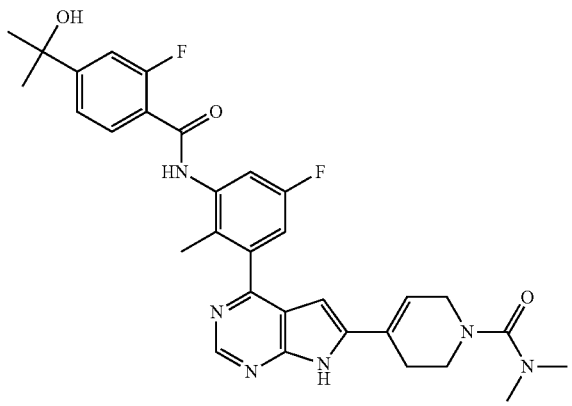 [SMILES: Cc1c(NC(=O)c2ccc(C(C)(C)O)cc2F)cc(F)cc1-c1ncnc2[nH]c(C3=CCN(C(=O)N(C)C)CC3)cc12]

(1) 4-Chlorocarbonyl-3-fluoro-benzoic acid methyl ester, Intermediate 33

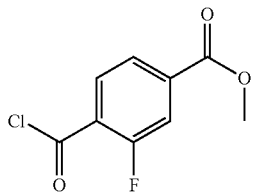

2-Fluoro-terephthalic acid 4-methyl ester (J. Med. Chem., 52(19), 5950-5966; 2009) (500 mg, 2.25 mmol) was suspended in DCM (10 ml). Then oxalyl chloride (5.08 ml, 58.0 mmol) and a drop of DMF were added. The resulting mixture was refluxed for 14 hrs. The solvents were removed in vacuo, and the resulting crude Intermediate 33 was used in the next step without purification.

(2) N-(3-Bromo-5-fluoro-2-methyl-phenyl)-3-fluoro-terephthalamic acid methyl ester, Intermediate 34

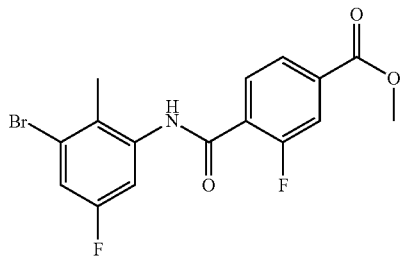 [SMILES: COC(=O)c1ccc(C(=O)Nc2cc(F)cc(Br)c2C)c(F)c1]

3-Bromo-5-fluoro-2-methylaniline (515 mg, 2.53 mmol) was dissolved in pyridine (20 ml). Then Intermediate 33 (547 mg, 2.53 mmol) and DMAP (3.09 mg, 0.025 mmol) were added and the resulting mixture was stirred at r.t. for 2 hrs. The solvents were removed in vacuo and the residue was taken up with EtOAc and H$_2$O. The organic layer was washed with sat. NaHCO$_3$ solution and brine, and then dried over Na$_2$SO$_4$. The solvents were removed in vacuo and the resulting residue was recrystallized with MeOH to afford Intermediate 34 as colorless solid.

(3) N-(3-Bromo-5-fluoro-2-methyl-phenyl)-2-fluoro-4-(1-hydroxy-1-methyl-ethyl)-benzamide, Intermediate 35

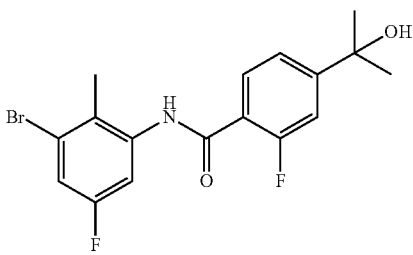 [SMILES: Cc1c(Br)cc(F)cc1NC(=O)c1ccc(C(C)(C)O)cc1F]

Intermediate 34 (75 mg, 0.195 mmol) was dissolved in THF (10 ml) and the resulting mixture was cooled to 0° C. Then methyl magnesium bromide (0.390 ml, 1.17 mmol) was added dropwise and stirring was continued for 3 hrs. The mixture was concentrated to dryness and then diluted with MeOH/DMSO. The resulting precipitate was filtered off to give Intermediate 35 as a white solid.

MS (ESI): 384 [M+H]$^+$, $^1$H-NMR (DMSO-d$_6$): δ (ppm) 10.04 (br s, 1H), 7.63 (m, 1H), 7.42 (m, 2H), 7.36 (m, 2H), 5.27 (s, 1H), 2.24 (s, 3H), 1.40 (s, 6H).

(4) 2-Fluoro-N-[5-fluoro-2-methyl-3-(4,4,5,5-tetramethyl-[1,3,2]dioxaborolan-2-yl)-phenyl]-4-(1-hydroxy-1-methyl-ethyl)-benzamide, Intermediate 36

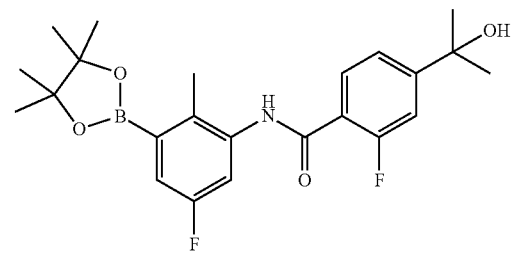 [SMILES: Cc1c(NC(=O)c2ccc(C(C)(C)O)cc2F)cc(F)cc1B1OC(C)(C)C(C)(C)O1]

Intermediate 36 was prepared analogue to Intermediate 4 by replacing 1-bromo-5-fluoro-2-methyl-3-nitro-benzene with Intermediate 35.

(5) 4-(4-{5-Fluoro-3-[2-fluoro-4-(1-hydroxy-1-methyl-ethyl)-benzoylamino]-2-methyl-phenyl}-7H-pyrrolo[2,3-d]pyrimidin-6-yl)-3,6-dihydro-2H-pyridine-1-carboxylic acid dimethylamide

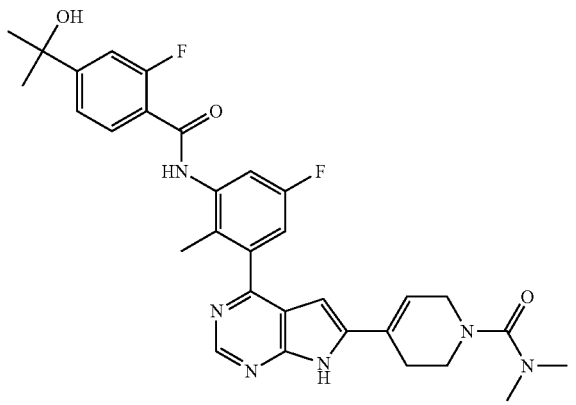 [SMILES: Cc1c(NC(=O)c2ccc(C(C)(C)O)cc2F)cc(F)cc1-c1ncnc2[nH]c(C3=CCN(C(=O)N(C)C)CC3)cc12]

Example 39 was prepared analogue to Example 37 by replacing the boronic ester Intermediate 28 in step 5 with the boronic ester Intermediate 36.

MS (ESI): 575 [M+H]$^+$, $^1$H-NMR (DMSO-d$_6$): δ (ppm) 12.43 (s, 1H), 9.93 (s, 1H), 8.83 (s, 1H), 7.74 (m, 1H), 7.64 (d, 1H), 7.43 (m, 2H), 7.18 (dd, 1H), 6.60 (s, 1H), 6.34 (s, 1H), 5.30 (s, 1H), 3.90 (m, 2H), 3.33 (m, 2H), 2.77 (s, 6H), 2.54 (m, 2H), 2.15 (s, 3H), 1.46 (s, 6H).

Example 40

4-tert-Butyl-N-{5-fluoro-2-methyl-3-[6-(1,2,3,6-tetrahydro-pyridin-4-yl)-7H-pyrrolo[2,3-d]pyrimidin-4-yl]-phenyl}-benzamide

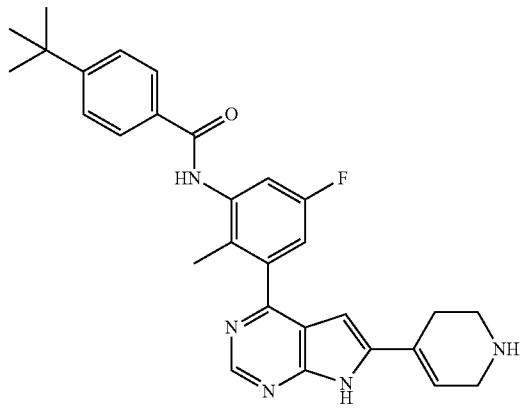 [SMILES: Cc1c(NC(=O)c2ccc(C(C)(C)C)cc2)cc(F)cc1-c1ncnc2[nH]c(C3=CCNCC3)cc12]

(1) N-(3-Bromo-5-fluoro-2-methyl-phenyl)-4-tert-butyl-benzamide, Intermediate 37

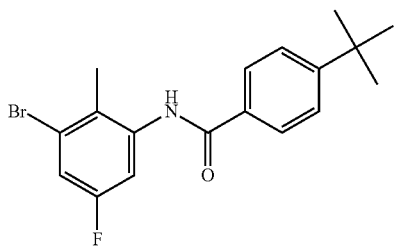 [SMILES: Cc1c(Br)cc(F)cc1NC(=O)c1ccc(C(C)(C)C)cc1]

Intermediate 37 was prepared analogue to Intermediate 34 by replacing Intermediate 33 with 4-tert-butyl-benzoyl chloride.

MS (ESI): 364 [M+H]$^+$, $^1$H-NMR (DMSO-d$_6$): δ (ppm) 10.11 (br s, 1H), 7.90 (d, 2H), 7.55 (d, 2H), 7.49 (d, 1H), 7.32 (d, 1H), 2.32 (s, 3H), 1.38 (s, 9H).

(2) 4-tert-Butyl-N-[5-fluoro-2-methyl-3-(4,4,5,5-tetramethyl-[1,3,2]dioxaborolan-2-yl)-phenyl]-benzamide, Intermediate 38

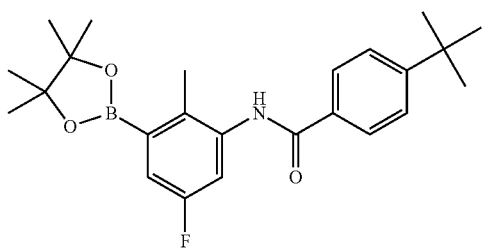 [SMILES: Cc1c(NC(=O)c2ccc(C(C)(C)C)cc2)cc(F)cc1B1OC(C)(C)C(C)(C)O1]

Intermediate 38 was prepared analogue to Intermediate 4 by replacing 1-bromo-5-fluoro-2-methyl-3-nitro-benzene with Intermediate 37.

MS (ESI): 412 [M+H]$^+$, $^1$H-NMR (DMSO-d$_6$): δ (ppm) 9.85 (br s, 1H), 7.90 (d, 2H), 7.55 (d, 2H), 7.35 (d, 1H), 7.22 (d, 1H), 2.35 (s, 3H), 1.40 (s, 6H), 1.32 (m, 15H).

(3) 4-tert-Butyl-N-{5-fluoro-2-methyl-3-[6-(1,2,3,6-tetrahydro-pyridin-4-yl)-7H-pyrrolo[2,3-d]pyrimidin-4-yl]-phenyl}-benzamide

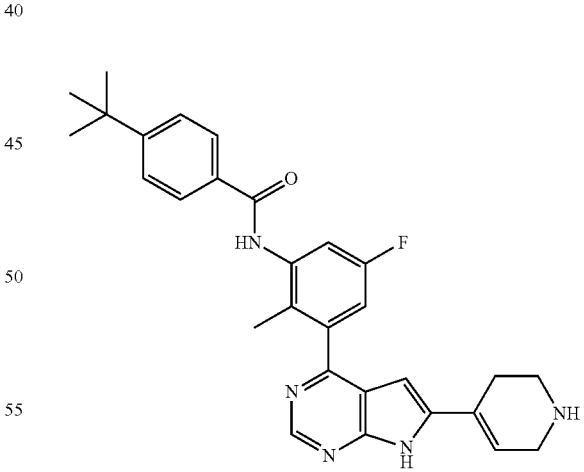

Example 40 was prepared analogue to Intermediate 30 in Example 37 step 6 by replacing Intermediate 28 in Example 37 step 5 with Intermediate 38.

MS (ESI): 484 [M+H]$^+$, $^1$H-NMR (DMSO-d$_6$): δ (ppm) 12.55 (s, 1H), 9.98 (s, 1H), 8.85 (s, 1H), 8.71 (br s, 1H), 7.92 (d, 2H), 7.56 (d, 2H), 7.50 (m, 1H), 7.18 (m, 1H), 6.56 (m, 1H), 6.43 (s, 1H), 3.80 (m, 2H), 3.28 (m, 2H), 2.67 (m, 2H), 2.10 (s, 3H), 1.32 (s, 9H).

Example 41

4-{4-[3-(4-tert-Butyl-benzoylamino)-5-fluoro-2-methyl-phenyl]-7H-pyrrolo[2,3-d]pyrimidin-6-yl}-3,6-dihydro-2H-pyridine-1-carboxylic acid dimethylamide

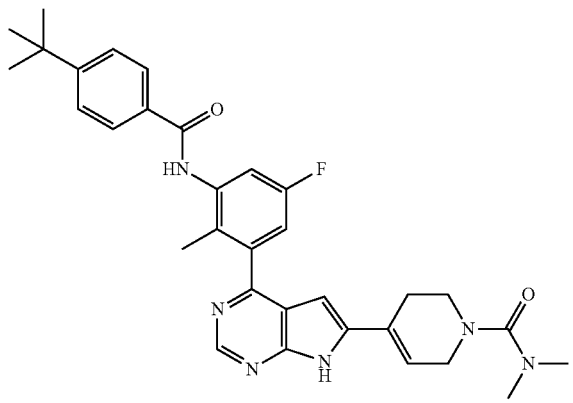 [SMILES: Cc1c(NC(=O)c2ccc(C(C)(C)C)cc2)cc(F)cc1-c1ncnc2[nH]c(C3=CCN(C(=O)N(C)C)CC3)cc12]

Example 41 was prepared analogue to Example 37 step 7 by replacing Intermediate 30 with Example 40.

MS (ESI): 555 [M+H]$^+$, $^1$H-NMR (DMSO-d$_6$): δ (ppm) 12.44 (s, 1H), 9.98 (s, 1H), 8.83 (s, 1H), 7.95 (d, 2H), 7.58 (d, 2H), 7.48 (m, 1H), 7.22 (m, 1H), 6.60 (s, 1H), 6.33 (s, 1H), 5.30 (s, 1H), 3.90 (m, 2H), 3.32 (m, 2H), 2.77 (s, 6H), 2.55 (m, 2H), 2.12 (s, 3H), 1.34 (s, 9H).

Example 42

4-tert-Butyl-N-{5-fluoro-3-[6-(1-methanesulfonyl-1,2,3,6-tetrahydro-pyridin-4-yl)-7H-pyrrolo[2,3-d]pyrimidin-4-yl]-2-methyl-phenyl}-benzamide

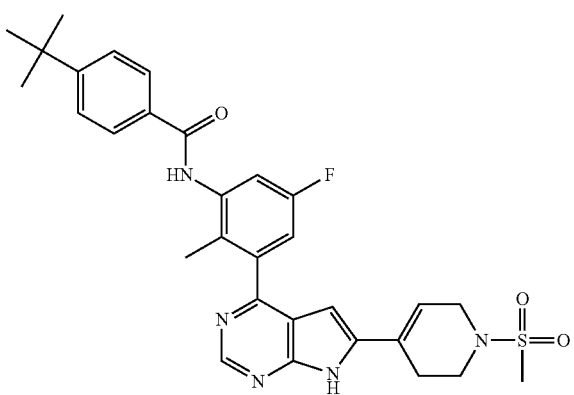 [SMILES: Cc1c(NC(=O)c2ccc(C(C)(C)C)cc2)cc(F)cc1-c1ncnc2[nH]c(C3=CCN(S(C)(=O)=O)CC3)cc12]

To a solution of Example 40 (90 mg, 0.186 mmol) and DIPEA (0.098 ml, 0.558 mmol) in THF (10 ml) was added methanesulfonyl chloride (0.015 ml, 0.186 mmol) dropwise. The resulting mixture was stirred at r.t. for 1 hr, then quenched with water and diluted with EtOAc. The organic layer was washed with sat. aqueous NaHCO$_3$ solution and brine, dried with Na$_2$SO$_4$, and filtered. The solvents were removed in vacuo, and the crude product was purified by reversed phase HPLC (MeCN/H$_2$O gradient) to yield Example 42 as a light yellow solid.

MS (ESI): 562 [M+H]$^+$, $^1$H-NMR (DMSO-d$_6$): δ (ppm) 12.48 (br s, 1H), 9.97 (s, 1H), 8.82 (s, 1H), 7.93 (d, 2H), 7.56 (d, 2H), 7.46 (m, 1H), 7.19 (m, 1H), 6.61 (s, 1H), 6.36 (s, 1H), 3.92 (m, 2H), 3.31 (m, 2H), 2.94 (s, 3H), 2.62 (m, 2H), 2.10 (s, 3H), 1.31 (s, 9H).

Example 43

4-tert-Butyl-N-{3-[6 (1 dimethylsulfamoyl-1,2,3,6-tetrahydro-pyridin-4-yl)-7H-pyrrolo[2,3-d]pyrimidin-4-yl]-5-fluoro-2-methyl-phenyl}-benzamide

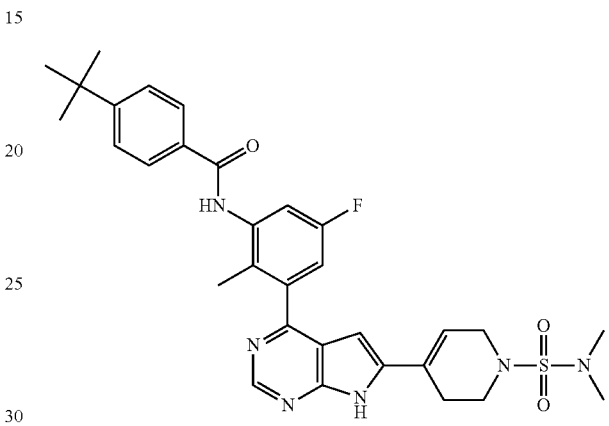

Example 43 was prepared analogue to Example 42 by replacing methanesulfonyl chloride with N,N-dimethylamidosulfamoyl chloride.

MS (ESI): 591 [M+H]$^+$, $^1$H-NMR (DMSO-d$_6$): δ (ppm) 12.48 (br s, 1H), 9.97 (s, 1H), 8.82 (s, 1H), 7.93 (d, 2H), 7.56 (d, 2H), 7.46 (m, 1H), 7.20 (m, 1H), 6.59 (s, 1H), 6.34 (s, 1H), 3.93 (m, 2H), 3.40 (m, 2H), 2.76 (s, 6H), 2.57 (m, 2H), 2.09 (s, 3H), 1.31 (s, 9H).

Example 44

4-tert-Butyl-N-{3-[6-(1 methanesulfonyl-1,2,3,6-tetrahydro-pyridin-4-yl)-7H-pyrrolo[2,3-d]pyrimidin-4-yl]-2-methyl-phenyl}-benzamide

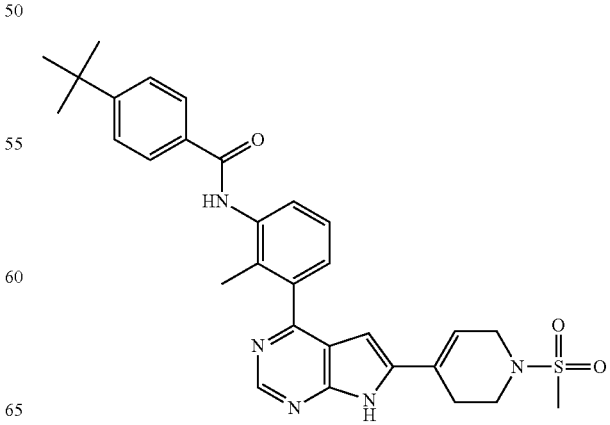

(1) 4-tert-Butyl-N-{2-methyl-3-[6-(1,2,3,6-tetrahydro-pyridin-4-yl)-7H-pyrrolo[2,3-d]pyrimidin-4-yl]-phenyl}-benzamide, Intermediate 39

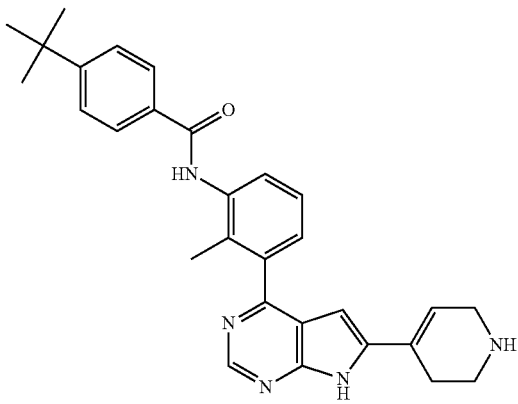 [SMILES: Cc1c(NC(=O)c2ccc(C(C)(C)C)cc2)cccc1-c1ncnc2[nH]c(C3=CCNCC3)cc12]

Intermediate 39 was prepared analogue to Intermediate 30 in Example 37 step 6 by replacing Intermediate 28 in Example 37 step 5 with Intermediate 48.

MS (ESI): 465 [M+H]$^+$, $^1$H-NMR (DMSO-d$_6$): δ (ppm) 12.29 (br s, 1H), 9.92 (s, 1H), 8.78 (s, 1H), 7.94 (d, 2H), 7.53 (d, 2H), 7.45 (m, 1H), 7.37 (m, 2H), 6.60 (br s, 1H), 6.20 (s, 1H), 3.40 (m, 2H), 2.88 (m, 2H), 2.32 (m, 2H), 2.13 (s, 3H), 1.31 (s, 9H).

(2) 4-tert-Butyl-N-{3-[6 (1 methanesulfonyl-1,2,3,6-tetrahydro-pyridin-4-yl)-7H-pyrrolo[2,3-d]pyrimidin-4-yl]-2-methyl-phenyl}-benzamide

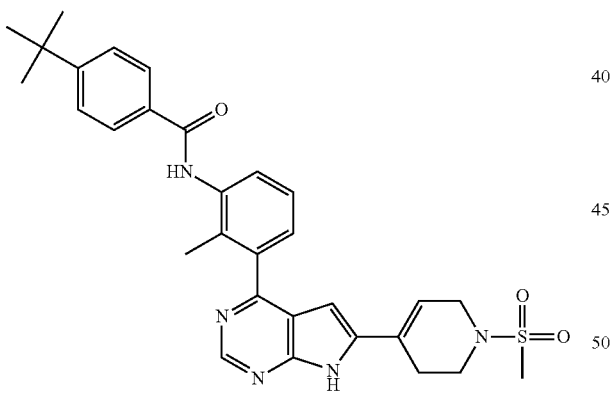

To a solution of Intermediate 39 (80 mg, 0.172 mmol) and TEA (0.048 ml, 0.344 mmol) in DCM was added methanesulfonyl chloride (0.021 ml, 0.258 mmol) dropwise. The resulting mixture was stirred at r.t. for 16 hrs, then quenched with water, and extracted with EtOAc. The organic layer was dried with Na$_2$SO$_4$ and filtered. The solvents were removed in vacuo, and the crude product was purified by flash chromatography (silica gel, EtOAc/MeOH/N H$_3$ gradient) to yield Example 44.

MS (ESI): 544 [M+H]$^+$, $^1$H-NMR (DMSO-d$_6$): δ (ppm) 12.34 (br s, 1H), 9.92 (s, 1H), 8.81 (s, 1H), 7.94 (d, 2H), 7.54 (d, 2H), 7.46 (m, 1H), 7.37 (m, 2H), 6.60 (br s, 1H), 6.31 (s, 1H), 3.92 (m, 2H), 3.36 (m, 2H), 2.93 (s, 3H), 2.61 (m, 2H), 2.14 (s, 3H), 1.32 (s, 9H).

Example 45

4-{4-[3-(6-tert-Butyl-1-oxo-3,4-dihydro-1H-isoquinolin-2-yl)-2-hydroxymethyl-phenyl]-7H-pyrrolo[2,3-d]pyrimidin-6-yl}-3,6-dihydro-2H-pyridine-1-carboxylic acid dimethylamide

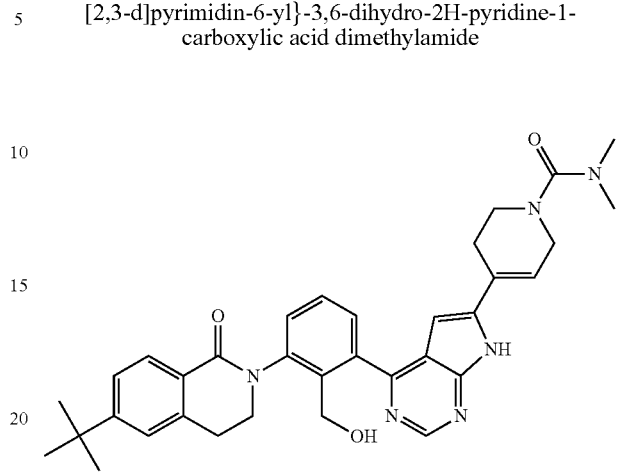

(1) Acetic acid 2-(6-tert-butyl-1-oxo-3,4-dihydro-1H-isoquinolin-2-yl)-6-(4,4,5,5-tetramethyl-1-[1,3,2]dioxaborolan-2-yl)-benzyl ester, Intermediate 40

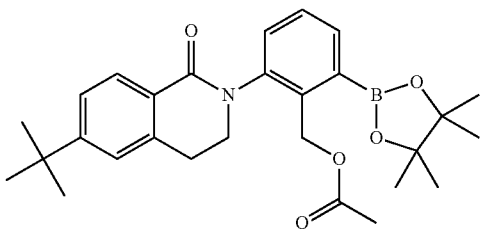 [SMILES: CC(=O)OCc1c(B2OC(C)(C)C(C)(C)O2)cccc1N1CCc2cc(C(C)(C)C)ccc2C1=O]

Intermediate 40 was prepared analogue to Intermediate 4 by replacing 1-bromo-5-fluoro-2-methyl-3-nitro-benzene with acetic acid 2-bromo-6-(6-tert-butyl-1-oxo-3,4-dihydro-1H-isoquinolin-2-yl)-benzyl ester (WO2010/000633).

(2) 4-{4-[3-(6-tert-Butyl-1-oxo-3,4-dihydro-1H-isoquinolin-2-yl)-2-hydroxymethyl-phenyl]-7H-pyrrolo[2,3-d]pyrimidin-6-yl}-3,6-dihydro-2H-pyridine-1-carboxylic acid dimethylamide

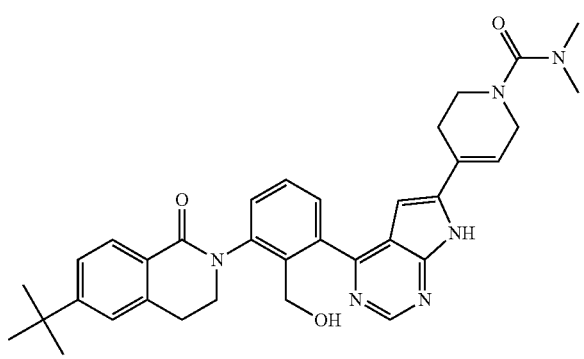 [SMILES: CN(C)C(=O)N1CC=C(c2cc3c(-c4cccc(N5CCc6cc(C(C)(C)C)ccc6C5=O)c4CO)ncnc3[nH]2)CC1]

Example 45 was prepared analogue to Intermediate 6 by replacing Intermediate 5 with Intermediate 40.

MS (ESI): 579 [M+H]+, 1H-NMR (DMSO-d6): δ (ppm) 8.83 (s, 1H), 7.88 (m, 1H), 7.68 (m, 1H), 7.58 (m, 1H), 7.44 (m, 1H), 7.42 (m, 1H), 6.61 (s, 1H), 6.58 (s, 1H), 5.24 (m, 1H), 4.39 (m, 2H), 4.02 (m, 1H), 3.92 (m, 2H), 3.89 (m, 1H), 3.36 (m, 2H), 3.29 (m, 1H), 3.13 (m, 1H), 2.78 (s, 6H), 2.55 (m, 2H), 1.33 (s, 9H).

Example 46

4-{4-[3-(6-Cyclopropyl-1-oxo-3,4-dihydro-1H-iso-quinolin-2-yl)-2-hydroxymethyl-phenyl]-7H-pyrrolo[2,3-d]pyrimidin-6-yl}-3,6-dihydro-2H-pyridine-1-carboxylic acid dimethylamide

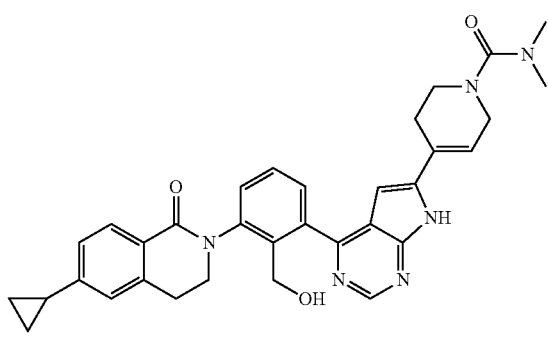 [SMILES: CN(C)C(=O)N1CC=C(c2cc3c(-c4cccc(N5CCc6cc(C7CC7)ccc6C5=O)c4CO)ncnc3[nH]2)CC1]

(1) Acetic acid 2-(6-cyclopropyl-1-oxo-3,4-dihydro-1H-isoquinolin-2-yl)-6-(4,4,5,5-tetramethyl-[1,3,2]dioxaborolan-2-yl)-benzyl ester, Intermediate 41

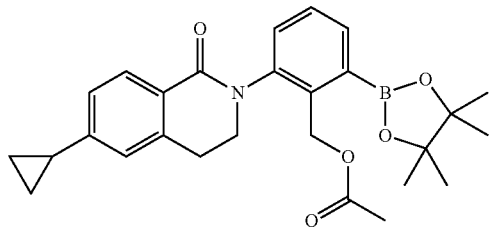 [SMILES: CC(=O)OCc1c(B2OC(C)(C)C(C)(C)O2)cccc1N1CCc2cc(C3CC3)ccc2C1=O]

Intermediate 41 was prepared analogue to Intermediate 4 by replacing 1-bromo-5-fluoro-2-methyl-3-nitro-benzene with acetic acid 2-bromo-6-(6-cyclopropyl-1-oxo-3,4-dihydro-1H-isoquinolin-2-yl)-benzyl ester (WO2010/000633).

(2) 4-{4-[3-(6-Cyclopropyl-1-oxo-3,4-dihydro-1H-isoquinolin-2-yl)-2-hydroxymethyl-phenyl]-7H-pyrrolo[2,3-d]pyrimidin-6-yl}-3,6-dihydro-2H-pyridine-1-carboxylic acid dimethylamide

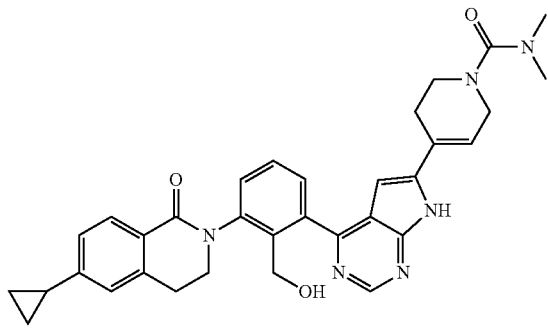 [SMILES: CN(C)C(=O)N1CC=C(c2cc3c(-c4cccc(N5CCc6cc(C7CC7)ccc6C5=O)c4CO)ncnc3[nH]2)CC1]

Example 46 was prepared analogue to Intermediate 6 by replacing Intermediate 5 with Intermediate 41.

MS (ESI): 563 [M+H]+, 1H-NMR (DMSO-d6): δ (ppm) 8.81 (s, 1H), 7.80 (d, 1H), 7.66 (d, 1H), 7.56 (t, 1H), 7.50 (d, 1H), 7.09 (m, 1H), 7.08 (m, 1H), 6.60 (s, 1H), 6.54 (s, 1H), 5.15 (m, 1H), 4.36 (m, 2H), 3.98 (m, 1H), 3.91 (m, 2H), 3.89 (m, 1H), 3.35 (m, 2H), 3.24 (m, 1H), 3.09 (m, 1H), 2.77 (s, 6H), 2.55 (m, 2H), 2.00 (m, 1H), 1.04 (m, 2H), 0.78 (m, 2H).

Example 47

4-(4-{2-Hydroxymethyl-3-[6-(1-hydroxy-1-methyl-ethyl)-1-oxo-3,4-dihydro-1H-isoquinolin-2-yl]-phenyl}-7H-pyrrolo[2,3-d]pyrimidin-6-yl)-3,6-dihydro-2H-pyridine-1-carboxylic acid dimethylamide

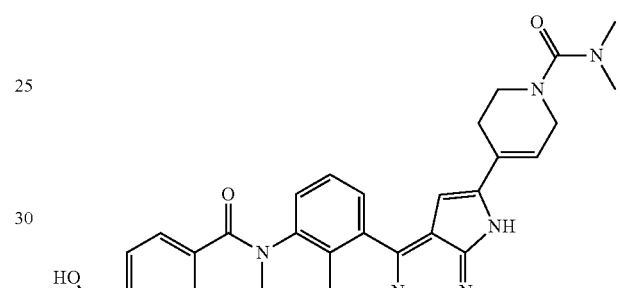

(1) 2-Bromo-6-[6-(1-hydroxy-1-methyl-ethyl)-1-oxo-3,4-dihydro-1H-isoquinolin-2-yl]-benzaldehyde, Intermediate 42

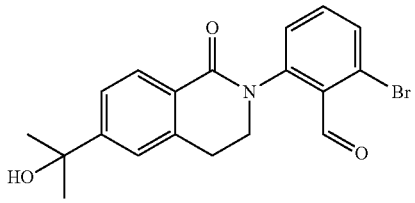

To a mixture of 2,6-dibromo-benzaldehyde (1.60 g, 6.06 mmol), Pd2(dba)3 (222 mg, 0.243 mmol), xantphos (210 mg, 0.364 mmol), and Cs2CO3 (2.77 g, 8.49 mmol) in dioxane (60 ml) under argon was added 6-(1-hydroxy-1-methyl-ethyl)-3,4-dihydro-2H-isoquinolin-1-one (US2009/0306041) (995 mg, 4.85 mmol). The resulting mixture was refluxed overnight. After cooling down to r.t., water was added, and the mixture was extracted three times with EtOAc. The combined organic layers were dried, filtered, and evaporated to dryness. The crude product was purified by flash chromatography (silica gel, cyclohexane/EtOAC gradient) to yield Intermediate 42.

(2) 2-(3-Bromo-2-hydroxymethyl-phenyl)-6-(1-hydroxy-1-methyl-ethyl)-3,4-dihydro-2H-isoquinolin-1-one, Intermediate 43

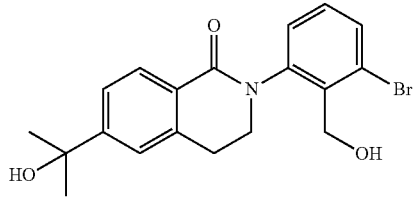 [SMILES: CC(C)(O)c1ccc2c(c1)CCN(c1cccc(Br)c1CO)C2=O]

To a solution of Intermediate 42 (320 mg, 0.824 mmol) in THF (10 ml) under argon atmosphere was added lithium triethylborohydride (1M in THF, 0.989 ml, 0.989 mmol) dropwise. The resulting mixture was stirred for 2 hrs at r.t. before adding sat. aqueous NaHCO$_3$ solution (5 ml). Additional water was added and the mixture was extracted three times with EtOAc. The combined organic layers were dried, filtered, and evaporated to dryness. The crude product was purified by flash chromatography (silica gel, cyclohexane/EtOAC gradient) to yield Intermediate 43.

MS (ESI): 390 [M+H]$^+$, $^1$H-NMR (DMSO-d$_6$): δ (ppm) 7.83 (d, 1H), 7.63 (d, 1H), 7.48 (m, 1H), 7.47 (s, 1H), 7.36 (m, 1H), 7.34 (m, 1H), 5.16 (s, 1H), 4.92 (m, 1H), 4.53 (m, 1H), 4.46 (m, 1H), 3.96 (m, 1H), 3.77 (m, 1H), 3.25 (m, 1H), 3.07 (m, 1H), 1.45 (s, 6H).

(3) Acetic acid 2-bromo-6-[6-(1-hydroxy-1-methyl-ethyl)-1-oxo-3,4-dihydro-1H-isoquinolin-2-yl]-benzyl ester, Intermediate 44

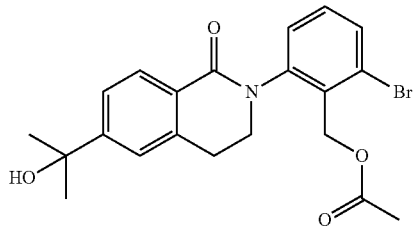 [SMILES: CC(=O)OCc1c(Br)cccc1N1CCc2cc(C(C)(C)O)ccc2C1=O]

To a solution of Intermediate 43 (238 mg, 0.610 mmol) in DCM (6 ml) were added TEA (0.085 ml, 0.610 mmol), DMAP (7.5 mg, 0.061 mmol), and acetic anhydride (62 mg, 0.610 mmol). The resulting mixture was stirred for 24 hrs at r.t. The solvents were removed in vacuo and the crude product was purified by flash chromatography (silica gel, cyclohexane/EtOAC gradient) to yield Intermediate 44.

MS (ESI): 432 [M+H]$^+$, $^1$H-NMR (DMSO-d$_6$): δ (ppm) 7.82 (d, 1H), 7.70 (m, 1H), 7.47 (m, 3H), 7.44 (m, 1H), 5.16 (s, 1H), 5.11 (m, 1H), 5.04 (m, 1H), 4.03 (m, 1H), 3.67 (m, 1H), 3.18 (m, 1H), 3.09 (m, 1H), 1.97 (s, 3H), 1.45 (s, 6H).

(4) Acetic acid 2-[6-(1-hydroxy-1-methyl-ethyl)-1-oxo-3,4-dihydro-1H-isoquinolin-2-yl]-6-(4,4,5,5-tetramethyl-1-[1,3,2]dioxaborolan-2-yl)-benzyl ester, Intermediate 45

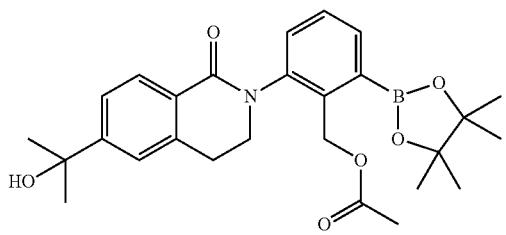 [SMILES: CC(=O)OCc1c(B2OC(C)(C)C(C)(C)O2)cccc1N1CCc2cc(C(C)(C)O)ccc2C1=O]

Intermediate 45 was prepared analogue to Intermediate 4 by replacing 1-bromo-5-fluoro-2-methyl-3-nitro-benzene with Intermediate 44.

MS (ESI): no peaks, $^1$H-NMR (DMSO-d$_6$): δ (ppm) 7.82 (d, 1H), 7.66 (m, 1H), 7.48-7.46 (m, 4H), 5.29 (d, 1H), 5.15 (s, 1H), 4.99 (d, 1H), 4.02 (m, 1H), 3.65 (m, 1H), 3.16 (m, 1H), 3.09 (m, 1H), 1.92 (s, 3H), 1.45 (s, 6H), 1.31 (s, 12H).

(5) 4-(4-{2-Hydroxymethyl-3-[6-(1-hydroxy-1-methyl-ethyl)-1-oxo-3,4-dihydro-1H-isoquinolin-2-yl]-phenyl}-7H-pyrrolo[2,3-d]pyrimidin-6-yl)-3,6-dihydro-2H-pyridine-1-carboxylic acid dimethylamide

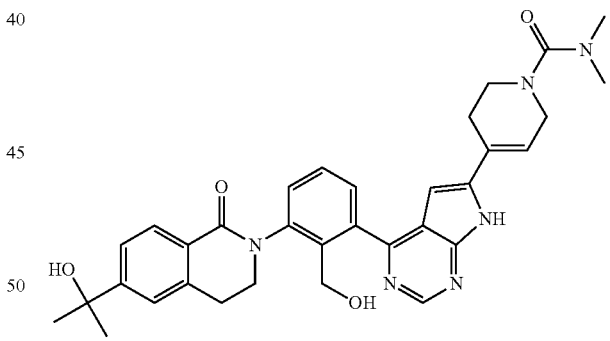

Example 47 was prepared analogue to Intermediate 6 by replacing Intermediate 5 with Intermediate 45, followed by basic removal of the acetate protecting group with LiOH in MeOH/water.

MS (ESI): 581 [M+H]$^+$, $^1$H-NMR (DMSO-d$_6$): δ (ppm) 12.47 (br s, 1H), 8.82 (s, 1H), 7.86 (d, 1H), 7.66 (d, 1H), 7.57 (t, 1H), 7.49 (m, 3H), 6.60 (s, 1H), 6.55 (s, 1H), 5.21 (m, 1H), 5.16 (s, 1H), 4.37 (m, 2H), 4.02 (m, 1H), 3.90 (m, 2H), 3.35-3.25 (m, 3H), 3.13 (m, 1H), 2.77 (s, 6H), 2.55 (m, 2H), 1.46 (s, 6H).

Example 48

4-tert-Butyl-N-{3-[6-(3,6-dihydro-2H-pyran-4-yl)-7H-pyrrolo[2,3-d]pyrimidin-4-yl]-2-hydroxymethyl-phenyl}-benzamide

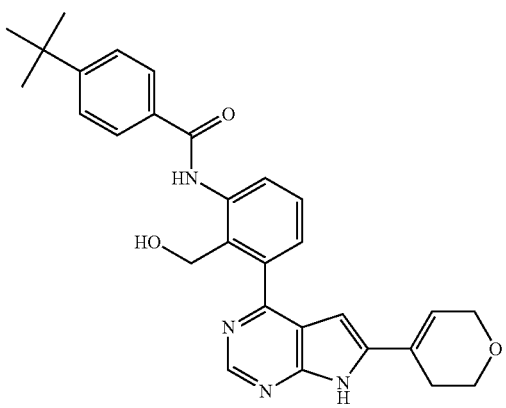 [SMILES: CC(C)(C)c1ccc(C(=O)Nc2cccc(-c3ncnc4[nH]c(C5=CCOCC5)cc34)c2CO)cc1]

Example 48 was prepared analogue to Intermediate 29 by replacing Intermediate 1 with Intermediate 11, followed by removal of the TBDPS protecting group with TBAF in THF.

MS (ESI): 483 [M+H]$^+$, $^1$H-NMR (DMSO-d$_6$): δ (ppm) 12.44 (br s, 1H), 10.52 (s, 1H), 8.82 (s, 1H), 8.21 (d, 1H), 7.90 (d, 2H), 7.58 (d, 2H), 7.50 (t, 1H), 7.35 (d, 1H), 6.64 (br s, 1H), 6.42 (s, 1H), 5.91 (m, 1H), 4.68 (d, 2H), 4.28 (m, 2H), 3.81 (m, 2H), 2.46 (m, 2H), 1.32 (s, 9H).

Example 49

4-tert-Butyl-N-{3-[6-(3,6-dihydro-2H-pyran-4-yl)-7H-pyrrolo[2,3-d]pyrimidin-4-yl]-5-fluoro-2-methyl-phenyl}-benzamide

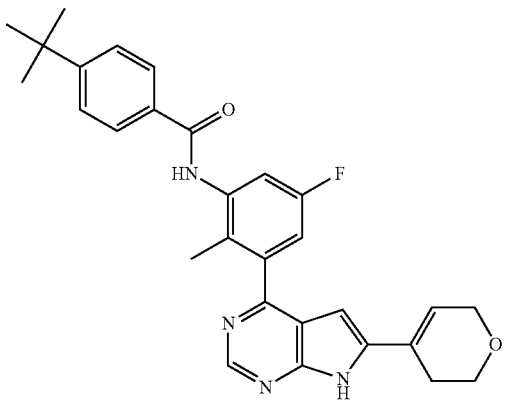 [SMILES: Cc1c(NC(=O)c2ccc(C(C)(C)C)cc2)cc(F)cc1-c1ncnc2[nH]c(C3=CCOCC3)cc12]

Example 49 was prepared analogue to Intermediate 6 by replacing Intermediate 3 with Intermediate 11 and Intermediate 5 with Intermediate 38.

MS (ESI): 485 [M+H]$^+$, $^1$H-NMR (DMSO-d$_6$): δ (ppm) 12.44 (br s, 1H), 9.97 (s, 1H), 8.82 (s, 1H), 7.94 (d, 2H), 7.57 (d, 2H), 7.50 (m, 1H), 7.20 (m, 1H), 6.64 (s, 1H), 6.32 (s, 1H), 4.28 (s, 2H), 3.80 (m, 2H), 2.47 (m, 2H), 2.11 (s, 3H), 1.32 (s, 9H).

Example 50

N-{3-[6-(3,6-Dihydro-2H-pyran-4-yl)-7H-pyrrolo[2,3-d]pyrimidin-4-yl]-5-fluoro-2-methyl-phenyl}-4-dimethylamino-benzamide

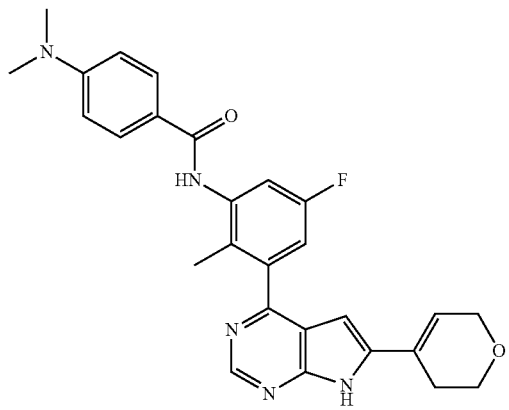 [SMILES: Cc1c(NC(=O)c2ccc(N(C)C)cc2)cc(F)cc1-c1ncnc2[nH]c(C3=CCOCC3)cc12]

(1) N-(3-Bromo-5-fluoro-2-methyl-phenyl)-4-dimethylamino-benzamide, Intermediate 46

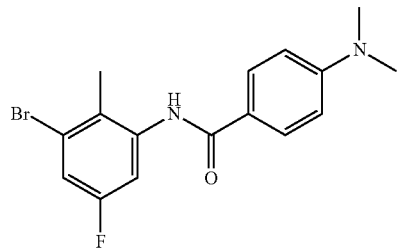 [SMILES: Cc1c(Br)cc(F)cc1NC(=O)c1ccc(N(C)C)cc1]

Intermediate 46 was prepared analogue to Intermediate 34 by replacing Intermediate 33 with 4-dimethylamino-benzoyl chloride.

MS (ESI): 353 [M+H]$^+$, $^1$H-NMR (DMSO-d$_6$): δ (ppm) 9.77 (br s, 1H), 7.85 (d, 2H), 7.45 (d, 1H), 7.31 (d, 1H), 6.77 (d, 2H), 3.00 (s, 6H), 2.24 (s, 3H).

(2) 4-Dimethylamino-N-[5-fluoro-2-methyl-3-(4,4,5,5-tetramethyl-[1,3,2]dioxaborolan-2-yl)-phenyl]-benzamide, Intermediate 47

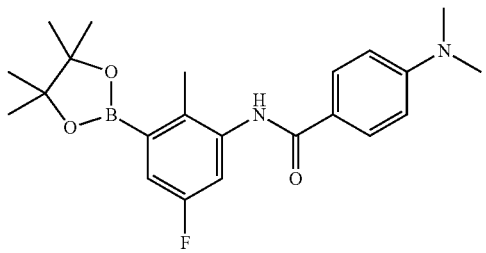

Intermediate 47 was prepared analogue to Intermediate 4 by replacing 1-bromo-5-fluoro-2-methyl-3-nitro-benzene with Intermediate 46.

(3) N-{3-[6-(3,6-Dihydro-2H-pyran-4-yl)-7H-pyrrolo[2,3-d]pyrimidin-4-yl]-5-fluoro-2-methyl-phenyl}-4-dimethylamino-benzamide

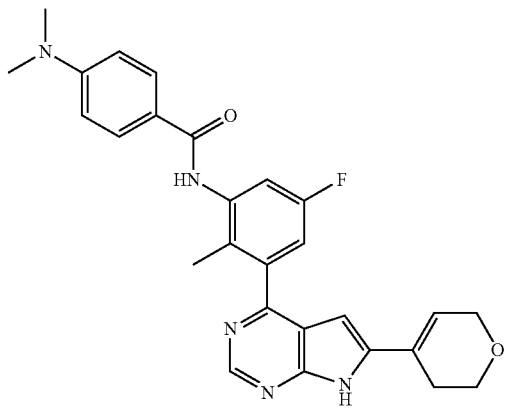 [SMILES: Cc1c(NC(=O)c2ccc(N(C)C)cc2)cc(F)cc1-c1ncnc2[nH]c(C3=CCOCC3)cc12]

Example 50 was prepared analogue to Example 49 by replacing Intermediate 38 with Intermediate 47.

MS (ESI): 472 [M+H]⁺, ¹H-NMR (DMSO-d₆): δ (ppm) 12.43 (br s, 1H), 9.64 (s, 1H), 8.82 (s, 1H), 7.88 (d, 2H), 7.46 (d, 1H), 7.15 (d, 1H), 6.78 (d, 2H), 6.64 (s, 1H), 6.31 (s, 1H), 4.28 (s, 2H), 3.80 (m, 2H), 3.00 (s, 6H), 2.47 (m, 2H), 2.10 (s, 3H).

Example 51

4-tert-Butyl-N-{3-[6-(3,6-dihydro-2H-thiopyran-4-yl)-7H-pyrrolo[2,3-d]pyrimidin-4-yl]-2-methyl-phenyl}-benzamide

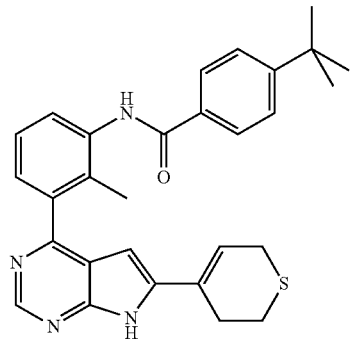

(1) 4-tert-Butyl-N-[2-methyl-3-(4,4,5,5-tetramethyl-1-[1,3,2]dioxaborolan-2-yl)-phenyl]-benzamide, Intermediate 48

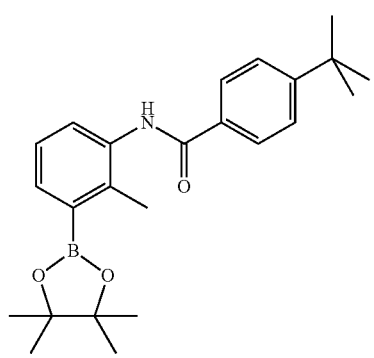 [SMILES: Cc1c(NC(=O)c2ccc(C(C)(C)C)cc2)cccc1B1OC(C)(C)C(C)(C)O1]

To a solution of 2-methyl-3-(4,4,5,5-tetramethyl-[1,3,2]dioxaborolan-2-yl)-phenylamine (370.0 g, 1.58 mol) in DCM (4 l) and triethylamine (330 ml, 2.38 mol), 4-tert-butylbenzoyl chloride (290 ml, 1.58 mol) was added dropwise over 25 minutes at 0° C. The mixture was stirred at room temperature for 1 hour. The mixture was washed with water, saturated sodium hydrogen carbonate solution and brine. The organic layer was dried over sodium sulfate and evaporated. The residue was taken up in heptane (1 l) and stirred at room temperature for 1 hour. The solid was filtered off and dried to afford Intermediate 48 as a beige solid.

MS (ESI): 394 [M+H]⁺, ¹H-NMR (DMSO-d₆): δ (ppm) 9.80 (s, 1H), 7.92 (d, 2H), 7.56 (d, 2H), 7.38 (m, 2H), 7.20 (m, 1H), 2.36 (s, 3H), 1.31 (s, 21H).

(2) 4-tert-Butyl-N-{3-[6-(3,6-dihydro-2-H-thiopyran-4-yl)-7H-pyrrolo[2,3-d]pyrimidin-4-yl]-2-methyl-phenyl}-benzamide

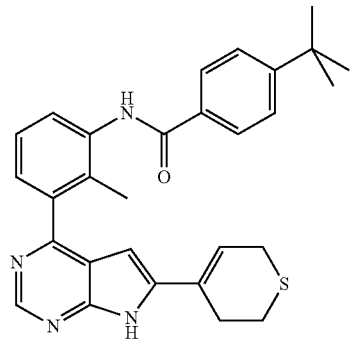 [SMILES: Cc1c(NC(=O)c2ccc(C(C)(C)C)cc2)cccc1-c1ncnc2[nH]c(C3=CCSCC3)cc12]

For the Suzuki coupling between chloride Intermediate 15 (0.25 g, 0.99 mmol) and the boronic ester Intermediate 48 (0.78 g, 1.98 mmol) the same protocol was used as described in Example 1 step 1 to afford Example 51 as a beige solid.

MS (ESI): 483 [M+H]⁺, ¹H-NMR (DMSO-d₆): δ (ppm) 12.33 (br s, 1H), 9.91 (s, 1H), 8.80 (s, 1H), 7.93 (d, 2H), 7.59 (m, 1H), 7.55 (d, 2H), 7.38 (m, 2H), 6.76 (m, 1H), 6.29 (s, 1H), 3.35 (m, 2H), 2.82 (m, 2H), 2.64 (m, 2H), 2.14 (s, 3H), 1.32 (s, 9H).

Example 52

4-tert-Butyl-N-{2-methyl-3-[6-(3,6-dihydro-1-oxido-2H-thiopyran-4-yl)-7H-pyrrolo[2,3-d]pyrimidin-4-yl]-phenyl}-benzamide

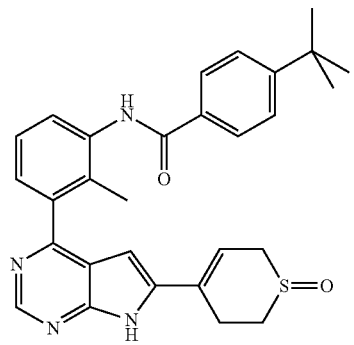 [SMILES: Cc1c(NC(=O)c2ccc(C(C)(C)C)cc2)cccc1-c1ncnc2[nH]c(C3=CCS(=O)CC3)cc12]

Compound of Example 51 (240 mg, 0.50 mmol) was dissolved in acetic acid (5 ml) and hydrogen peroxide (0.051 ml, 0.50 mmol) was added. The mixture was stirred at room temperature for 4 hours. The mixture was treated with sodium hydrogen sulfite solution 10% (10 ml) for 10 minutes, diluted with water, basified with 2N sodium hydroxide solution and extracted with EtOAc. The organic layer was washed with brine (2×), dried over sodium sulfate, filtered and evaporated. The residue was purified by flash chromatography on silica (EtOAc to EtOAc/MeOH/NH$_4$OH 9:1:0.1 to EtOAc/MeOH/NH$_4$OH4 8:2:0.2) to afford the compound Example 52 as a beige solid.

MS (ESI): 499 [M+H]$^+$, $^1$H-NMR (DMSO-d$_6$): δ (ppm) 12.45 (br s, 1H), 9.95 (s, 1H), 8.84 (s, 1H), 7.96 (d, 2H), 7.57 (d, 2H), 7.52 (m, 1H), 7.41 (m, 2H), 6.49 (br s, 1H), 6.42 (s, 1H), 3.72 (m, 1H), 3.49 (m, 1H), 3.15 (m, 1H), 2.96 (m, 1H), 2.89 (m, 1H), 2.77 (m, 1H), 2.17 (s, 3H), 1.34 (s, 9H).

Example 53

4-tert-Butyl-N-{3-[6-(3,6-dihydro-1,1-dioxido-2H-thiopyran-4-yl)-7H-pyrrolo[2,3-d]pyrimidin-4-yl]-2-methyl-phenyl}-benzamide

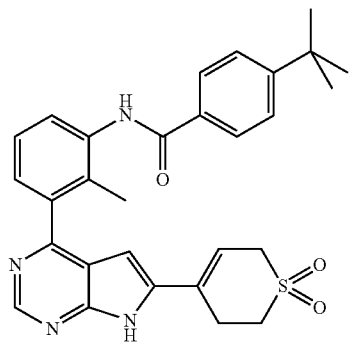 [SMILES: Cc1c(NC(=O)c2ccc(C(C)(C)C)cc2)cccc1-c1ncnc2[nH]c(C3=CCS(=O)(=O)CC3)cc12]

Compound of Example 51 (250 mg, 0.51 mmol) was dissolved in DCM (5 ml), then trifluoro acetic acid (5 ml) and hydrogen peroxide (0.079 ml, 0.78 mmol) were added. The mixture was stirred at room temperature for 2 hours. The mixture was treated with sodium hydrogen sulfite solution 10% (10 ml) for 10 minutes, diluted with water, basified with 2N sodium hydroxide solution and extracted with EtOAc. The organic layer was washed with brine (2×), dried over sodium sulfate, filtered and evaporated. The residue was purified by flash chromatography on silica (EtOAc to EtOAc/MeOH/NH$_4$OH 98:2:0.2) to afford the compound Example 53 as a beige solid.

MS (ESI): 515 [M+H]$^+$, $^1$H-NMR (DMSO-d$_6$): δ (ppm) 12.47 (br s, 1H), 9.93 (s, 1H), 8.84 (s, 1H), 7.94 (d, 2H), 7.60 (m, 1H), 7.56 (d, 2H), 7.49 (m, 1H), 7.40 (m, 1H), 6.48 (m, 1H), 6.43 (s, 1H), 4.00 (m, 2H), 3.36 (m, 2H), 3.07 (m, 2H), 2.16 (s, 3H), 1.33 (s, 9H).

Example 54

4-tert-Butyl-N-{3-[6-(1,4-dioxa-spiro[4.5]dec-7-en-8-yl)-7H-pyrrolo[2,3-d]pyrimidin-4-yl]-2-hydroxymethyl-phenyl}-benzamide

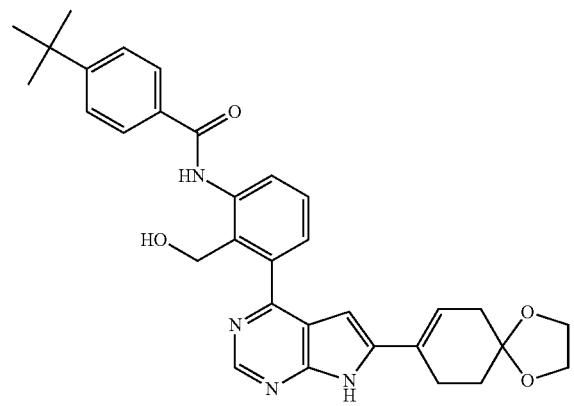 [SMILES: CC(C)(C)c1ccc(C(=O)Nc2cccc(-c3ncnc4[nH]c(C5=CCC6(CC5)OCCO6)cc34)c2CO)cc1]

Example 54 was prepared analogue to Intermediate 29 by replacing Intermediate 1 with Intermediate 17, followed by removal of the TBDPS protecting group with TBAF in THF.

MS (ESI): 539 [M+H]$^+$, $^1$H-NMR (DMSO-d$_6$): δ (ppm) 12.34 (br s, 1H), 10.51 (s, 1H), 8.80 (s, 1H), 8.21 (d, 1H), 7.90 (d, 2H), 7.59 (d, 2H), 7.49 (t, 1H), 7.33 (d, 1H), 6.48 (m, 1H), 6.39 (s, 1H), 5.90 (m, 1H), 4.67 (m, 2H), 3.91 (m, 4H), 2.57 (m, 2H), 2.42 (m, 2H), 1.79 (m, 2H), 1.32 (s, 9H).

Example 55

4-tert-Butyl-N-{3-[6 (4 hydroxy-cyclohex-1-enyl)-7H-pyrrolo[2,3-d]pyrimidin-4-yl]-2-hydroxymethyl-phenyl}-benzamide

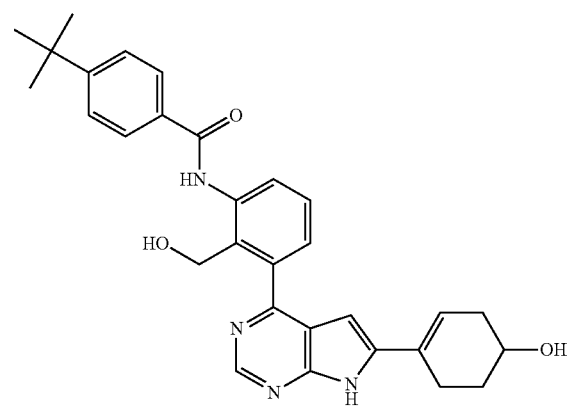 [SMILES: CC(C)(C)c1ccc(C(=O)Nc2cccc(-c3ncnc4[nH]c(C5=CCC(O)CC5)cc34)c2CO)cc1]

85

(1) 4-tert-Butyl-N-{2-hydroxymethyl-3-[6-(4-oxo-cyclohex-1-enyl)-7H-pyrrolo[2,3-d]pyrimidin-4-yl]-phenyl}-benzamide, Intermediate 49

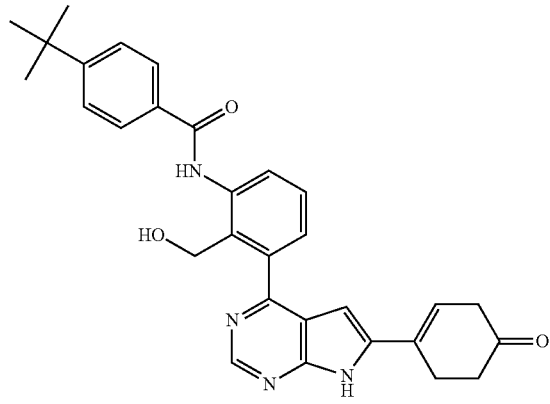 [SMILES: CC(C)(C)c1ccc(C(=O)Nc2cccc(-c3ncnc4[nH]c(C5=CCC(=O)CC5)cc34)c2CO)cc1]

Intermediate 49 was prepared analogue to Intermediate 19 by replacing Example 27 with Example 54.

MS (ESI): 495 [M+H]$^+$

(2) 4-tert-Butyl-N-{3-[6-(4-hydroxy-cyclohex-1-enyl)-7H-pyrrolo[2,3-d]pyrimidin-4-yl]-2-hydroxymethyl-phenyl}-benzamide

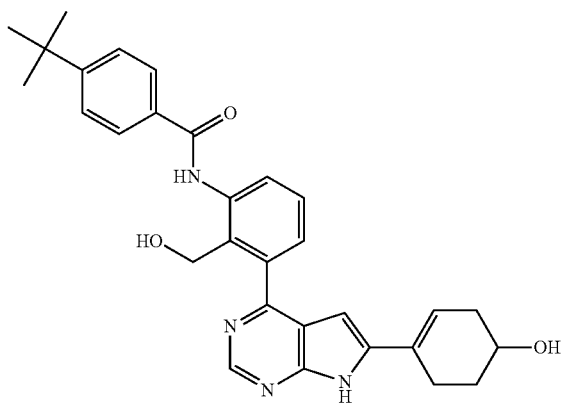 [SMILES: CC(C)(C)c1ccc(C(=O)Nc2cccc(-c3ncnc4[nH]c(C5=CCC(O)CC5)cc34)c2CO)cc1]

To a solution of Intermediate 49 (80 mg, 0.162 mmol) in MeOH/DCM (1:1) were added cerium(III) chloride heptahydrate (66.3 mg, 0.178 mmol) and NaBH$_4$ (6.1 mg, 0.162 mmol). The resulting mixture was stirred at r.t. for 2 hrs. Water was added, and the mixture was extracted three times with DCM/isopropanol (3:1). The combined organic layers were dried, filtered, and evaporated to dryness. The resulting residue was purified using flash chromatography (silica gel, EtOAc/MeOH/N H$_3$ gradient) to yield Example 55.

MS (ESI): 497 [M+H]$^+$, $^1$H-NMR (DMSO-d$_6$): δ (ppm) 12.29 (br s, 1H), 10.51 (s, 1H), 8.79 (s, 1H), 8.19 (d, 1H), 7.90 (d, 2H), 7.59 (d, 2H), 7.49 (t, 1H), 7.34 (d, 1H), 6.49 (m, 1H), 6.35 (s, 1H), 5.89 (m, 1H), 4.72 (m, 1H), 4.67 (m, 2H), 3.80 (m, 1H), 2.65-2.35 (m, 3H), 2.11 (m, 1H), 1.84 (m, 1H), 1.59 (m, 1H), 1.33 (s, 9H).

86

Example 56

4-tert-Butyl-N-{3-[6 (4 dimethylamino-cyclohex-1-enyl)-7H-pyrrolo[2,3-d]pyrimidin-4-yl]-2-hydroxymethyl-phenyl}-benzamide

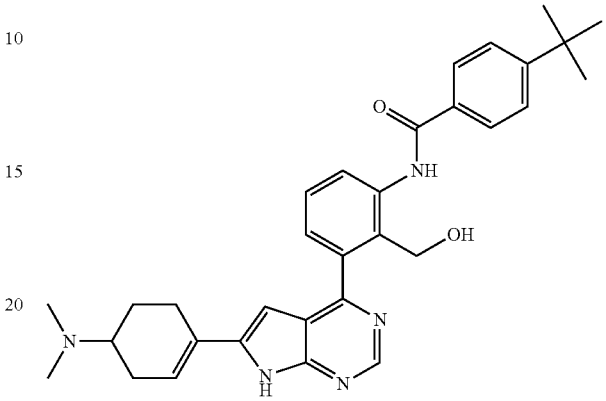

To a solution of Intermediate 49 (100 mg, 0.202 mmol) in DCM/MeOH/AcOH (4 ml, 100:93:7) was added dimethylamine (91 mg, 2.02 mmol). The mixture was stirred for 15 min at r.t. before adding sodium cyanoborohydride (12.7 mg, 0.202 mmol). The mixture was stirred at r.t. overnight and then quenched with 2N HCl (3 ml). After additional stirring for 30 min water and 2N NaOH were added. The mixture was extracted with EtOAc, and the organic layer was dried, filtered, and evaporated to dryness. The resulting residue was purified using flash chromatography (silica gel, EtOAc/MeOH/NH$_4$OH gradient) to yield Example 56.

MS (ESI): 524 [M+H]$^+$, $^1$H-NMR (DMSO-d$_6$): δ (ppm) 12.31 (br s, 1H), 10.51 (s, 1H), 8.79 (s, 1H), 8.19 (m, 1H), 7.90 (d, 2H), 7.59 (d, 2H), 7.49 (t, 1H), 7.34 (d, 1H), 6.57 (m, 1H), 6.35 (s, 1H), 5.89 (m, 1H), 4.66 (m, 2H), 2.60-2.15 (m, 5H), 2.27 (m, 3H), 1.99 (m, 1H), 1.48 (m, 1H), 1.31 (s, 9H).

Example 57

4-(4-{3-[(3-tert-Butoxy-azetidine-1-carbonyl)-amino]-5-fluoro-2-methyl-phenyl}-7H-pyrrolo[2,3-d]pyrimidin-6-yl)-3,6-dihydro-2H-pyridine-1-carboxylic acid dimethylamide

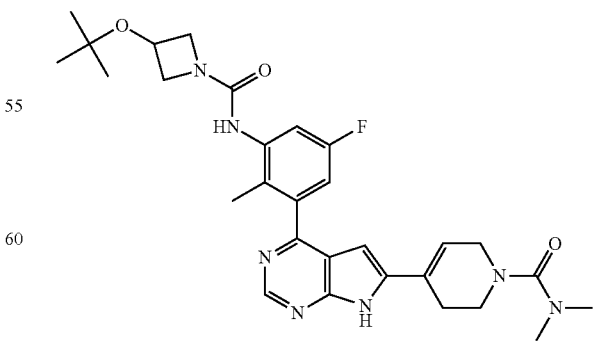

A mixture of Intermediate 6 (50 mg, 0.127 mmol), 4-nitrophenylchloroformate (25.6 mg, 0.127 mmol), pyridine (12 mg, 0.152 mmol), and DMAP (1.5 mg, 0.013 mmol) in THF (2 ml) was stirred ar r.t. for 5 hrs. Then additional 4-nitrophenylchloroformate (25.6 mg, 0.127 mmol) was added and stirring at r.t. was continued for 72 hrs. Then pyridine (100 mg, 1.27 mmol) and 3-tert-butoxy-azetidine hydrochloride (US2009/0105209) (105 mg, 0.634 mmol) were added and the mixture was stirred for 1 hr. The mixture was diluted into EtOAc and aqueous $NH_4OH$ solution (2 M). The organic layer was washed with brine, dried with $Na_2SO_4$, filtered, and evaporated to dryness. The crude product was purified by flash chromatography (silica gel, EtOAc/MeOH gradient) to afford Example 57 as beige solid.

MS (ESI): 550 $[M+H]^+$, $^1$H-NMR (DMSO-$d_6$): δ (ppm) 12.45 (br s, 1H), 8.80 (s, 1H), 7.97 (br s, 1H), 7.44 (m, 1H), 7.00 (m, 1H), 6.57 (br s, 1H), 6.27 (s, 1H), 4.52 (m, 1H), 4.17 (m, 2H), 3.87 (m, 2H), 3.75 (m, 2H), 3.30 (m, 2H), 2.74 (s, 6H), 2.49 (m, 2H), 2.03 (s, 3H), 1.13 (s, 9H).

Example 58

4-(4-{5-Fluoro-3-[(3-isopropoxy-azetidine-1-carbonyl)-amino]-2-methyl-phenyl}-7H-pyrrolo[2,3-d]pyrimidin-6-yl)-3,6-dihydro-2H-pyridine-1-carboxylic acid dimethylamide

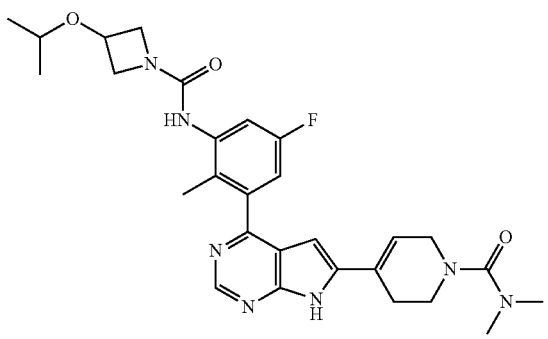 [SMILES: Cc1c(NC(=O)N2CC(OC(C)C)C2)cc(F)cc1-c1ncnc2[nH]c(C3=CCN(C(=O)N(C)C)CC3)cc12]

Example 58 was prepared analogue to Example 57 by replacing 3-tert-butoxy-azetidine hydrochloride with 3-isopropoxy-azetidine hydrochloride.

MS (ESI): 536 $[M+H]^+$, $^1$H-NMR (CDCl$_3$): δ (ppm) 12.24 (br s, 1H), 8.86 (s, 1H), 7.78 (m, 1H), 6.93 (m, 1H), 6.49 (m, 1H), 6.33 (s, 1H), 6.28 (m, 1H), 4.39 (m, 1H), 4.24 (m, 2H), 4.03 (m, 2H), 3.97 (m, 2H), 3.62 (m, 1H), 3.47 (m, 2H), 2.86 (s, 6H), 2.62 (m, 2H), 2.11 (s, 3H), 1.16 (d, 6H).

Example 59

5-Fluoro-1,3-dihydro-isoindole-2-carboxylic acid {3-[6-(1-dimethylcarbamoyl-1,2,3,6-tetrahydro-pyridin-4-yl)-7H-pyrrolo[2,3-d]pyrimidin-4-yl]-5-fluoro-2-methyl-phenyl}-amide

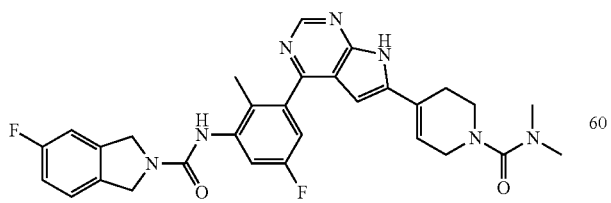

Example 59 was prepared analogue to Example 57 by replacing 3-tert-butoxy-azetidine hydrochloride with 5-fluoro-2,3-dihydro-1H-isoindole.

MS (ESI): 558 $[M+H]^+$, $^1$H-NMR (DMSO-$d_6$): δ (ppm) 12.40 (br s, 1H), 8.81 (s, 1H), 7.96 (s, 1H), 7.56 (m, 1H), 7.41 (m, 1H), 7.26 (m, 1H), 7.14 (m, 1H), 7.04 (m, 1H), 6.58 (s, 1H), 5.30 (s, 1H), 4.78 (m, 4H), 3.89 (m, 2H), 3.34 (m, 2H), 2.76 (s, 6H), 2.52 (m, 2H), 2.11 (s, 3H).

Example 60

4-[4-(5-Fluoro-2-methyl-3-{[3-(2,2,2-trifluoro-1-trifluoromethyl-ethoxy)-azetidine-1-carbonyl]-amino}-phenyl)-7H-pyrrolo[2,3-d]pyrimidin-6-yl]-3,6-dihydro-2H-pyridine-1-carboxylic acid dimethylamide

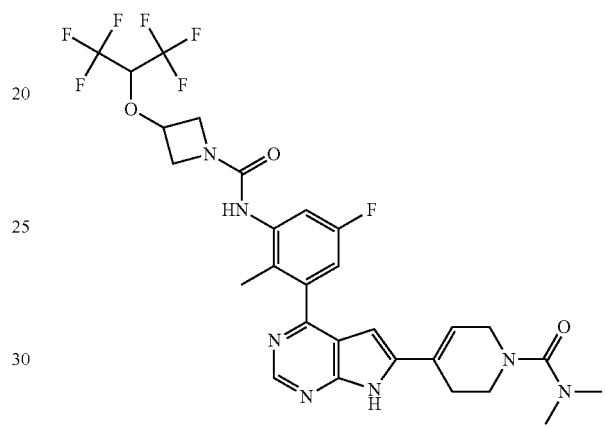

Example 60 was prepared analogue to Example 57 by replacing 3-tert-butoxy-azetidine hydrochloride with 3-(2,2,2-trifluoro-1-trifluoromethyl-ethoxy)-azetidine hydrochloride (WO2009/077334).

MS (ESI): 644 $[M+H]^+$, $^1$H-NMR (DMSO-$d_6$): δ (ppm) 12.35 (br s, 1H), 8.76 (s, 1H), 8.10 (s, 1H), 7.39 (m, 1H), 7.00 (m, 1H), 6.54 (m, 1H), 6.23 (s, 1H), 5.63 (m, 1H), 4.75 (m, 1H), 4.25 (m, 2H), 3.87 (m, 2H), 3.85 (m, 2H), 3.82 (m, 2H), 2.72 (s, 6H), 2.46 (m, 2H), 2.01 (s, 3H).

Example 61

3-tert-Butoxy-azetidine-1-carboxylic acid {3-[6-(3,6-dihydro-2H-pyran-4-yl)-7H-pyrrolo[2,3-d]pyrimidin-4-yl]-5-fluoro-2-methyl-phenyl}-amide

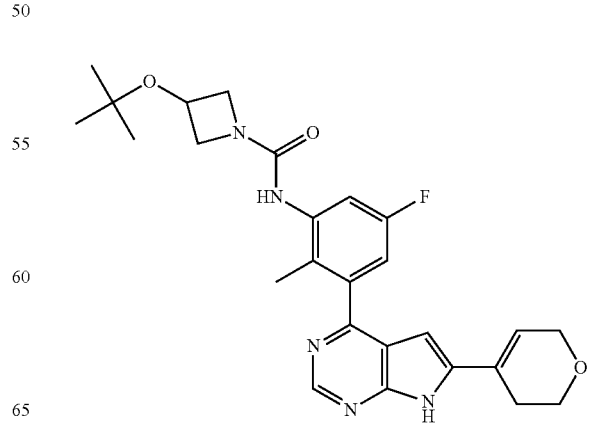

Example 61 was prepared analogue to Example 57 by replacing Intermediate 6 with Intermediate 12.

MS (ESI): 480 [M+H]$^+$, $^1$H-NMR (DMSO-d$_6$): δ (ppm) 12.40 (br s, 1H), 8.80 (s, 1H), 7.95 (s, 1H), 7.43 (m, 1H), 7.00 (m, 1H), 6.62 (br s, 1H), 6.26 (s, 1H), 4.52 (m, 1H), 4.27 (m, 2H), 4.18 (m, 2H), 3.79 (m, 2H), 3.75 (m, 2H), 2.44 (m, 2H), 2.04 (s, 3H), 1.13 (s, 9H).

Example 62

4-(4-{3-[(3-tert-Butoxy-azetidine-1-carbonyl)-amino]-4-fluoro-phenyl}-7H-pyrrolo[2,3-d]pyrimidin-6-yl)-3,6-dihydro-2H-pyridine-1-carboxylic acid dimethylamide

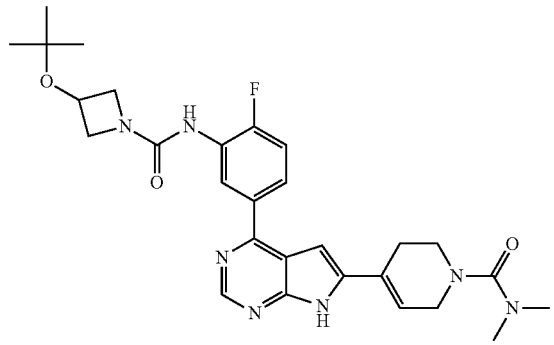 [SMILES: CN(C)C(=O)N1CC=C(c2cc3c(-c4ccc(F)c(NC(=O)N5CC(OC(C)(C)C)C5)c4)ncnc3[nH]2)CC1]

Example 62 was prepared analogue to Example 57 by replacing Intermediate 6 with Intermediate 10.

MS (ESI): 536 [M+H]$^+$, $^1$H-NMR (DMSO-d$_6$): δ (ppm) 12.36 (br s, 1H), 8.77 (s, 1H), 8.49 (m, 1H), 8.33 (s, 1H), 7.90 (m, 1H), 7.39 (m, 1H), 6.88 (s, 1H), 6.59 (s, 1H), 4.53 (m, 1H), 4.21 (m, 2H), 3.91 (m, 2H), 3.78 (m, 2H), 3.37 (m, 2H), 2.77 (s, 6H), 2.60 (m, 2H), 1.14 (s, 9H).

Example 63

4-(4-{3-[(3-tert-Butoxy-azetidine-1-carbonyl)-amino]-4-fluoro-2-methyl-phenyl}-7H-pyrrolo[2,3-d]pyrimidin-6-yl)-3,6-dihydro-2H-pyridine-1-carboxylic acid dimethylamide

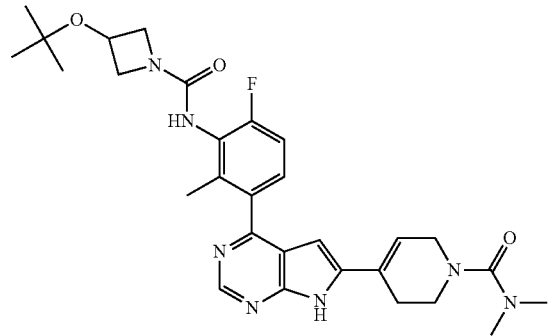 [SMILES: Cc1c(-c2ncnc3[nH]c(C4=CCN(C(=O)N(C)C)CC4)cc23)ccc(F)c1NC(=O)N1CC(OC(C)(C)C)C1]

(1) 4-[4-(3-Amino-4-fluoro-2-methyl-phenyl)-7H-pyrrolo[2,3-d]pyrimidin-6-yl]-3,6-dihydro-2H-pyridine-1-carboxylic acid dimethylamide, Intermediate 50

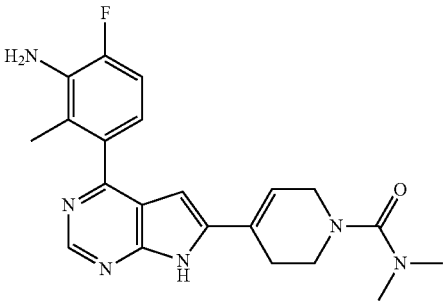

Intermediate 10 was prepared analogue to Intermediate 6 by replacing Intermediate 5 with 5-fluoro-2-methyl-3-(4,4,5,5-tetramethyl-1,3,2-dioxaborolan-2-yl)aniline.

MS (ESI): 395 [M+H]$^+$, $^1$H-NMR (DMSO-d$_6$): δ (ppm) 12.28 (br s, 1H), 8.75 (s, 1H), 7.03 (m, 1H), 6.68 (m, 1H), 6.54 (s, 1H), 6.25 (s, 1H), 5.00 (br s, 2H), 3.88 (s, 2H), 3.32 (m, 2H), 2.75 (s, 6H), 2.50 (m, 2H), 2.03 (s, 3H).

(2) 4-(4-{3-[(3-tert-Butoxy-azetidine-1-carbonyl)-amino]-4-fluoro-2-methyl-phenyl}-7H-pyrrolo[2,3-d]pyrimidin-6-yl)-3,6-dihydro-2H-pyridine-1-carboxylic acid dimethylamide

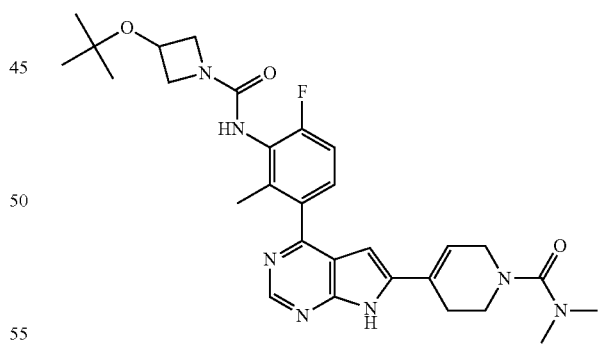

Example 62 was prepared analogue to Example 57 by replacing Intermediate 6 with Intermediate 50.

MS (ESI): 550 [M+H]$^+$, $^1$H-NMR (DMSO-d$_6$): δ (ppm) 12.36 (br s, 1H), 8.79 (s, 1H), 8.04 (m, 1H), 7.37 (m, 1H), 7.21 (m, 1H), 6.57 (m, 1H), 6.25 (s, 1H), 4.54 (m, 1H), 4.14 (m, 2H), 3.89 (m, 2H), 3.70 (m, 2H), 3.32 (m, 2H), 2.75 (s, 6H), 2.50 (m, 2H), 2.13 (s, 3H), 1.14 (s, 9H).

Example 64

4-tert-Butyl-N-{3-[6-(3,6-dihydro-2H-pyran-4-yl)-7H-pyrrolo[2,3-d]pyrimidin-4-yl]-2-methyl-phenyl}-benzamide

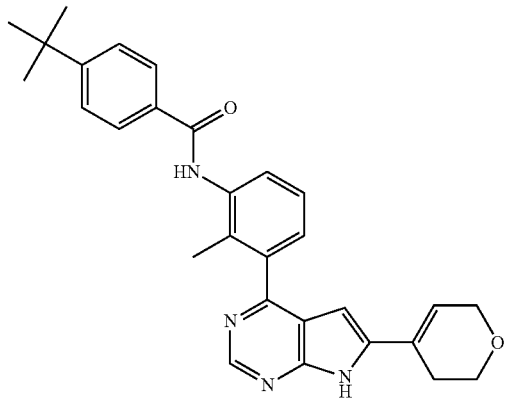 [SMILES: Cc1c(NC(=O)c2ccc(C(C)(C)C)cc2)cccc1-c1ncnc2[nH]c(C3=CCOCC3)cc12]

(1) 4-tert-Butyl-N-[2-methyl-3-(7H-pyrrolo[2,3-d]pyrimidin-4-yl)-phenyl]-benzamide, Intermediate 51

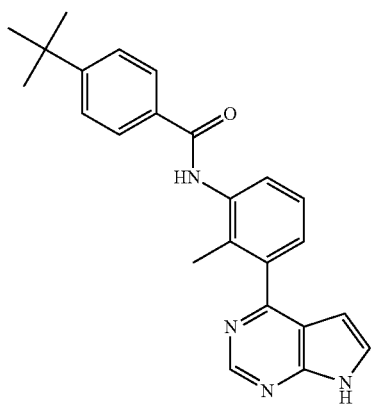 [SMILES: Cc1c(NC(=O)c2ccc(C(C)(C)C)cc2)cccc1-c1ncnc2[nH]ccc12]

Intermediate 51 was prepared analogue to Intermediate 6 by replacing Intermediate 3 with 6-chloro-7-deazapurine and Intermediate 5 with Intermediate 48.

MS (ESI): 385 [M+H]$^+$, $^1$H-NMR (DMSO-d$_6$): δ (ppm) 12.22 (br s, 1H), 9.94 (s, 1H), 8.82 (s, 1H), 7.94 (d, 2H), 7.60 (m, 1H), 7.58 (d, 2H), 7.37 (m, 1H), 6.30 (m, 1H), 2.12 (s, 3H), 1.31 (s, 9H).

(2) N-[3-(7-Benzenesulfonyl-7H-pyrrolo[2,3-d]pyrimidin-4-yl)-2-methyl-phenyl]-4-tert-butyl-benzamide, Intermediate 52

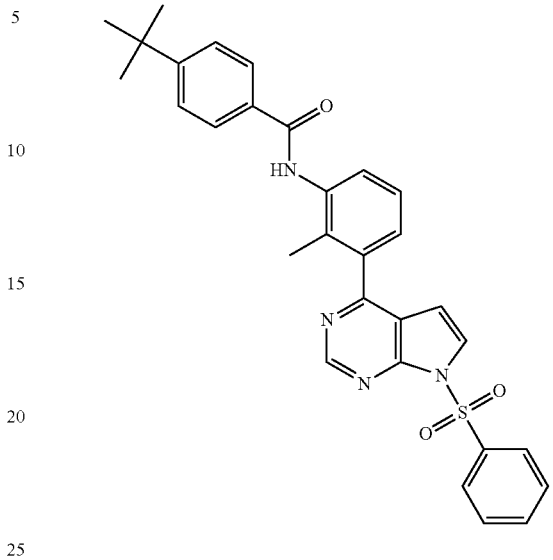

To a solution of Intermediate 51 (7.51 g, 19.54 mmol) in THF (500 ml) at 0° C. was added NaH (1.172 g, 29.3 mmol) portionwise. The mixture was stirred at 0° C. for 3 hrs, then benzenesulfonyl chloride (3.70 ml, 25.4 mmol) was added and stirring was continued at r.t. overnight. The reaction mixture was quenched with sat. aqueous NH$_4$Cl solution, and extracted with EtOAc. The organic layer was dried, filtered, and evaporated to dryness. Purification by flash chromatography (silica gel, cyclohexane/EtOAc gradient) yielded Intermediate 52.

MS (ESI): 525 [M+H]$^+$, $^1$H-NMR (DMSO-d$_6$): δ (ppm) 9.97 (s, 1H), 9.10 (s, 1H), 8.21 (d, 2H), 8.05 (d, 1H), 7.92 (d, 2H), 7.78 (t, 1H), 7.69 (t, 2H), 7.60 (m, 1H), 7.53 (d, 2H), 7.51 (d, 1H), 7.37 (t, 1H), 7.32 (d, 1H), 6.62 (d, 1H), 2.12 (s, 3H), 1.31 (s, 9H).

(3) N-[3-(7-Benzenesulfonyl-6-bromo-7H-pyrrolo[2,3-d]pyrimidin-4-yl)-2-methyl-phenyl]-4-tert-butyl-benzamide, Intermediate 53

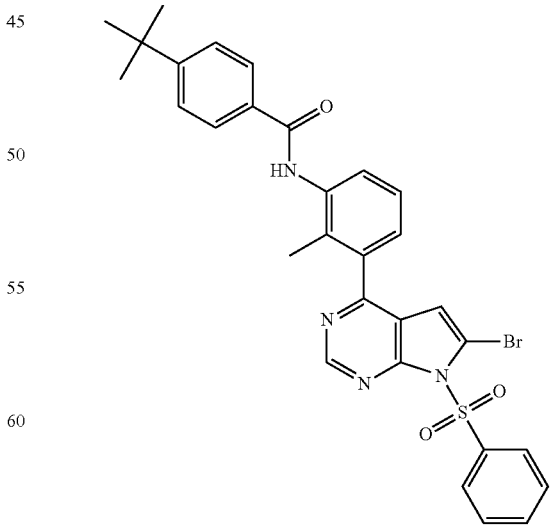

To a solution of Intermediate 52 (4.26 g, 8.12 mmol) in THF (150 ml) at −78° C. was added LDA (1.5 M in THF, 16.24 ml, 24.36 mmol) slowly. The resulting mixture was stirred for 1.5 hrs at −78° C. before adding a solution of 1,2-dibromo-tetrachloroethane (3.97 g, 12.18 mmol) in THF (1 ml). Stirring was continued at −78° C. for 2 hrs, then the reaction mixture was quenched by addition of sat. aqueous NH₄Cl solution and warmed up to r.t. The mixture was extracted with EtOAc and the organic layer was dried, filtered, and evaporated to dryness. Purification by flash chromatography (silica gel, cyclohexane/EtOAc gradient) yielded Intermediate 53.

MS (ESI): 603 [M+H]⁺

(4) N-[3-(6-Bromo-7H-pyrrolo[2,3-d]pyrimidin-4-yl)-2-methyl-phenyl]-4-tert-butyl-benzamide, Intermediate 54

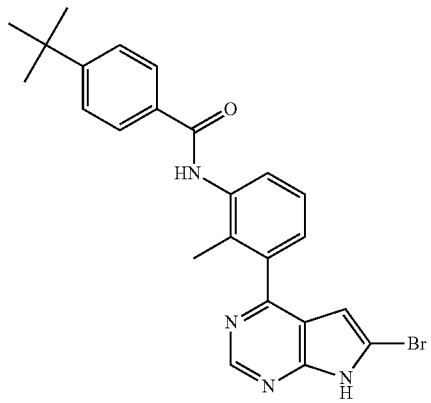 [SMILES: Cc1c(NC(=O)c2ccc(C(C)(C)C)cc2)cccc1-c1ncnc2[nH]c(Br)cc12]

To a solution of Intermediate 53 (3.82 g, 6.33 mmol) in THF (64 ml) was added a solution of potassium tert-butylate in THF (1 M, 9.49 ml, 9.49 mmol) at 0° C. The mixture was stirred at 0° C. for 1 hr, then an additional solution of potassium tert-butylate in THF (1 M, 2.00 ml, 2.00 mmol) was added and stirring was continued for an additional 1 hr. The reaction was quenched by addition of sat. aqueous NaHCO₃ solution, and the mixture was extracted with EtOAc. The organic layer was dried, filtered, and evaporated to dryness. Purification by flash chromatography (silica gel, cyclohexane/EtOAc gradient) yielded Intermediate 54.

MS (ESI): 463 [M+H]⁺, ¹H-NMR (DMSO-d₆): δ (ppm) 13.10 (br s, 1H), 9.97 (s, 1H), 8.82 (s, 1H), 7.93 (d, 2H), 7.54 (d, 1H), 7.48 (d, 1H), 7.40-7.32 (m, 2H), 6.41 (s, 1H), 2.12 (s, 3H), 1.31 (s, 9H).

(5) 4-tert-Butyl-N-{3-[6-(3,6-dihydro-2H-pyran-4-yl)-7H-pyrrolo[2,3-d]pyrimidin-4-yl]-2-methyl-phenyl}-benzamide

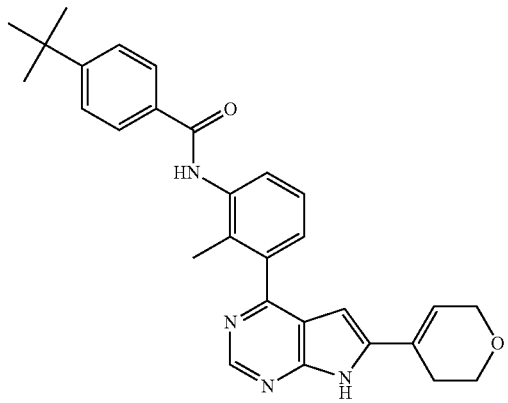 [SMILES: Cc1c(NC(=O)c2ccc(C(C)(C)C)cc2)cccc1-c1ncnc2[nH]c(C3=CCOCC3)cc12]

Example 64 was prepared analogue to Intermediate 11 by replacing 4-chloro-6-iodo-7H-pyrrolo[2,3-d]pyrimidine with Intermediate 54.

MS (ESI): 467 [M+H]⁺, ¹H-NMR (DMSO-d₆): δ (ppm) 12.33 (br s, 1H), 9.93 (s, 1H), 8.82 (s, 1H), 7.94 (d, 2H), 7.54 (d, 2H), 7.48 (m, 1H), 7.37 (m, 2H), 6.63 (br s, 1H), 6.25 (s, 1H), 4.36 (m, 2H), 3.81 (m, 2H), 2.46 (m, 2H), 2.16 (s, 3H), 1.33 (s, 9H).

Example 65

4-tert-Butyl-N-{3-[6-(1,4-dioxa-spiro[4.5]dec-7-en-8-yl)-7H-pyrrolo[2,3-d]pyrimidin-4-yl]-2-methyl-phenyl}-benzamide

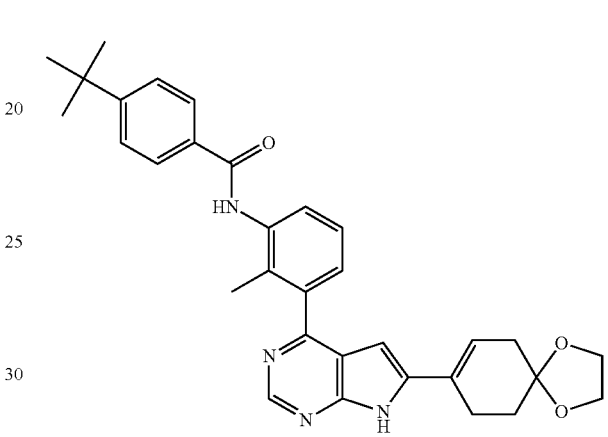

Example 65 was prepared analogue to Intermediate 17 by replacing 4-chloro-6-iodo-7H-pyrrolo[2,3-d]pyrimidine with Intermediate 54.

MS (ESI): 523 [M+H]⁺, ¹H-NMR (DMSO-d₆): δ (ppm) 12.28 (br s, 1H), 9.91 (s, 1H), 8.78 (s, 1H), 7.94 (d, 2H), 7.54 (d, 2H), 7.49 (m, 1H), 7.37 (m, 2H), 6.46 (br s, 1H), 6.23 (s, 1H), 3.90 (s, 4H), 2.55 (m, 2H), 2.41 (m, 2H), 2.14 (s, 3H), 1.79 (m, 2H), 1.31 (s, 9H).

Example 66

4-tert-Butyl-N-{3-[6 (4 hydroxy-cyclohex-1-enyl)-7H-pyrrolo[2,3-d]pyrimidin-4-yl]-2-methyl-phenyl}-benzamide

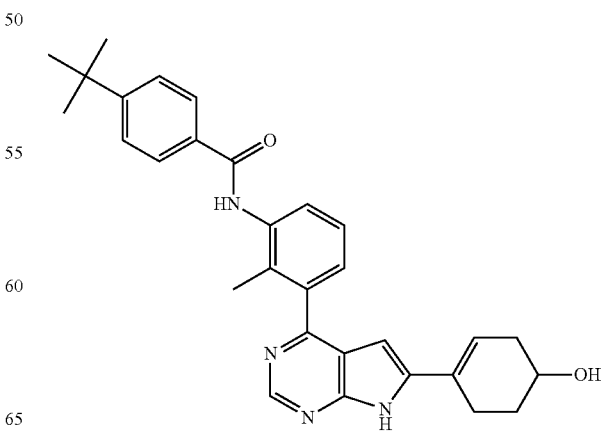

(1) 4-tert-Butyl-N-{2-methyl-3-[6-(4-oxo-cyclohex-1-enyl)-7H-pyrrolo[2,3-d]pyrimidin-4-yl]-phenyl}-benzamide, Intermediate 55

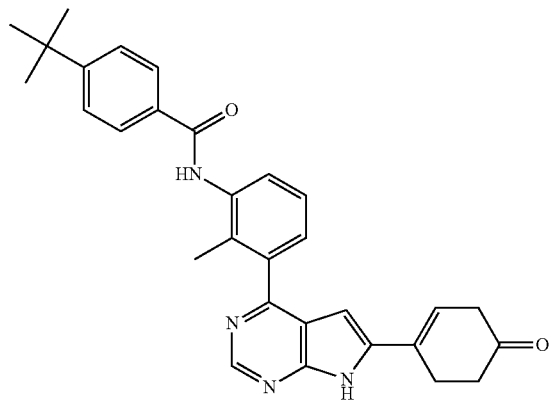 [SMILES: Cc1c(NC(=O)c2ccc(C(C)(C)C)cc2)cccc1-c1ncnc2[nH]c(C3=CCC(=O)CC3)cc12]

Intermediate 55 was prepared analogue to Intermediate 19 by replacing Example 27 with Example 65.

MS (ESI): 479 [M+H]$^+$, $^1$H-NMR (DMSO-d$_6$): δ (ppm) 12.35 (br s, 1H), 9.92 (s, 1H), 8.78 (s, 1H), 7.94 (d, 2H), 7.53 (d, 2H), 7.49 (m, 1H), 7.36 (m, 2H), 6.64 (br s, 1H), 6.35 (s, 1H), 3.15 (m, 2H), 2.83 (m, 2H), 2.52 (m, 2H), 2.13 (s, 3H), 1.31 (s, 9H).

(2) 4-tert-Butyl-N-{3-[6 (4 hydroxy-cyclohex-1-enyl)-7H-pyrrolo[2,3-d]pyrimidin-4-yl]-2-methyl-phenyl}-benzamide

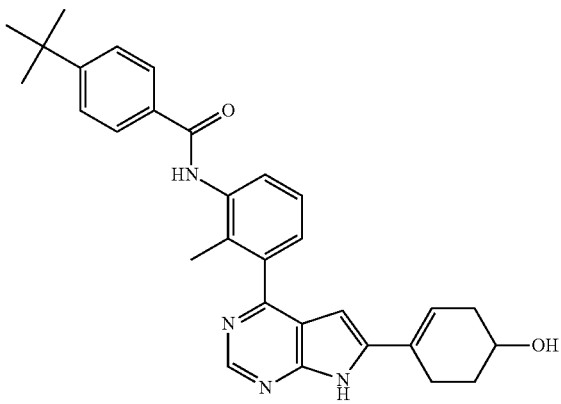 [SMILES: Cc1c(NC(=O)c2ccc(C(C)(C)C)cc2)cccc1-c1ncnc2[nH]c(C3=CCC(O)CC3)cc12]

Example 66 was prepared analogue to Example 28 step 2 by replacing Intermediate 19 in with Intermediate 55.

MS (ESI): 481 [M+H]$^+$, $^1$H-NMR (DMSO-d$_6$): δ (ppm) 12.21 (br s, 1H), 9.93 (s, 1H), 8.77 (s, 1H), 7.94 (d, 2H), 7.53 (d, 2H), 7.43 (m, 1H), 7.37 (m, 2H), 6.47 (br s, 1H), 6.18 (s, 1H), 4.75 (s, 1H), 3.76 (m, 1H), 2.44 (m, 2H), 2.35 (m, 2H), 2.14 (s, 3H), 1.83 (m, 2H), 1.31 (s, 9H).

Example 67

4-tert-Butyl-N-{3-[6 (4 dimethylamino-cyclohex-1-enyl)-7H-pyrrolo[2,3-d]pyrimidin-4-yl]-2-methyl-phenyl}-benzamide

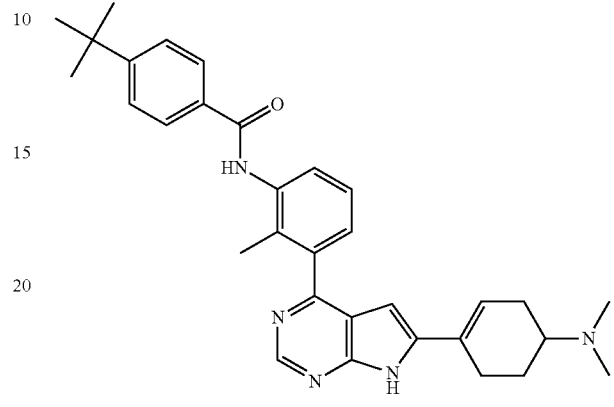

Example 67 was prepared analogue to Example 56 by replacing Intermediate 49 with Intermediate 55.

MS (ESI): 508 [M+H]$^+$, $^1$H-NMR (DMSO-d$_6$): δ (ppm) 12.23 (br s, 1H), 9.94 (s, 1H), 8.78 (s, 1H), 7.94 (d, 2H), 7.53 (d, 2H), 7.48 (m, 1H), 7.35 (m, 2H), 6.53 (br s, 1H), 6.21 (s, 1H), 2.61 (m, 2H), 2.51 (m, 1H), 2.42 (m, 1H), 2.40 br s, 6H), 2.24 (m, 1H), 2.16 (s, 3H), 2.05 (m, 1H), 1.56 (m, 1H), 1.28 (s, 9H).

Biological Part

Inhibition of Btk Enzymatic Activity

The inhibitory activity of the present compounds against Btk was assessed in a biochemical enzyme assay. Assay plates in 384 well format were prepared with 8-point serial dilutions for the test compounds on a Thermo CatX workstation equipped with a Innovadyne Nanodrop Express. The assay plates were prepared by addition of 50 nl per well of compound solution in 90% DMSO. The kinase reactions were started by stepwise addition of 4.5 μl per well of peptide/ATP-solution (4 μM FITC-Ahx-TSELKKVVALYDYMPM-NAND-NH2, 164 μM ATP) in kinase buffer (50 mM HEPES, pH 7.5, 1 mM DTT, 0.02% Tween20, 0.02% BSA, 0.6% DMSO, 10 mM beta-glycerophosphate, and 10 μM sodium orthovanadate, 18 mM MgCl2, 1 mM MnCl2) and 4.5 μl per well of enzyme solution (6.4 nM full-length human recombinant BTK) in kinase buffer. Kinase reactions were incubated at 30° C. for 60 minutes and subsequently terminated by addition of 16 μl per well of stop solution (100 mM HEPES pH 7.5, 5% DMSO, 0.1% Caliper coating reagent, 10 mM EDTA, and 0.015% Brij35). Kinase reactions were analyzed on a Caliper LC3000 workstation by separating phosphorylated and unphosphorylated peptides and kinase activities were calculated from the amounts of newly formed phosphopeptide. Inhibition data were calculated by comparison to control reactions without enzyme (100% inhibition) and without inhibitors (0% inhibition). The concentration of inhibitor required for 50% inhibition (IC50) was calculated from the inhibition in response to inhibitor concentrations.

| Example | Inhibition of Btk enzymatic activity IC$_{50}$ [uM] |
|---|---|
| Example 1 | 0.001 |
| Example 2 | 0.004 |
| Example 3 | 0.005 |
| Example 4 | 0.002 |
| Example 5 | 0.003 |
| Example 6 | 0.002 |
| Example 7 | 0.003 |
| Example 8 | 0.003 |
| Example 9 | 0.005 |
| Example 10 | 0.015 |
| Example 11 | 0.005 |
| Example 12 | 0.004 |
| Example 13 | 0.004 |
| Example 14 | 0.016 |
| Example 15 | 0.017 |
| Example 16 | 0.002 |
| Example 17 | 0.001 |
| Example 18 | 0.006 |
| Example 19 | 0.023 |
| Example 20 | 0.006 |
| Example 21 | 0.006 |
| Example 22 | 0.008 |
| Example 23 | 0.012 |
| Example 24 | 0.023 |
| Example 25 | 0.002 |
| Example 26 | 0.035 |
| Example 27 | 0.110 |
| Example 28 | 0.046 |
| Example 29 | 0.013 |
| Example 30 | 0.006 |
| Example 31 | 0.003 |
| Example 32 | 0.007 |
| Example 33 | 0.004 |
| Example 34 | 0.034 |
| Example 35 | 0.014 |
| Example 36 | 0.004 |
| Example 37 | 0.026 |
| Example 38 | 0.027 |
| Example 39 | 0.013 |
| Example 40 | 0.019 |
| Example 41 | 0.023 |
| Example 42 | 0.030 |
| Example 43 | 0.140 |
| Example 44 | 0.017 |
| Example 45 | 0.008 |
| Example 46 | 0.017 |
| Example 47 | 0.002 |
| Example 48 | 0.007 |
| Example 49 | 0.099 |
| Example 50 | 0.047 |
| Example 51 | 0.047 |
| Example 52 | 0.024 |
| Example 53 | 0.064 |
| Example 54 | 0.024 |
| Example 55 | 0.004 |
| Example 56 | 0.002 |
| Example 57 | 0.007 |
| Example 58 | 0.016 |
| Example 59 | 0.003 |
| Example 60 | 0.008 |
| Example 61 | 0.006 |
| Example 62 | 0.002 |
| Example 63 | 0.002 |
| Example 64 | 0.015 |
| Example 65 | 0.009 |
| Example 66 | 0.012 |
| Example 67 | 0.008 |

Inhibition of Cellular Btk Activity

Alternatively, the present compounds might also be assessed for their capacity to inhibit Btk-dependent FcG receptor-induced IL-8 secretion in human cells. The human myeloid leukemia THP1 cell line (ATCC TIB202) was grown in RPMI 1640 medium supplemented with 10% FCS and 15 nM 1, 25-dihydroxy Vitamin D3 during 4 days before use to induced myeloid differentiation. A sufficient number of tissue-culture grade 384-well plates was coated with human IgG of unknown specificity by incubating overnight at 4° C. with 40 μl/well of a 50 μg/ml IgG solution in PBS. On the day of the experiment, plates were washed 5 times with 80 μl water on a Molecular Devices Aquamax DW4 plate washer. Solutions of the test compounds in 90% DMSO were added to each well on a Hamilton Microlab Star liquid handling station to 40 μl/well tissue culture medium and the total DMSO concentration was adjusted to 0.1%. Differentiated THP1 cells were then added in 40 μl/well to reach a final density of 5'000 cells/well in 80 μl culture medium. After 24 hours, IL-8 secretion was measured in the supernatant by the IL-8 HTRF assay following the protocol of the vendor (CisBio international). Inhibition data were calculated by comparison to control cultures without IgG stimulus enzyme (100% inhibition) and without inhibitors (0% inhibition). The concentration of inhibitor required for 50% inhibition (IC50) was calculated from the inhibition in response to inhibitor concentrations.

| Example | Inhibition of Btk cellular activity IC$_{50}$ [uM] |
|---|---|
| Example 3 | 0.027 |
| Example 16 | 0.069 |
| Example 24 | 0.094 |
| Example 38 | 0.020 |
| Example 62 | 0.071 |

Inhibition of Btk Activity in Blood

Alternatively, the inhibitory activity of the present compounds in blood was assessed in the following in vitro B cell activation assay. Whole blood was collected from the abdominal aorta of anaesthetized adult male Lewis rats and was anticoagulated with 100 U/ml sodium heparin. Blood was then diluted to 50% with high glucose DMEM (Amimed) supplemented with 100 U/ml penicillin, 100 mg/ml streptomycin, 2 mM L-glutamin, 50 mg/ml dextran 40 and 5% FCS (Fetaclone I, Gibco). Then, 190 μl prediluted blood was mixed in 96 well U-bottomed microtiter plates (Nunc) with 10 μl of serial dilutions of test compounds in DMSO. Cultures were incubated at 37° C., 5% CO2 for 1 hour, then 30 μl of rat IL-4 (Beckton-Dickinson, final concentration 5 ng/ml) and goat anti-rat IgM (Serotec, final concentration 15 ug/ml) were added and the cultures were incubated for 24 hours. Activation of B cells was measured by flow cytometry after staining for the B cell subset with PE-Cy5-labeled anti-ratCD45RA (Beckton-Dickinson) and for the activation marker CD86 (PE-labeled anti-rat CD86 (Beckton-Dickinson). All staining procedures were performed at RT for 30 min in the dark in 96-deep well V-bottomed microtiter plates (Corning) with BD Lysing Solution (Beckton-Dickinson). Cytometric data was acquired on a FACScalibur flow cytometer (BD Biosciences) and the subpopulation of lymphocytes were gated according to size and granularity and further analyzed for expression of CD45RA and the activation markers. Data for the inhibition of B cell activation were calculated from the percentage of cells positively stained for activation markers within the CD45RA positive population. Inhibition data were calculated by comparison to control cultures without anti-IgM and IL-4 (100% inhibition) and without inhibitors (0% inhibition). The concentration of inhibitor required for 50% inhibition (IC50) was calculated from the inhibition in response to inhibitor concentrations.

| Example | Inhibition of Btk activity in blood IC$_{50}$ [uM] |
|---|---|
| Example 2 | 0.072 |
| Example 6 | 0.112 |
| Example 17 | 0.100 |
| Example 32 | 0.414 |
| Example 58 | 0.179 |

Utilities

Based for example upon the biological test results, compounds of the invention may generally be useful in the treatment of an indication selected from:

Autoimmune disorders, inflammatory diseases, allergic diseases, airway diseases, such as asthma and chronic obstructive pulmonary disease (COPD), transplant rejection; diseases in which antibody production, antigen presentation, cytokine production or lymphoid organogenesis are abnormal or are undesirable; including rheumatoid arthritis, systemic onset juvenile idiopathic arthritis (SOJIA), gout, pemphigus vulgaris, idiopathic thrombocytopenic purpura, systemic lupus erythematosus, multiple sclerosis, myasthenia gravis, Sjögren's syndrome, autoimmune hemolytic anemia, anti-neutrophil cytoplasmic antibodies (ANCA)-associated vasculitides, cryoglobulinemia, thrombotic thrombocytopenic purpura, chronic autoimmune urticaria, allergy (atopic dermatitis, contact dermatitis, allergic rhinitis), atherosclerosis, type 1 diabetes, type 2 diabetes, inflammatory bowel disease, ulcerative colitis, morbus Crohn, pancreatitis, glomerolunephritis, Goodpasture's syndrome, Hashimoto's thyroiditis, Grave's disease, antibody-mediated transplant rejection (AMR), graft versus host disease, B cell-mediated hyperacute, acute and chronic transplant rejection; thromboembolic disorders, myocardial infarct, angina pectoris, stroke, ischemic disorders, pulmonary embolism; cancers of haematopoietic origin including but not limited to multiple myeloma; a leukaemia; acute myelogenous leukemia; chronic myelogenous leukemia; lymphocytic leukemia; myeloid leukemia; non-Hodgkin lymphoma; lymphomas; polycythemia vera; essential thrombocythemia; myelofibrosis with myeloid metaplasia; and Waldenstroem disease.

In a further embodiment, the therapy is selected from a disease which may be treated by an antagonist of Bruton's tyrosine kinase.

In another embodiment, the invention provides a method of treating a disease which is treated by the modulation of Btk-comprising administration of a therapeutically acceptable amount of a compound of formula (I) or a salt thereof. In a further embodiment, the disease is selected from the aforementioned lists Combinations The compound of the present invention may be administered either simultaneously with, or before or after, one or more other therapeutic agent. The compound of the present invention may be administered separately, by the same or different route of administration, or together in the same pharmaceutical composition as the other agents.

The compounds of formula (I) may be administered as the sole active ingredient or in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders, or a chemotherapeutic agent, e.g a malignant cell anti-proliferative agent. For example, the compounds of formula (I) may be used in combination with a calcineurin inhibitor, e.g. cyclosporin A or FK 506; a mTOR inhibitor, e.g. rapamycin, 40-O-(2-hydroxyethyl)-rapamycin, CCI779, ABT578, AP23573, AP23464, AP23675, AP23841, TAFA-93, biolimus-7 or biolimus-9; an ascomycin having immunosuppressive properties, e.g. ABT-281, ASM981, etc.; corticosteroids; cyclophosphamide; azathioprene; methotrexate; leflunomide; mizoribine; mycophenolic acid or salt; mycophenolate mofetil; 15-deoxyspergualine or an immunosuppressive homologue, analogue or derivative thereof; a PKC inhibitor, e.g. as disclosed in WO 02/38561 or WO 03/82859, e.g. the compound of Example 56 or 70; a JAK3 kinase inhibitor, e.g. N-benzyl-3,4-dihydroxy-benzylidene-cyanoacetamide α-cyano-(3,4-dihydroxy)-]N-benzylcinnamamide (Tyrphostin AG 490), prodigiosin 25-C(PNU156804), [4-(4'-hydroxyphenyl)-amino-6,7-dimethoxyquinazoline] (WHI-P131), [4-(3'-bromo-4'-hydroxylphenyl)-amino-6,7-dimethoxyquinazoline] (WHI-P154), [4-(3',5'-dibromo-4'-hydroxylphenyl)-amino-6,7-dimethoxyquinazoline] WHI-P97, KRX-211, 3-{(3R,4R)-4-methyl-3-[methyl-(7H-pyrrolo[2,3-d]pyrimidin-4-yl)-amino]-piperidin-1-yl}-3-oxo-propionitrile, in free form or in a pharmaceutically acceptable salt form, e.g. mono-citrate (also called CP-690,550), or a compound as disclosed in WO 04/052359 or WO 05/066156; sphingosine-1-phosphate receptor modulators such as FTY720 (fingolimod), or compounds disclosed in WO 2005/000833; immunosuppressive monoclonal antibodies, e.g., monoclonal antibodies to leukocyte receptors, e.g., MHC, CD2, CD3, CD4, CD7, CD8, CD25, CD28, CD40, CD45, CD52, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or a chemotherapeutic agent, e.g. paclitaxel, gemcitabine, cisplatinum, doxorubicin or 5-fluorouracil; or an anti-infectious agent. Further combination partners to a compound of formula (I) may be selected from a PI3K inhibitor (e.g. pan, or alpha, beta, gamma, delta selectives), TNF inhibitors, IL1beta inhibitors, IL17 inhibitors, and inhibitors of IL6 or IL receptor.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula (I) and a co-agent, are both administered to a patient simultaneously in the form of a single entity or dosage. The term "non-fixed combination" means that the active ingredients, e.g. a compound of formula (I) and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by Btk kinases. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by Btk kinases, wherein the medicament is prepared for administration with another therapeutic agent. The invention also provides the use of another therapeutic agent for treating a disease or condition mediated by Btk, wherein the medicament is administered with a compound of formula (I).

The invention also provides a compound of formula (I) for use in a method of treating a disease or condition mediated by Btk, wherein the compound of formula (I) is prepared for administration with another therapeutic agent. The invention also provides another therapeutic agent for use in a method of treating a disease or condition mediated by Btk, wherein the other therapeutic agent is prepared for administration with a compound of formula (I). The invention also provides a compound of formula (I) for use in a method of treating a disease or condition mediated by Btk, wherein the compound of formula (I) is administered with another therapeutic agent. The invention also provides another therapeutic agent for use in a method of treating a disease or condition mediated by Btk, wherein the other therapeutic agent is administered with a compound of formula (I).

The invention claimed is:

1. A compound of formula (I) or a pharmaceutically acceptable salt thereof;

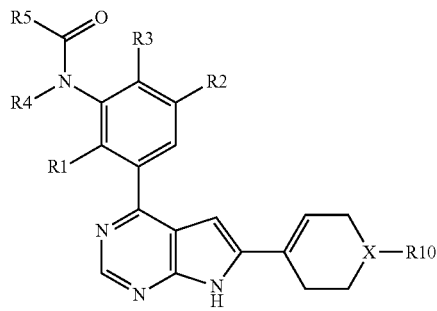

wherein,
R1 is hydrogen or $C_1$-$C_6$ alkyl optionally substituted by hydroxy;
R2 is hydrogen or halogen;
R3 is hydrogen or halogen;
R4 is hydrogen,
R5 is phenyl optionally substituted by halogen; $SF_5$; NR6R7; hydroxy; $C_1$-$C_6$ alkoxy; $C_1$-$C_6$ alkenyl; $C_1$-$C_6$ alkyl carbonyl; $C_1$-$C_6$ alkyl optionally substituted by hydroxy, halogen, or $C_1$-$C_6$ alkoxy; or $C_3$-$C_6$ cycloalkyl optionally substituted by halogen, hydroxy, or $C_1$-$C_6$ alkyl optionally substituted by halogen; or
R5 is a 4-14 membered mono- or bicyclic heterocyclyl or heteroaryl ring system comprising 1, 2 or 3 heteroatoms selected from N, S and O that ring being optionally substituted by halogen; hydroxy; $C_1$-$C_6$ alkoxy optionally substituted by hydroxy or halogen; or $C_1$-$C_6$ alkyl optionally substituted by hydroxy or halogen;
or R4 and R5 together with the atoms to which they are bound form a piperidone ring, optionally comprising an annulated phenyl ring, any such ring being optionally substituted by $C_1$-$C_6$ alkyl, $C_1$-$C_6$ alkoxy, or $C_3$-$C_6$ cycloalkyl each of which substitution member may optionally be substituted by halogen or hydroxy;
R6 and R7 are independently selected from hydrogen or $C_1$-$C_6$ alkyl;
or R6 and R7 together with the nitrogen atom to which they are bound form a 4-8 membered saturated azacycloalkane ring, optionally substituted by halogen, hydroxy or $C_1$-$C_6$ alkyl;
X is O, $S(O)_n$ wherein n is 0, 1 or 2, or

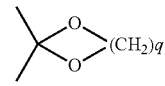

wherein q is 2 or 3, and R10 is absent;
or X is CH or N; and R10 is hydrogen, hydroxy, —NR6R7, —CO—R11, —S(O)$_P$—R12 wherein p is 1 or 2,
R 11 is $C_1$-$C_6$ alkyl optionally substituted by hydroxy, cyano, halogen, carboxy or $C_1$-$C_6$ alkoxy carbonyloxy; or NR6R7; and
R12 is $C_1$-$C_6$ alkyl or NR6R7.

2. The compound according to claim 1 or a pharmaceutically acceptable salt thereof, wherein R1 is hydrogen, methyl or hydroxymethyl, R2 and R3 are independently hydrogen or fluoro, R4 is hydrogen; R5 is phenyl substituted by halogen; $C_1$-$C_6$ alkoxy; $C_1$-$C_6$ alkyl optionally substituted by halogen or hydroxy; or $C_3$-$C_6$ cycloalkyl optionally substituted by halogen, hydroxy, or $C_1$-$C_6$ alkyl optionally substituted by halogen; X is O, $S(O)_n$ wherein n is 0, 1 or 2, or

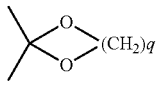

wherein q is 2 or 3, and R10 is absent;
and the remaining variables are as defined in claim 1.

3. The compound according to claim 1, or a pharmaceutically acceptable salt thereof, wherein R1 is hydrogen, methyl or hydroxymethyl, R2 and R3 are independently hydrogen or fluoro, R4 together with R5 is a 3,4-dihydro-2H-isoquinolin-1-one optionally substituted by $C_3$-$C_6$ cycloalkyl or $C_1$-$C_6$ alkyl optionally substituted by hydroxy; X is O, $S(O)_n$ wherein n is 0, 1 or 2, or

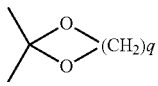

wherein q is 2 or 3, and R10 is absent;
and the remaining variables are as defined in claim 1.

4. The compound according to claim 1, or a pharmaceutically acceptable salt thereof, wherein R1 is hydrogen, methyl or hydroxymethyl, R2 and R3 are independently hydrogen or fluoro, R4 is hydrogen; R5 is phenyl substituted by halogen; $C_1$-$C_6$ alkoxy; $C_1$-$C_6$ alkyl optionally substituted by halogen or hydroxy; or $C_3$-$C_6$ cycloalkyl optionally substituted by halogen, hydroxy, or $C_1$-$C_6$ alkyl optionally substituted by halogen; X stands for 0 and R10 is absent; or X stands for N, and R10 is hydrogen or —CO—R11, and the remaining variables are as defined in claim 1.

5. The compound according to claim 1, or a pharmaceutically acceptable salt thereof, wherein R1 is hydrogen, methyl or hydroxymethyl, R2 and R3 are independently hydrogen or fluoro, R4 is hydrogen; R5 is phenyl substituted by $C_1$-$C_6$ alkoxy; $C_1$-$C_6$ alkyl optionally substituted by halogen or hydroxy; or $C_3$-$C_6$ cycloalkyl optionally substituted by halogen, hydroxy, or $C_1$-$C_6$ alkyl optionally substituted by halogen; X stands for N, R10 is hydrogen or —CO—R11, R11 stands for NR6R7 wherein R6 and R7 are independently hydrogen or methyl; and the remaining variables are as defined in claim 1.

6. The compound according to claim 1, or a pharmaceutically acceptable salt thereof, wherein R1 is hydrogen, methyl or hydroxymethyl, R2 and R3 are independently hydrogen or fluoro, R4 is hydrogen, R5 is azetidine optionally substituted by $C_1$-$C_6$ alkoxy, X stands for N, and R10 is hydrogen or —CO—R11, and the remaining variables are as defined in claim 1.

7. The compound according to claim 1, or a pharmaceutically acceptable salt thereof, wherein R1 is hydrogen, methyl or hydroxymethyl, R2 and R3 are independently hydrogen or fluoro, R4 together with R5 is a 3,4-dihydro-2H-isoquinolin-1-one optionally substituted by $C_3$-$C_6$ cycloalkyl or $C_1$-$C_6$ alkyl optionally substituted by hydroxy, X stands for N, and R10 is hydrogen or —CO—R11, and the remaining variables are as defined in claim 1.

8. The compound according to claim 1, or a pharmaceutically acceptable salt thereof, wherein R1 is hydrogen, methyl or hydroxymethyl, R2 and R3 are independently hydrogen or fluoro, R4 together with R5 is a 3,4-dihydro-2H-isoquinolin-1-one substituted by $C_3$-$C_6$ cycloalkyl or $C_1$-$C_6$ alkyl optionally substituted by hydroxy in the 6-position of said isoquinolin-ring, X stands for N, and R10 is hydrogen or —CO—R11, and the remaining variables are as defined in claim 1.

9. The compound according to claim 1, or a pharmaceutically acceptable salt thereof, wherein R1 is hydrogen, methyl or hydroxymethyl, R2 and R3 are independently hydrogen or fluoro, R4 is hydrogen, R5 is azetidine optionally substituted by $C_1$-$C_6$ alkoxy, X stands for 0, and the remaining variables are as defined in claim 1.

10. The compound according to claim 1, or a pharmaceutically acceptable salt thereof, wherein R1 is hydrogen, methyl or hydroxymethyl, R2 and R3 are independently hydrogen or fluoro, R4 together with R5 is a 3,4-dihydro-2H-isoquinolin-1-one optionally substituted by $C_3$-$C_6$ cycloalkyl or $C_1$-$C_6$ alkyl optionally substituted by hydroxy, X stands for 0, and the remaining variables are as defined claim 1.

11. The compound of claim 1, or a pharmaceutically acceptable salt thereof, which is selected from:
4-(4-{5-Fluoro-3-[4-(1-fluoro-cyclopropyl)-benzoylamino]-2-methyl-phenyl}-7H-pyrrolo[2'3-d]pyrimidin-6-yl)-3,6-dihydro-2H-pyridine-1-carboxylic acid dimethylamide,
4-(4-{3-[(3,3-Dimethyl-2,3-dihydro-benzofuran-6-carbonyl)-amino]-5-fluoro-2-methyl-phenyl}-7H-pyrrolo[2'3-d]pyrimidin-6-yl)-3,6-dihydro-2H-pyridine-1-carboxylic acid dimethylamide,
4-(4-{5-Fluoro-2-methyl-3-[(5-methyl-4,5,6,7-tetrahydro-benzo[b]thiophene-2-carbonyl)-amino]-phenyl}-7H-pyrrolo[2'3-d]pyrimidin-6-yl)-3,6-dihydro-2H-pyridine-1-carboxylic acid dimethylamide,
4-(4-{5-Fluoro-3-[4-isopropyl-methyl-amino)-benzoylamino]-2-methyl-phenyl}-7H-pyrrolo[2'3-d]pyrimidin-6-yl)-3,6-dihydro-2H-pyridine-1-carboxylic acid dimethylamide,
3-Methyl-1H-indole-6-carboxylic acid {3-[6-(1-dimethylcarbamoyl-1,2,3,6-tetrahydro-pyridin-4-yl)-7H-pyrrolo[2,3-d]pyrimidin-4-yl]-5-fluoro-2-methyl-phenyl}-amide,
4-(4-{5-Fluoro-3-[4-(2-hydroxy-1,1-dimethyl-ethyl)-benzoylamino]-2-methyl-phenyl}-7H-pyrrolo[2,3-d]pyrimidin-6-yl)-3,6-dihydro-2H-pyridine-1-carboxylic acid dimethylamide,
4-{4-[5-Fluoro-2-methyl-3-(4-piperidin-1-yl-benzoylamino)-phenyl]-7H-pyrrolo[2,3-d]pyrimidin-6-yl}-3,6-dihydro-2H-pyridine-1-carboxylic acid dimethylamide,
4-{4-[5-Fluoro-3-(isopropenyl-benzoylamino)-2-methyl-phenyl]-7H-pyrrolo[2,3-d]pyrimidin-6-yl}-3,6-dihydro-2H-pyridine-1-carboxylic acid dimethylamide,
4-(4-{5-Fluoro-2-methyl-3-[4-(1-trifluoromethyl-cyclopropyl)-benzoylamino]-phenyl}-7H-pyrrolo[2,3-d]pyrimidin-6-yl)-3,6-dihydro-2H-pyridine-1-carboxylic acid dimethylamide,
4-{4-[5-Fluoro-3-(4-isopropoxy-benzoylamino)-2-methyl-phenyl]-7H-pyrrolo[2,3-d]pyrimidin-6-yl}-3,6-dihydro-2H-pyridine-1-carboxylic acid dimethylamide,
4-(4-{5-Fluoro-3-[4-pentafluorothio-benzoylamino]-2-methyl-phenyl}-7H-pyrrolo[2,3-d]pyrimidin-6-yl)-3,6-dihydro-2H-pyridine-1-carboxylic acid dimethylamide,
4-(4-{5-Fluoro-3-[4-(2-methoxy-1,1-dimethyl-ethyl)-benzoylamino]-2-methyl-phenyl}-7H-pyrrolo[2,3-d]pyrimidin-6-yl)-3,6-dihydro-2H-pyridine-1-carboxylic acid dimethylamide,
4-(4-{5-Fluoro-3-[4-(1-methoxy-1-methyl-ethyl)-benzoylamino]-2-methyl-phenyl}-7H-pyrrolo[2,3-d]pyrimidin-6-yl)-3,6-dihydro-2H-pyridine-1-carboxylic acid dimethylamide, 1-Methyl-1H-pyrrolo[2,3-b]pyridine-6-carboxylic acid {3-[6-(1-dimethyl-carbamoyl-1,2,3,6-tetrahydro-pyridin-4-yl)-7H-pyrrolo[2,3-d]pyrimidin-4-yl]-5-fluoro-2-methyl-phenyl}-amide, 4-{4-[3-(4-Dimethylamino-benzoylamino)-5-fluoro-2-methyl-phenyl]-7H-pyrrolo[2,3-d]pyrimidin-6-yl}-3,6-dihydro-2H-pyridine-1-carboxylic acid dimethylamide, 4-(4-{3-[2-Fluoro-4-(1-hydroxy-1-methyl-ethyl)-benzoylamino]-2-hydroxymethyl-phenyl}-7H-pyrrolo[2,3-d]pyrimidin-6-yl)-3,6-dihydro-2H-pyridine-1-carboxylic acid dimethylamide, 4-{4-[3-(4-Cyclopropyl-benzoylamino)-2-hydroxymethyl-phenyl]-7H-pyrrolo[2,3-d]pyrimidin-6-yl}-3,6-dihydro-2H-pyridine-1-carboxylic acid dimethylamide, 4-(4-{5-Fluoro-2-methyl-3-[4-(2,2,2-trifluoro-1-hydroxy-1-methyl-et hyl)-benzoylamino]-phenyl}-7H-pyrrolo[2,3-d]pyrimidin-6-yl)-3,6-dihydro-2H-pyridine-1-carboxylic acid dimethylamide, 4-{4-[3-(4-Acetyl-benzoylamino)-5-fluoro-2-methyl-phenyl]-7H-pyrrolo[2,3-d]pyrimidin-6-yl}-3,6-dihydro-2H-pyridine-1-carboxylic acid dimethylamide, 4-{4-[3-(4-Cyclopropyl-benzoylamino)-4-fluoro-phenyl]-7H-pyrrolo[2,3-d]pyrimidin-6-yl}-3,6-dihydro-2H-pyridine-1-carboxylic acid dimethylamide, 4-(4-{4-Fluoro-3-[4-(2-hydroxy-1,1-dimethyl-ethyl)-benzoylamino]-phenyl}-7H-pyrrolo[2,3-d]pyrimidin-6-yl)-3,6-dihydro-2H-pyridine-1-carboxylic acid dimethylamide, N-{3-[6-(3,6-Dihydro-2H-pyran-4-yl)-7H-pyrrolo[2,3-d]pyrimidin-4-yl]-5-fluoro-2-methyl-phenyl}-2-fluoro-4-(1-hydroxy-1-methyl-ethyl)-benzamide, N-{3-[6-(3,6-Dihydro-2H-pyran-4-yl)-7H-pyrrolo[2,3-d]pyrimidin-4-yl]-2-hydroxymethyl-phenyl}-2-fluoro-4-(1-hydroxy-1-methyl-ethyl)-benzamide, 4-tert-Butyl-N-{3-[6-(3,6-dihydro-2H-thiopyran-4-yl)-7H-pyrrolo[2,3-d]pyrimidin-4-yl]-5-fluoro-2-methyl-phenyl}-benzamide, 4-tert-Butyl-N-{5-fluoro-2-methyl-3-[6-(3,6-dihydro-1-oxido-2H-thiopyran-4-yl)-7H-pyrrolo[2,3-d]pyrimidin-4-yl]-phenyl}-benzamide, 4-tert-Butyl-N-{3-[6-(3,6-dihydro-1,1-dioxido-2H-thiopyran-4-yl)-7H-pyrrolo[2,3-d]pyrimidin-4-yl]-5-fluoro-2-methyl-phenyl}-benzamide, 4-tert-Butyl-N-{3-[6-(1,4-dioxa-spiro[4.5]dec-7-en-8-yl)-7H-pyrrolo[2,3-d]pyrimidin-4-yl]-5-fluoro-2-methyl-phenyl}-benzamide, 4-tert-Butyl-N-{5-fluoro-3-[6-(4-hydroxy-cyclohex-1-enyl)-7H-pyrrolo[2,3-d]pyrimidin-4-yl]-2-methyl-phenyl}-benzamide, 4-{4-[3-(4-Cyclopropyl-benzoylamino)-5-fluoro-2-methyl-phenyl]-7H-pyrrolo[2'3-d]pyrimidin-6-yl}-3,6-dihydro-2H-pyridine-1-carboxylic acid dimethylamide, 4-Cyclopropyl-N-(5-fluoro-2-methyl-{6-[1-(pyrrolidine-1-carbonyl)-1,2,3,6-tetrahydro-pyridin-4-yl]-7H-pyrrolo[2,3-d]pyrimidin-4-yl}-phenyl)-benzamide, Acetic acid 2-(4-{4-[3-(4-cyclopropyl-benzoylamino)-5-fluoro-2-methyl-phenyl]-7H-pyrrolo[2,3-d]pyrimidin-6-yl}-3,6-dihydro-2H-pyridin-1-yl)-2-oxo-ethyl ester, 4-Cyclopropyl-N-(5-fluoro-3-{6-[1-(2-hydroxy-acetyl)-1,2,3,6-tetrahydro-pyridin-4-yl]-7H-pyrrolo[2,3-d]pyrimidin-4-yl}-2-methyl-phenyl)benzamide, N-(3-{6-[1-(2-Cyano-acetyl)-1,2,3,6-tetrahydro-pyridin-4-yl]-7H-pyrrolo[2,3-d]pyrimidin-4-yl}-5-fluoro-2-methyl-phenyl)-4-cyclopropyl-benzamide, N-(5-Fluoro-2-methyl-3-{6-[1-(pyrrolidine-1-carbonyl)-1,2,3,6-tetrahydro-pyridin-4-yl]-7H-pyrrolo[2,3-d]pyrimidin-4-yl}-phenyl)-4-(pentafluoro-sulfanyl)-benzamide, Acetic acid 2-[4-(4-{5-fluoro-2-methyl-3-[4-(pentafluoro-sulfanyl)-benzoylamino]-phenyl}-7H-pyrrolo[2,3-d]pyrimidin-6-yl)-3,6-dihydro-2H-pyridin-1-yl]-2-oxo-ethyl ester, N-(5-Fluoro-3-{6-[1-(2-hydroxy-acetyl)-1,2,3,6-tetrahydro-pyridin-4-yl]-7H-pyrrolo[2,3-d]pyrimidin-4-yl}-2-methyl-phenyl)-4-(pentafluoro-sulfanyl)-benzamide, 4-{4-[3-(4-tert-Butyl-benzoylamino)-2-(tert-butyl-diphenyl-silanyloxymethyl)-phenyl]-7H-pyrrolo[2,3-d]pyrimidin-6-yl}-3,6-dihydro-2H-pyridine-1-carboxylic acid tert-butyl ester, 4-tert-Butyl-N-(3-{6-[1-(2-fluoro-acetyl)-1,2,3,6-tetrahydro-pyridin-4-yl]-7H-pyrrolo[2,3-d]pyrimidin-4-yl}-2-hydroxymethyl-phenyl)-benzamide, 4-(4-{5-Fluoro-3-[2-fluoro-4-(1-hydroxy-1-methyl-ethyl)-benzoylamino]-2-methyl-phenyl}-7H-pyrrolo[2,3-d]pyrimidin-6-yl)-3,6-dihydro-2H-pyridine-1-carboxylic acid dimethylamide, 4-tert-Butyl-N-{5-fluoro-2-methyl-3-[6-(1,2,3,6-tetrahydro-pyridin-4-yl)-7H-pyrrolo[2,3-d]pyrimidin-4-yl]-phenyl}-benzamide, 4-{4-[3-(4-tert-Butyl-benzoylamino)-5-fluoro-2-methyl-phenyl]-7H-pyrrolo[2,3-d]pyrimidin-6-yl}-3,6-dihydro-2H-pyridine-1-carboxylic acid dimethylamide, 4-tert-Butyl-N-{5-fluoro-3-[6-(1-methanesulfonyl-1,2,3,6-tetrahydro-pyridin-4-yl)-7H-pyrrolo[2,3-d]pyrimidin-4-yl]-2-methyl-phenyl}-benzamide, 4-tert-Butyl-N-{3-[6-(1-dimethylsulfamoyl-1,2,3,6-tetrahydro-pyridin-4-yl)-7H-pyrrolo[2,3-d]pyrimidin-4-yl]-5-fluoro-2-methyl-phenyl}-benzamide, 4-tert-Butyl-N-{3-[6-(1-methanesulfonyl-1,2,3,6-tetrahydro-pyridin-4-yl)-7H-pyrrolo[2,3-d]pyrimidin-4-yl]-2-methyl-phenyl}-benzamide, 4-{4-[3-(6-tert-Butyl-1-oxo-3,4-dihydro-1H-isoquinolin-2-yl)-2-hydroxymethyl-phenyl]-7H-pyrrolo[2,3-d]pyrimidin-6-yl}-3,6-dihydro-2H-pyridine-1-carboxylic acid dimethylamide, 4-{4-[3-(6-Cyclopropyl-1-oxo-3,4-dihydro-1H-isoquinolin-2-yl)-2-hydroxymethyl-phenyl]-7H-pyrrolo[2,3-d]pyrimidin-6-yl}-3,6-dihydro-2H-pyridine-1-carboxylic acid dimethylamide, 4-(4-{2-Hydroxymethyl-3-[6-(1-hydroxy-1-methyl-ethyl)-1-oxo-3,4-dihydro-1H-isoquinolin-2-yl]-phenyl}-7H-pyrrolo[2,3-d]pyrimidin-6-yl)-3,6-dihydro-2H-pyridine-1-carboxylic acid dimethylamide, 4-tert-Butyl-N-{3-[6-(3,6-dihydro-2H-pyran-4-yl)-7H-pyrrolo[2,3-d]pyrimidin-4-yl]-2-hydroxymethyl-phenyl}-benzamide, 4-tert-Butyl-N-{3-[6-(3,6-dihydro-2H-pyran-4-yl)-7H-pyrrolo[2,3-d]pyrimidin-4-yl]-5-fluoro-2-methyl-phenyl}-benzamide, N-{3-[6-(3,6-Dihydro-2H-pyran-4-yl)-7H-pyrrolo[2,3-d]pyrimidin-4-yl]-5-fluoro-2-methyl-phenyl}-4-dimethylamino-benzamide, 4-tert-Butyl-N-{3-[6-(3,6-dihydro-2H-thiopyran-4-yl)-7H-pyrrolo[2,3-d]pyrimidin-4-yl]-2-methyl-phenyl}-benzamide, 4-tert-Butyl-N-{2-methyl-3-[6-(3,6-dihydro-1-oxido-2H-thiopyran-4-yl)-7H-pyrrolo[2,3-d]pyrimidin-4-yl]-phenyl}-benzamide, 4-tert-Butyl-N-{3-[6-(3,6-dihydro-1,1-dioxido-2H-thiopyran-4-yl)-7H-pyrrolo[2,3-d]pyrimidin-4-yl]-2-methyl-phenyl}-benzamide, 4-tert-Butyl-N-{3-[6-(1,4-dioxa-spiro[4.5]dec-7-en-8-yl)-7H-pyrrolo[2,3-d]pyrimidin-4-yl]-2-hydroxymethyl-phenyl}-benzamide, 4-tert-Butyl-N-{3-[6-(4-hydroxy-cyclohex-1-enyl)-7H-pyrrolo[2,3-d]pyrimidin-4-yl]-2-hydroxymethyl-phenyl}-benzamide, 4-tert-Butyl-N-{3-[6-(4-dimethylamino-cyclohex-1-enyl)-7H-pyrrolo[2,3-d]pyrimidin-4-yl]-2-hydroxymethyl-phenyl}-benzamide, 4-(4-{3-[(3-tert-Butoxy-azetidine-1-carbonyl)-amino]-5-fluoro-2-methyl-phenyl}-7H-pyrrolo[2,3-d]pyrimidin-6-yl)-3,6-dihydro-2H-pyridine-1-carboxylic acid dimethylamide, 4-(4-{5-Fluoro-3-[(3-isopropoxy-azetidine-1-carbonyl)-amino]-2-methyl-phenyl}-7H-pyrrolo[2,3-d]pyrimidin-6-yl)-3,6-dihydro-2H-pyridine-1-carboxylic acid dimethylamide, 5-Fluoro-1,3-dihydro-isoindole-2-carboxylic acid {3-[6-(1-dimethylcarbamoyl-1,2,3,6-tetrahydro-pyridin-4-yl)-7H-pyrrolo[2,3-d]pyrimidin-4-yl]-5-fluoro-2-methyl-phenyl}-amide, 4-[4-(5-Fluoro-2-methyl-3-{[3-(2,2,2-trifluoro-1-trifluoromethyl-ethoxy)-azetidine-1-carbonyl]-amino}-phenyl)-7H-pyrrolo[2,3-d]pyrimidin-6-yl]-3,6-dihydro-2H-pyridine-1-carboxylic acid dimethylamide, 3-tert-Butoxy-azetidine-1-carboxylic acid {3-[6-(3,6-dihydro-2H-pyran-4-yl)-7H-pyrrolo[2,3-d]pyrimidin-4-yl]-5-fluoro-2-methyl-phenyl}-amide, 4-(4-{3-[(3-tert-Butoxy-azetidine-1-carbonyl)-amino]-4-fluoro-phenyl}-7H-pyrrolo[2,3-d]pyrimidin-6-yl)-3,6-dihydro-2H-pyridine-1-carboxylic acid dimethylamide, 4-(4-{3-[(3-tert-Butoxy-azetidine-1-carbonyl)-amino]-4-fluoro-2-methyl-phenyl}-7H-pyrrolo[2,3-d]pyrimidin-6-yl)-3,6-dihydro-2H-pyridine-1-carboxylic acid dimethylamide, 4-tert-Butyl-N-{3-[6-(3,6-dihydro-2H-pyran-4-yl)-7H-pyrrolo[2,3-d]pyrimidin-4-yl]-2-methyl-phenyl}-benzamide, 4-tert-Butyl-N-{3-[6-(1,4-dioxa-spiro[4.5]dec-7-en-8-yl)-7H-pyrrolo[2,3-d]pyrimidin-4-yl]-2-methyl-phenyl}-benzamide, 4-tert-Butyl-N-{3-[6-(4-hydroxy-cyclohex-1-enyl)-7H-pyrrolo[2,3-d]pyrimidin-4-yl]-2-methyl-phenyl}-benzamide, and 4-tert-Butyl-N-{3-[6-(4-dimethylamino-cyclohex-1-enyl)-7H-pyrrolo[2,3-d]pyrimidin-4-yl]-2-methyl-phenyl}-benzamide.

12. The compound claim 1, or a pharmaceutically acceptable salt thereof, which is selected from:

4-{4-[3-(4-Acetyl-benzoylamino)-5-fluoro-2-methyl-phenyl]-7H-pyrrolo[2,3-d]pyrimidin-6-yl}-3,6-dihydro-2H-pyridine-1-carboxylic acid dimethylamide;

4-{4-[3-(4-Cyclopropyl-benzoylamino)-4-fluoro-phenyl]-7H-pyrrolo[2,3-d]pyrimidin-6-yl}-3,6-dihydro-2H-pyridine-1-carboxylic acid dimethylamide;

4-(4-{4-Fluoro-3-[4-(2-hydroxy-1,1-dimethyl-ethyl)-benzoylamino]-phenyl}-7H-pyrrolo[2,3-d]pyrimidin-6-yl)-3,6-dihydro-2H-pyridine-1-carboxylic acid dimethylamide;

N-{3-[6-(3,6-Dihydro-2H-pyran-4-yl)-7H-pyrrolo[2,3-d]pyrimidin-4-yl]-5-fluoro-2-methyl-phenyl}-2-fluoro-4-(1-hydroxy-1-methyl-ethyl)-benzamide;

N-{3-[6-(3,6-Dihydro-2H-pyran-4-yl)-7H-pyrrolo[2,3-d]pyrimidin-4-yl]-2-hydroxymethyl-phenyl}-2-fluoro-4-(1-hydroxy-1-methyl-ethyl)-benzamide;

4-tert-Butyl-N-{3-[6-(3,6-dihydro-2H-thiopyran-4-yl)-7H-pyrrolo[2,3-d]pyrimidin-4-yl]-5-fluoro-2-methyl-phenyl}-benzamide;

4-tert-Butyl-N-{5-fluoro-2-methyl-3-[6-(3,6-dihydro-1-oxido-2H-thiopyran-4-yl)-7H-pyrrolo[2,3-d]pyrimidin-4-yl]-phenyl}-benzamide;

4-tert-Butyl-N-{3-[6-(3,6-dihydro-1,1-dioxido-2H-thiopyran-4-yl)-7H-pyrrolo[2,3-d]pyrimidin-4-yl]-5-fluoro-2-methyl-phenyl}-benzamide;

4-tert-Butyl-N-{3-[6-(1,4-dioxa-spiro[4.5]dec-7-en-8-yl)-7H-pyrrolo[2,3-d]pyrimidin-4-yl]-5-fluoro-2-methyl-phenyl}-benzamide;

4-tert-Butyl-N-{5-fluoro-3-[6-(4-hydroxy-cyclohex-1-enyl)-7H-pyrrolo[2,3-d]pyrimidin-4-yl]-2-methyl-phenyl}-benzamide;

4-{4-[3-(4-Cyclopropyl-benzoylamino)-5-fluoro-2-methyl-phenyl]-7H-pyrrolo[2'3-d]pyrimidin-6-yl}-3,6-dihydro-2H-pyridine-1-carboxylic acid dimethylamide;

4-Cyclopropyl-N-(5-fluoro-2-methyl-3-{6-[1-(pyrrolidine-1-carbonyl)-1,2,3,6-tetrahydro-pyridin-4-yl]-7H-pyrrolo[2,3-d]pyrimidin-4-yl}-phenyl)-benzamide;

Acetic acid 2-(4-{4-[3-(4-cyclopropyl-benzoylamino)-5-fluoro-2-methyl-phenyl]-7H-pyrrolo[2,3-d]pyrimidin-6-yl}-3,6-dihydro-2H-pyridin-1-yl)-2-oxo-ethyl ester; and 4-Cyclopropyl-N-(5-fluoro-3-{6-[1-(2-hydroxy-actyl)-1,2,3,6-tetrahydro-pyridin-4-yl]-7H-pyrrolo[2,3-d]pyrimidin-4-yl}-2-methyl-phenyl)benzamide.

13. A pharmaceutical composition comprising a therapeutically effective amount of a compound according to claim 1 and one or more pharmaceutically acceptable carriers.

14. A combination comprising a therapeutically effective amount of a compound according to claim 1 or a pharmaceutically acceptable salt thereof and one or more therapeutically active co-agents.

15. A method of inhibiting Btk activity in a subject, wherein the method comprises administering to the subject a therapeutically effective amount of the compound according to claim 1 or a pharmaceutically acceptable salt thereof.

* * * * *